US011932877B2

(12) United States Patent
Wauthier et al.

(10) Patent No.: US 11,932,877 B2
(45) Date of Patent: Mar. 19, 2024

(54) HUMAN FIBROLAMELLAR HEPATOCELLULAR CARCINOMAS (HFL-HCCS)

(71) Applicant: University of North Carolina at Chapel Hill, Chapel Hill, NC (US)

(72) Inventors: Eliane Wauthier, Chapel Hill, NC (US); Tsunekazu Oikawa, Chapel Hill, NC (US); Timothy Anh-Hieu Dinh, Chapel Hill, NC (US); Praveen Sethupathy, Chapel Hill, NC (US); Lola M. Reid, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/011,534

(22) Filed: Jun. 18, 2018

(65) Prior Publication Data

US 2019/0161735 A1    May 30, 2019

Related U.S. Application Data

(63) Continuation of application No. 15/061,626, filed on Mar. 4, 2016, now abandoned.

(60) Provisional application No. 62/129,668, filed on Mar. 6, 2015.

(51) Int. Cl.
| | |
|---|---|
| *C12N 5/09* | (2010.01) |
| *C12Q 1/6886* | (2018.01) |
| *G01N 33/50* | (2006.01) |
| *G01N 33/574* | (2006.01) |

(52) U.S. Cl.
CPC ........ *C12N 5/0693* (2013.01); *A01K 67/0271* (2013.01); *C12Q 1/6886* (2013.01); *G01N 33/5067* (2013.01); *G01N 33/57438* (2013.01); *A01K 2207/12* (2013.01); *A01K 2227/105* (2013.01); *C12N 2503/02* (2013.01); *C12N 2513/00* (2013.01); *C12Q 2600/158* (2013.01); *C12Y 305/01098* (2013.01)

(58) Field of Classification Search
CPC .............. C12N 5/0693; C12N 2513/00; C12N 2503/02; G01N 33/5067; G01N 33/57438; C12Q 2600/158; C12Q 1/6886
See application file for complete search history.

(56) References Cited

U.S. PATENT DOCUMENTS

2008/0248570 A1* 10/2008 Turner ................. C12N 5/0671
435/377

OTHER PUBLICATIONS

Cao et al. Sphere-forming cell subpopulations with cancer stem cell properties in human hepatoma cell lines. Cao et al. BMC Gastroenterology 2011, 11:71, p. 1-11 (Year: 2011).*
Yamashita et al. EpCAM-Positive Hepatocellular Carcinoma Cells Are Tumor-Initiating Cells With Stem/Progenitor Cell Features. Gastroenterology 2009;136:1012-1024 (Year: 2009).*
Yan et al. Establishment of NOD/SCID mouse models of human hepatocellular carcinoma via subcutaneous transplantation of histologically intact tumor tissue. Chin J Cancer Res 2013;25(3):289-298 (Year: 2013).*
Villasante et al. Tissue-engineered models of human tumors for cancer research. Expert Opin Drug Discov. Mar. 2015; 10(3): 257-268. published online on Feb. 7, 2015 (Year: 2015).*
Yang et al. The Tumor Microenvironment in Hepatocellular Carcinoma: Current Status and Therapeutic Targets. Semin Cancer Biol. Feb. 2011 ; 21(1): 35-43 (Year: 2011).*
Zhang et al. Synergistic Inhibition of Hepatocellular Carcinoma Growth by Cotargeting Chromatin Modifying Enzymes and Poly (ADPribose) Polymerases. Hepatology. Jun. 2012 ; 55(6): 1840-1851 (Year: 2012).*
Subbiah et al. Targeted therapies in early-phase trials for the treatment of advanced fibrolamellar hepatocellular carcinoma. Journal of Clinical Oncology 31, No. 4_suppl (Feb. 1, 2013) Abstract. p. 1-3 (Year: 2013).*
Cornella et al. Unique Genomic Profile of Fibrolamellar Hepatocellular Carcinoma. Gastroenterology 2015;148:806-818 (Year: 2015).*
Fujii, E et al. "Establishment and Characterization of In Vivo Human Tumor Models in The NOD/SCID/Gamma(s)(null)Mouse." Pathol Int. Sep. 2008, 58(9); 559-67. Abstract.
International Search Report dated Jul. 27, 2016 in International Application No. PCT/US2016/020925.
Li, CY et al. "Micropatterned Cell—Cell Interactions Enable Functional Encapsulation of Primary Hepatocytes in Hydrogel Microtissues." 2014. Tissue Engineering: Part A, vol. 20, Nos. 15 and 16.
Malouf, GG. "Transcriptional Profiling of Pure Fibrolamellar Hepatocellular Carcinoma Reveals an Endocrine Signature." Jun. 2014. Hepatology, 59(6):2228-2237.
Oikawa, T et al. "Human Fibrolamellar Hepatocellular Carcinomas: Evidence for Their Derivation from Biliary Tree Stem Cell Subpopulations." 2013. Stem Cell Biology. Hepatology, 58: 1001A-1010A.
Oikawa, T et al. "Model of Fibrolamellar Hepatocellular Carcinomas Reveals Striking Enrichment in Cancer Stem Cells." Oct. 6, 2015. Nat Commun, 6:8070.
Oikawa, T et al. "Sal-like Protein 4 (SALL4), A Stem Cell Biomarker in Liver Cancers." Apr. 2013. Hepatology. vol. 57, No. 4.
Xu, L et al. "Genomic Analysis of Fibrolamellar Hepatocellular Carcinoma. " Jan. 1, 2015. Hum Mol Genet, 24(1); 50-63.
Zhou, Y et al. "TCF7L2 is A Master Regulator of Insulin Production and Processing." Dec. 15, 2014. Hum Mol Genet, 23(24): 6419-6431.
International Preliminary Report on Patentability issued in related International Patent Application No. PCT/US2016/020925, dated Sep. 21, 2017.

(Continued)

Primary Examiner — Taeyoon Kim
(74) Attorney, Agent, or Firm — Foley & Lardner LLP

(57) ABSTRACT

The present disclosure provides a model of human fibrolamellar hepatocellular carcinoma (FL-HCC) cells maintained as a transplantable tumor line in a host and a method to establish a transplantable human FL-HCC tumor line. Methods of ex vivo cultures of the FL-HCC are provided. Methods of diagnosing and treating FL-HCC tumors are also provided.

10 Claims, 28 Drawing Sheets

Specification includes a Sequence Listing.

(56) References Cited

OTHER PUBLICATIONS

Kern et al., "Ex vivo analysis of antineoplastic agents in precision-cut tissue slices of human origin: effects of cyclooxygenase-2 inhibition in hepatocellular carcinoma," *Liver International*, vol. 26, pp. 604-612 (2006).
Toberson, "Fibrolamellar Carcinoma," *Scientifica*, vol. 2012, 15 pages (2012).
European Extended Search Report issued in co-pending European Patent Application No. 16762222.4, dated Oct. 22, 2018.
Foreign Action other than Search Report on Taiwan Patent Application No. 105106887, dated Jun. 2, 2020.
Graham et al., "DNAJB1-PRKACA is Specific for Fibrolamellar Carcinoma", Modern Pathology, vol. 28, pp. 822-829 (2015).
Honeyman et al., "Detection of a recurrent DNAJB1-PRKACA Chimeric Transcript in Fibrolamellar Hepatocellular Carcinoma", *Science*, vol. 343, No. 6174, pp. 1010-1014 (Feb. 2014).
Patonai, et al., "Molecular Characteristics of Fibrolamellar Hepatocellular Carcinoma", Pathology Oncology Research, vol. 19, No. 1, pp. 63-70 (Aug. 2012).
Foreign Action other than Search Report on EP 16762222.4 dated Jan. 11, 2021.
Malouf, et al., "Transcriptional profiling of pure fibrolamellar hepatocellular carcinoma reveals an endocrine signature", Hepatology, vol. 59, No. 6, pp. 2228-2237 (Jun. 2014).
Riggle et al., "Neurotensin Enhances Hepatocyte Proliferation in Fibrolamellar Hepatocellular Carcinoma", Journal of The American College of Surgeons, vol. 221, No. 4, p. S143 (Oct. 2015).
Vivekanandan, et al., "Anterior gradient-2 is overexpressed by fibrolamellar carcinomas", Human Pathology, vol. 40, No. 3, pp. 293-299 (Mar. 2009).
Lim, IIP et al., "Advances in Fibrolamellar Hepatocellular Carcinoma: A Review", *Eur J Pediatr Surg.*, vol. 24, No. 6, pp. 461-466, (Dec. 2014).
Office Action issued in Canadian Patent Application No. 2,978,729, dated Feb. 18, 2022.

* cited by examiner

| IHC assays on section from original blocks of FL-HCC samples | | | | | | | | |
|---|---|---|---|---|---|---|---|---|
| RKCC sample | | G | Age | BMI1 | SOX9 | PDX1 | SHH | HepPar-1 |
| 00-2235 | 7T | F | 52 | − | − | + | ++ | + |
| 00-36089 | T5 | F | 39 | + | + | − | ++ | + |
| 10-4006 | ILN1 | M | 39 | + | + | + | ++ | n.d |
| 06-20570 | T2/U5 | M | 48 | + | + | + | ++ | + |
| 02-1266 | U1 | F | 19 | − | + | + | ++ | n.d |
| 10-7763 | 2U | M | 34 | + | + | + | ++ | + |
| 04-5864 | 12T | F | 16 | − | − | − | ++ | + |
| 11-15017 | 5QLN | F | 18 | − | + | + | ++ | n.d |
| 04-4613 | 3T | M | 22 | − | + | + | ++ | n.d |
| Totals | | | | 4/9 | 7/9 | 7/9 | 9/9 | 5/5 |

G = Gender, age at first diagnosis or age at time of recurrence. ++ = positive in most of the cells but with heterogeneous levels of expression, + = heterogeneous expression with a percentage positive (at least 20%) and the rest negative, − = negative in all of the cells, n.d = not done

Figure 7

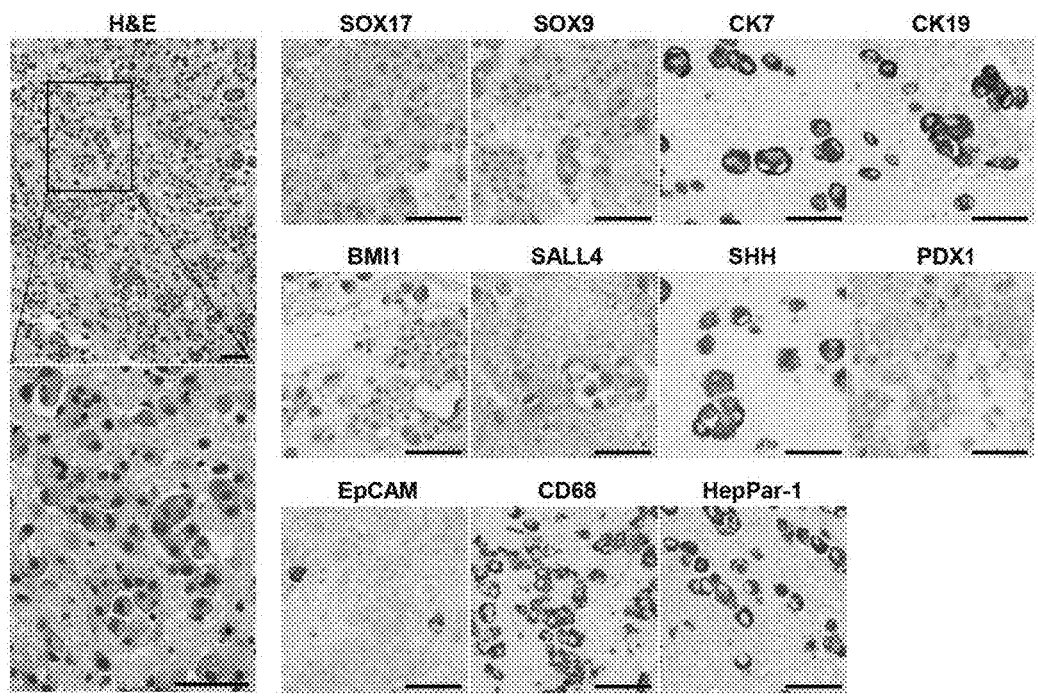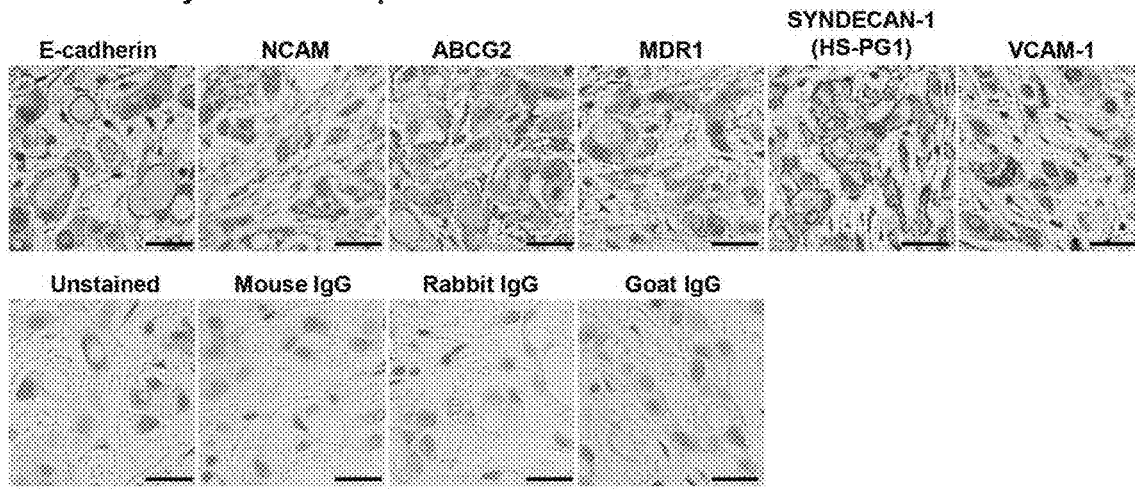
Figure 9 a. Original hFL-HCC cells on plastic and in kubota's medium (KM)
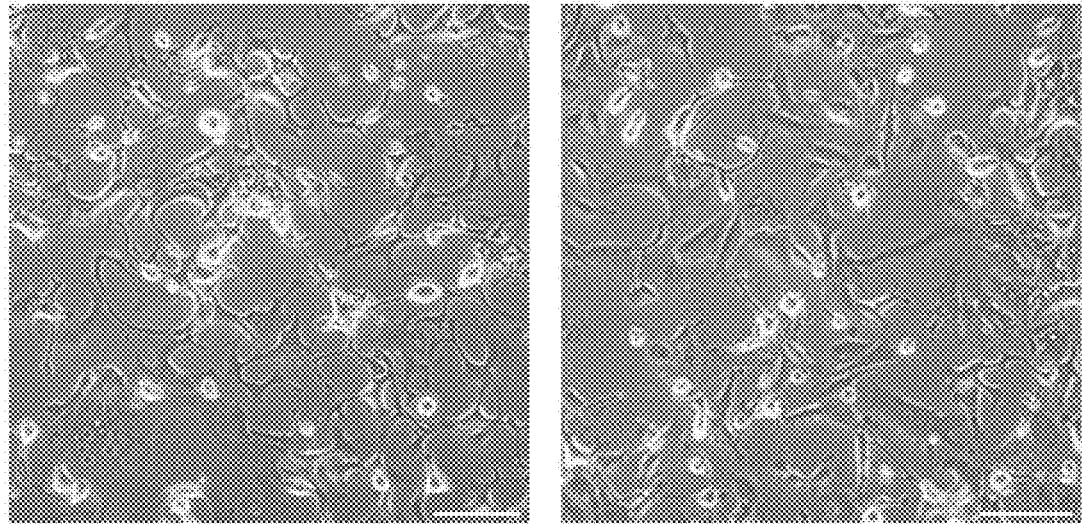
b. Unsorted FL-HCC cells from xenotransplantable tumor on plastic and in KM
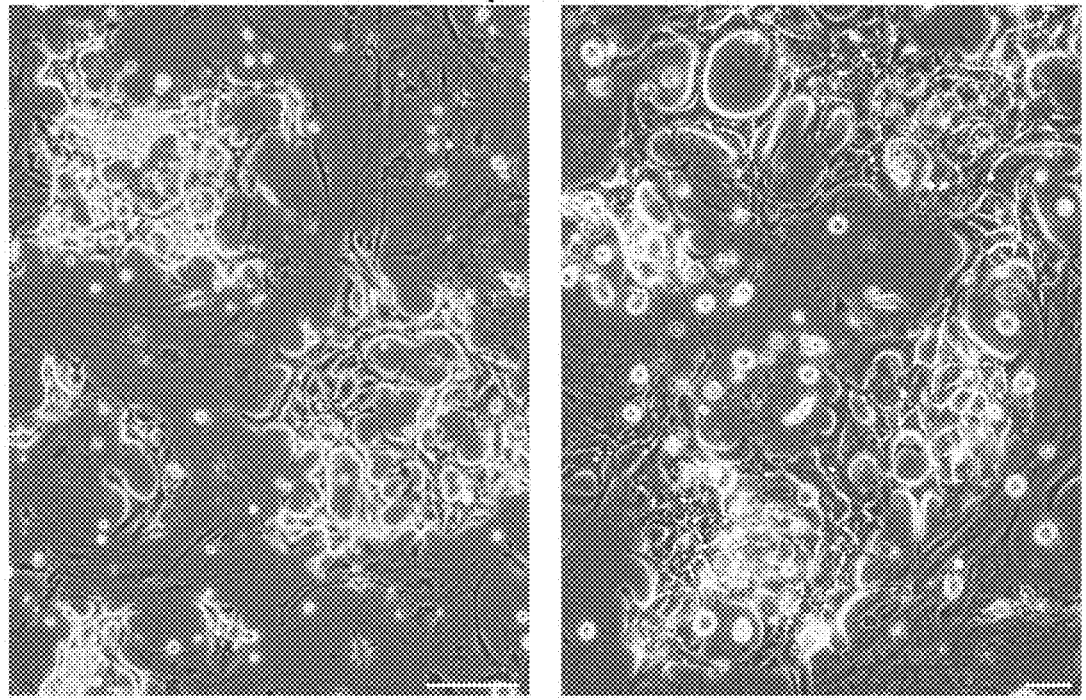
Figure 10

IPA analysis

| FL-HCC vs. BTSC (n=1692) | FL-HCC vs. HPSC (n=1783) | BTSC vs. HPSC (n=248) |
|---|---|---|
| FXR/RXR Activation (2.15E-11) | Coagulation System (3.98E-10) | FXR/RXR Activation (7.94E-30) |
| LXR/RXR Activation (4.17E-08) | Acute Phase Response Signaling (8.32E-10) | LXR/RXR Activation (2.00E-22) |
| Acute Phase Response Signaling (9.12E-08) | LXR/RXR Activation (8.71E-09) | Coagulation System (1.00E-18) |
| LPS/IL-1 Mediated Inhibition of RXR Function (1.45E-07) | Hepatic Fibrosis / Hepatic Stellate Cell Activation (8.32E-08) | Acute Phase Response Signaling (3.98E-18) |
| Axonal Guidance Signaling (2.69E-07) | FXR/RXR Activation (1.10E-07) | Atherosclerosis Signaling (7.94E-14) |
| Granulocyte Adhesion and Diapedesis (3.02E-07) | LPS/IL-1 Mediated Inhibition of RXR Function (2.14E-07) | Extrinsic Prothrombin Activation Pathway (7.24E-10) |
| Role of Tissue Factor in Cancer (1.02E-06) | Nicotine Degradation II (8.13E-05) | Clathrin-mediated Endocytosis Signaling (4.27E-08) |
| Hepatic Cholestasis (2.88E-06) | Axonal Guidance Signaling (8.91E-05) | IL-12 Signaling and Production in Macrophages (7.94E-08) |
| Leukocyte Extravasation Signaling (4.57E-06) | Serotonin Degradation (1.00E-04) | Intrinsic Prothrombin Activation Pathway (1.07E-06) |
| Xenobiotic Metabolism Signaling (7.42E-06) | Atherosclerosis Signaling (1.66E-04) | Complement System (2.43E-06) |
| Atherosclerosis Signaling (8.71E-06) | Thyroid Hormone Metabolism II (via Conjugation and/or Degradation) (1.70E-04) | Production of Nitric Oxide and Reactive Oxygen Species in Macrophages (6.46E-05) |

Top 10 results for IPA analysis. Gene lists for IPAs are DE expressed from DESeq (FDR P<0.05) and average expression in one of the disease categories > 50. BTSC vs. HPSC only lists 9 because the rest of the results are just from the same two genes (see IPA output spreadsheet).

Figure 17

SEQUENCE LISTING

<160> NUMBER OF SEQ ID NOS: 28

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgccgctttg caggtgtat                                                 19

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggcctccgtc cgagaga                                                   17

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcacagtcac tgacaccaac ga                                             22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcacctgac ccttgtacgt                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaaggccag cgttgtctcc                                                20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgaagccagc tctctatccc a                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgctgcctac atgagcaagg t                                           21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tctgtcaact ccgtctcatt gag                                         23

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcccgctacg ccctaca                                                17

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgactcaagg tgcagcagga t                                           21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgcgactac agccactact                                             20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtcgatctgc aggacaatcc                                             20

```
<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaggatctgg tgagcctgag aa                                            22

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cataagtgat gctggagctg gtaa                                          24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaatctaaga ggtggcagaa aaaca                                         25

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cttctgcgtc acaccattgc                                               20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccatggatg aagtctacc                                                19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtcctcctcc tttttccac                                                19
```

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gagaggcaac ctggagaatt tg                                              22

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gatctgctgc agtgtgggtt t                                               21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tccacagaaa tttacctaca ttgg                                            24

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cagcagagag cagatgacca                                                 20

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaatgggagg ggtgcaaaag aggag                                           25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagctgtcat ttgctgtggg tgatg                                           25

<210> SEQ ID NO 25

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25 gactttttgcc gcagctcagg aag                                          23

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccagctttg agcaaatgac agtattttg                                     29

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaggtgaagg tcggagtcaa                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aatgaagggg tcattgatgg                                               20
```

HUMAN FIBROLAMELLAR HEPATOCELLULAR CARCINOMAS (HFL-HCCS)

CROSS-REFERENCE TO RELATED PATENT APPLICATIONS

This application is a continuation of U.S. patent application Ser. No. 15/061,626, filed Mar. 4, 2016, which claims priority from U.S. Provisional Patent Application No. 62/129,668, filed Mar. 6, 2015. These applications are incorporated herein by reference in their entirety.

GOVERNMENT SUPPORT

This invention was made with government support under federal NIH grant R00DK091318-02, awarded by the National Institutes of Health. The government has certain rights in the invention.

BACKGROUND

Human fibrolamellar hepatocellular carcinomas (hFL-HCCs) are rare cancers accounting for less than ~5% of all liver cancers and unique in being found primarily in children to young adults without evidence of fibrosis or cirrhosis. The epidemiological factors are unknown, as are causes of increases in occurrence in hFL-HCCs over the past 60 years. These malignances are currently treatable only by surgery, as all tested forms of chemotherapy and external radiation therapy have proven ineffective. Even surgery is ineffective if the hFL-HCC tumor has metastasized. In addition, molecular mechanisms of hFL-HCCs have been difficult to study, since investigations have had to be conducted on freshly isolated tissue or paraffin sections—samples that are difficult to obtain. Therefore, a need exists for in vivo models of hFL-HCCs, such as transplantable tumor lines, and/or in vitro models of hFL-HCCs, such as cell lines or spheroid cultures, for use in defining the disease as well as identifying novel strategies for treating hFL-HCCs.

SUMMARY

Aspects of the disclosure relate to transplantable tumor lines of human fibrolamellar hepatocellular carcinoma (hFL-HCC) cells maintained in a non-human animal. In some aspects, the transplantable tumor line comprises hFL-HCC cells and mesenchymal cells from a non-human host. Also disclosed is a composition comprising hFL-HCC cells and an amount of non-human mesenchymal cells effective to sustain the viability of said hFL-HCC cells.

Other aspects of the disclosure provide cell cultures comprising hFL-HCC cells in a serum-free medium.

Further aspects provide methods for establishing a hFL-HCC tumor line comprising: (a) obtaining a hFL-HCC tumor from a patient with a FL-HCC; (b) preparing a tumor cell suspension from the FL-HCC tumor; (c) culturing the tumor cell suspension under restrictive conditions that select for cancer stem cells to obtain a population of culture-selected cancer stem cells; and (d) transplanting culture-selected cells into an immunocompromised, non-human animal.

Aspects of the disclosure also relate to methods for maintaining a hFL-HCC transplantable tumor line comprising: (a) obtaining hFL-HCC cells from a xenografted tumor of a first immunocompromised non-human animal; (b) dispersing the hFL-HCC cells into a cell suspension by enzymatic or mechanical methods; and (c) transplanting dispersed hFL-HCC cells into a second immunocompromised, non-human animal.

Additional aspects provide methods for culturing hFL-HCC cells comprising: (a) separating hFL-HCC cells of a xenografted tumor from non-human cells; (b) suspending the separated hFL-HCC cells in a serum-free medium; and (c) plating the hFL-HCC cells onto or into a culture substratum to obtain plated hFL-HCC cells.

Additional aspects provide methods for culturing hFL-HCC cells comprising: (a) separating hFL-HCC cells of a xenografted tumor from non-human cells; (b) suspending the separated hFL-HCC cells in a serum-free medium; and (c) allowing the cells to form floating aggregates (e.g. spheroids or organoids) in a culture medium.

In some aspects herein provided are methods for drug screening, comprising (a) introducing a candidate drug to cultured hFL-HCC cells that are in the form of monolayers, hydrogels, spheroids, or organoids and (b) monitoring the effect of the candidate drug on the cultured hFL-HCC cells.

In some aspects herein provided are methods for drug testing, comprising (a) administering a candidate drug to a non-human animal carrying a transplantable hFL-HCC tumor and (b) monitoring the effect of the candidate drug on the xenotransplanted hFL-HCC tumor.

In some aspects herein provided are methods for suppressing the growth of hFL-HCC cells, comprising treating the hFL-HCC cells with a drug, an immunotherapy, or an inhibitor to a specific signaling pathway. Non-limiting examples include a hedgehog signaling pathway inhibitor, a histone deacetylase inhibitor and/or an inhibitor to one or more protein kinases. Some specific examples include, inhibitor of CA12 such as Acetazolamide, and/or anti-sense oligonucleotides to SLC16A14 to minimize its effects conferring drug resistance, which is relevant to hFL-HCC, a cancer that is highly chemo- and drug-resistant.

Further aspects provide methods for treating hFL-HCC in a patient in need thereof, comprising administering to the patient an effective amount of drug, with immunotherapy, with an inhibitor to a specific signaling pathway. Non-limiting examples include a hedgehog signaling pathway inhibitor, a histone deacetylase inhibitor and/or an inhibitor to one or more protein kinases.

In yet other aspects herein provided are methods of determining whether a patient has fibrolamellar hepatocellular carcinoma (FL-HCC), comprising: (a) measuring gene expression levels of at least one of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, and TNRC6C; and (b) comparing the gene expression profile to one or more control samples.

In yet other aspects herein provided are methods of determining whether a patient has fibrolamellar hepatocellular carcinoma (FL-HCC), comprising: (a) measuring gene expression levels of at least one or more genes of a set of genes found to constitute a genetic signature for hFL-HCCs and that include C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, and TNRC6C from a sample collected from a patient suspected of having a biliary tree or liver tumor; and (d) comparing the gene expression profile to one or more control samples, wherein the sample collected from the patient has histological features typical for FL-HCC and/or expresses the DNAJB1-PRKACA fusion gene.

In yet other aspects herein provided are methods of treating a patient determined to have hFL-HCC by administering to the patient an effective amount of at least one therapeutic that decreases expression of at least one gene in a set found to be a genetic signature for hFL-HCCs and that include C10orf128, CA12, CREB3L1, GALNTL6, IRF4, ITPRIP, KCNE4, NOVA1, OAT, PAK3, PCSK1, PHACTR2, RPS6KA2, SLC16A14, TMEM1163, or TNRC6C.

In yet other aspects herein provided are methods of treating a patient determined to have hFL-HCC by administering to the patient an effective amount of an immunotherapy.

In yet other aspects herein provided are methods of treating a patient determined to have hFL-HCC by administering to the patient an effective amount of at least one therapeutic that regulates PRKACA or SRC network hubs.

In yet other aspects herein provided are methods of treating a patient determined to have hFL-HCC by administering to the patient an effective amount of at least one therapeutic that regulates substrate targets of the kinase PRKACA (Protein kinase A catalytic subunit alpha).

In another aspect are provided compositions of isolated hFL-HCC cells wherein the hFL-HCC cell expresses at least one marker selected from the group consisting of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, and TNRC6C.

In yet other aspects, are provided herein, populations of isolated hFL-HCC cells wherein the hFL-HCC cell expresses a marker selected from the group consisting of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, and TNRC6C.

In still yet other aspects provided herein are compositions comprising isolated hFL-HCC cells wherein the hFL-HCC cell expresses a marker selected from the group consisting of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, and TNRC6C and a carrier.

One embodiment of the disclosure described herein relates to a specific transplantable human tumor line, TU-2010, consisting of hFL-HCC tumor cells and large numbers (>50% of the cells in the tumor) of mesenchymal cells of the non-human host.

In some embodiments, the non-human animal is immunocompromised. In some embodiments, the non-human animal is a mouse, for example, a NOD scid gamma (NSG) mouse.

In some embodiments, the hFL-HCC cells are derived from liver, from biliary tree, from a subcutaneous or intraperitoneal tumor, for example, ascites tumor cells.

In some embodiments, the tumor line comprises hFL-HCC cells and mesenchymal cells of the non-human animal. In some embodiments, at least 50% of the hFL-HCC cells in the transplantable tumor are cancer stem cells.

In some embodiments, the hFL-HCC cells express the fusion transcript DNAJB1-PRKACA. In other embodiments, the hFL-HCC cells substantially do not express HDAC9 or express a lower level of HDAC9 as compared to a human non-FL-HCC cell control sample.

In some embodiments, the hFL-HCC cells express one or more markers of endodermal transcription factors selected from the group consisting of SOX9, SOX17, PDX1, FOXA1, and NGN3.

In some embodiments, the hFL-HCC cells express one or more markers of pluripotency genes selected from the group consisting of OCT4, SOX2, NANOG, KLF4, SALL4 and KLF5.

In some embodiments, the hFL-HCC cells express one or more markers of other stem cell genes selected from the group consisting of CD44, SALL4, TROP-2, BMI-1, sonic hedgehog (SHH), LGR5, NCAM, and KRT20.

In some embodiments, the hFL-HCC cells express one or more hepatic markers selected from the group consisting of CK8, CK18, CK19, DCLK1, HepPar-1, albumin, alpha-fetoprotein, and CD68.

In some embodiments, the hFL-HCC cells express one or more pancreatic markers selected from PDX1, NGN3, PCSK1, insulin, glucagon, amylase, and mucin (MUC).

In some embodiments, the hFL-HCC cells express high levels of aryl hydrocarbon receptors (AHR).

In some embodiments, the hFL-HCC cells express biomarkers of malignancy such as AGR2 and/or high levels of extracellular matrix-degrading enzymes and/or aberrations in the regulation of p53.

In some embodiments, the hFL-HCC cells have aberrant or lack of expression of one or more histone deacetylase (HDAC) genes.

In some embodiments, the tumor is a xenotransplanted, subcutaneous or intraperitoneal tumor.

In some embodiments, at least 30% of the hFL-HCC cells are cancer stem cells (CSCs). In other embodiments, at least 50% of the hFL-HCC cells are CSCs. In yet other embodiments, at least 65% of the hFL-HCC cells are CSCs. In still other embodiments, at least 51% of the cells in the cell culture are hFL-HCC cells.

In some embodiments, provided herein is a tissue sample obtained from the tumor line of any one of the above embodiments.

In some embodiments, the serum-free medium is Kubota's Medium. In some embodiments, the serum-free medium contains hyaluronans, HGF and/or VEGF.

In some embodiments, at least a portion of the hFL-HCC cells are in aggregates (e.g. spheroids) of hFL-HCC cells. In other embodiments, at least a portion of the hFL-HCC cells are in organoids comprised of hFL-HCCs and associated mesenchymal cells (e.g. endothelia, stellate cells, stromal cells).

In some embodiments, the hFL-HCC tumor is obtained as an ascites fluid or as a solid tumor from the subject.

In some embodiments, the tumor cell suspension from the hFL-HCC tumor are cultured on tissue culture plastic, on hyaluronans, or in hyaluronan hydrogels.

In some embodiments, the tumor cell suspension from the hFL-HCC tumor are cultured in serum-free Kubota's Medium.

In some embodiments, the methods provided herein comprise transplanting subcutaneously or intraperitoneally the culture-selected cancer stem cells from the hFL-HCC cells into the immunocompromised non-human animal.

In some embodiments, the methods provided herein comprise transplanting about $10^2$ to about $10^7$ culture-selected cancer stem cells from the hFL-HCC tumor into the immunocompromised, non-human animal.

In some embodiments, the methods provided herein further comprise monitoring the immunocompromised, non-human animal for tumor formation for about 2 to about 9 months In some embodiments, the methods provided herein further comprise transplanting subcutaneously or intraperitoneally the hFL-HCC tumor into the second immunocompromised, non-human animal.

In some embodiments, the methods provided herein comprise separating hFL-HCC cells from non-human cells by immunoselection, for example, magnetic immunoselection.

In some embodiments, the culture substratum is tissue culture plastic, a 2D monolayer or 3D hydrogel of a purified extracellular matrix component. In some embodiments, the purified extracellular matrix component is selected from the group consisting of hyaluronan, a collagen, an adhesion molecule, and an extract enriched in extracellular matrix. In some embodiments, the adhesion molecule is laminin. In other embodiments, the extract enriched in extracellular matrix is a biomatrix scaffold or Matrigel. In some embodiments, the matrix scaffold is prepared by protocols for decellularized tissue. In other embodiments, the matrix scaffold is prepared from high salt decellularization protocols, such as biomatrix scaffolds.

In some embodiments, the plated hFL-HCC cells are kept in suspension and allowed to form aggregates, for example, spheroids (only the hFL-HCC cells) or organoids (mixtures of hFL-HCC cells and mesenchymal cells (endothelia, stellate cells, stromal cells).

In some embodiments, the hedgehog signaling pathway inhibitor comprises GDC-0449.

In some embodiments, the histone deacetylase inhibitor comprises suberoylanilide hydroxamic acid (SAHA) and/or suberic bis-hydroxamic acid (SBHA).

In some embodiments, overexpression of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163 or TNRC6C relative to the control sample is associated with presence of hFL-HCC. In some embodiments, overexpression of PCSK1, CA12, NOVA1, SLC16A14, TNRC6C, TMEM163, and RPS6KA2 relative to the control sample is associated with presence of hFL-HCC. In other embodiments, overexpression of C10orf128, OAT, PAK3, PCSK1, PHACTR2, SLC16A14, TMEM163, and TNRC6C relative to the control sample is associated with presence of hFL-HCC. In some embodiments, the hFL-HCC also expresses the fusion gene DNAJB1-PRKACA.

In some embodiments, the control sample is selected from the group consisting of hepatocellular carcinomas (HCCs), hepatoblastomas, cholangiocarcinomas (CCAs), pancreatic cancers, other types of cancers as well as normal cells that include biliary tree stem cells, hepatic stem cells, hepatoblasts, pancreatic stem cells, hepatic or pancreatic committed progenitors, and mature liver or pancreatic cells.

In some embodiments, the at least one therapeutic is selected from the group consisting of a small molecule, RNA interference, and a locked nucleic acid (LNA). Alternatively, at least one therapeutic is selected from a form of immunotherapy.

These and other features, together with the organization and manner of operation thereof, will become apparent from the following detailed description when taken in conjunction with the accompanying drawings.

Abbreviations and Terminology

Acronyms for cell populations are preceded by a small letter to indicate the species: m=murine; h=human. ABCG2 (or CDw338), ATP-binding cassette sub-family G member 2 that confers drug resistance; Acetazolamide, an inhibitor of carbonic anhydrases; AFP, α-fetoprotein; ALB, albumin; Basal Media, buffers comprised of amino acids, minerals, sugars, lipids, vitamins and other nutrients in a composition mimicking interstitial fluid and used for cell culture; BMi-1, B lymphoma Mo-MLV insertion region 1 homolog that is an oncogene conferring the ability of self-replication of cells; BTSCs, biliary tree stem cells; CA12, carbonic anhydrase 12, a zinc metallo enzyme; C1orf128, Chromosome 10 open reading frame 128; CCA, cholangiocarcinoma; CD, common determinant; CD13, alanine aminopeptidase; CD44, hyaluronan receptors; CD133, prominin; CFTR, cystic fibrosis transmembrane conductance regulator; CK, cytokeratin protein; CREB3L1, the cAMP responsive element binding protein 3-like 1; CSCs, cancer stem cells; CXCR4, CXC-chemokine receptor 4 (also called fusin or CD184); EGF, epidermal growth factor; EpCAM, epithelial cell adhesion molecule; FBS, fetal bovine serum; FGF, fibroblast growth factor; FLC, fibrolamellar carcinoma (synonym=FL-HCC, fibrolamellar hepatocellular carcinoma); GALNT6, polypeptide N-acetyl-galactos-aminyl-transferase-like 6 that participates in 0-glycan biosynthesis; GDC-0449, inhibitor of hedgehog signaling pathway via hedgehog surface receptors (PTCH, SMO); HDAC, histone deacetylase; HDM, a serum-free medium comprised of basal media and a defined mix of purified hormones, growth factors and nutrients tailored for a specific cell or biological process; HDM-C, a hormonally defined medium for cholangiocytes; HDM-H, a hormonally defined medium for hepatocytes; HDM-P, a hormonally defined medium for pancreatic islets; hFL-HCC, human fibrolamellar hepatocellular carcinoma; HBs, hepatoblasts; HCC, hepatocellular carcinoma; HGF, hepatocyte growth factor; HpSCs, hepatic stem cells; IRF4, Interferon regulatory factor 4. Transcriptional activator; ITPRIP, inositol 1,4,5-trisphosphate receptor-interacting protein; KCNE4: Potassium voltage-gated channel subfamily E, member 4 modulates the multimeric channel complex. KM, Kubota's Medium, a serum-free, hormonally defined medium designed for endodermal stem/progenitors; KRT, cytokeratin gene; LGR5, Leucine-rich repeat-containing G-protein coupled receptor 5 that binds to R-spondin; NANOG, a transcription factor critically involved with self-renewal; NCAM, neural cell adhesion molecule; NOVA-1, Neuro-oncological ventral antigen 1NSG, nod scid gamma (species of immunocompromised mouse); OAT, ornithine aminotransferase; ORGANOID, floating aggregate of cells comprised of both epithelia and mesenchymal cells; PAK3, Sernie/threonine-proteni kinase PAR 3; PCSK1, proprotein convertase 1 involved in processing of hormones; PDX1, pancreatic and duodenal homeobox 1; PBGs, peribiliary glands, stem cell niches for biliary tree stem cells; PDX, patient-derived xenograft; PHACTR2, phosphatase and actin regulator 2; RPS6KA2 Ribosomal protein S6 kinase alpha-2; SBHA, suberic bis-hydroxamic acid; SAHA, suberoylanilide hydroxamic acid (potent, reversible class I and II HDAC inhibitor); SALL4, Sal-like protein 4; SLC16A14: membrane channel for solute carrier family 16 (monocarboxylic acid transporters), member 14; SOX, Sry-related HMG box; SPHEROID, floating aggregate of cells that are only one cell type; TCGA, The Cancer Genome Atlas; TEM, transmission electron microscopy; TMA, tissue microarrays; TMEM163, Transmembrane protein 163 involved in zinc transport and homeostasis; TNRC6C, Trinucleotide repeat-containing gene 6C protein involved in gene regulation; TROP-2, tumor-associated calcium signal transducer 2; VEGF, vascular endothelial cell growth factor.

BRIEF DESCRIPTION OF THE DRAWINGS

The patent or application file contains at least one drawing executed in color. Copies of this patent or patent application publication with color drawing(s) will be provided by the Office upon request and payment of necessary fee.

FIG. 7 shows the results of IHC assays on paraffin sections of the original blocks. The IHC assays on paraffin sections of hFL-HCCs from 9 donors indicated that all are positive for sonic hedgehog (SHH) and, of those assayed, all were also positive for HepPar-1. The majority of the tumors (7/9) were positive for SOX9 and PDX1, and 4/9 for BMI1. There were two distinct patterns of expression comprised of 1) ones in which most were positive for a given antigen (e.g. HepPar1, SHH, and SOX9) but with heterogeneous levels of expression or 2) a pattern in which a percentage of the cells were positive (at least 20%) and the remainder negative (e.g. PDX1 and BMI1).

FIG. 9 shows the results of IHC assays of the original tumor (ascites) versus the xenotransplantable tumor, TU-2010. (a) Cytology and IHC assays on cytospun ascites tumor cells. Cytology revealed small aggregates of tumor cells with large pleomorphic nuclei and some forming partial ductular structures. The IHC assays on TU-2010 indicated strong positivity for endodermal stemness markers (SOX17, SOX9, PDX1, SALL4, and BMI1), hepatic markers (HepPar-1, CK7 and CK19), and CD68. The scale bar=50 μm. (b) Additional IHC assays of the xenotransplantable tumor. In addition to the assays shown in FIG. 3, other markers found to be strongly positive included E-cadherin, NCAM, two forms of multidrug resistance genes (MDR1 and ABCG2), syndecan1 (heparan sulfate proteoglycan-1 or HS-PG-1), and VCAM-1. Controls for the IHC assays are also provided. The scale bar=25 μm.

FIG. 10 shows images of monolayer cultures of the original (a) hFL-HCC cells versus the (b) xenotransplanted tumors of TU-2010. These are of unsorted cells and, therefore, a mixture of host (murine) mesenchymal cells and the tumor cells. The scale bar=100 μm.

FIG. 17 shows the results of pathway enrichment analysis. Results of ingenuity pathway analysis (IPA) are shown for genes significantly differentially expressed between hFL-HCCs from TU-2010 and hBTSCs, hFL-HCCs and hHpSCs, and hBTSCs and hHpSCs.

DETAILED DESCRIPTION

Figure 1:
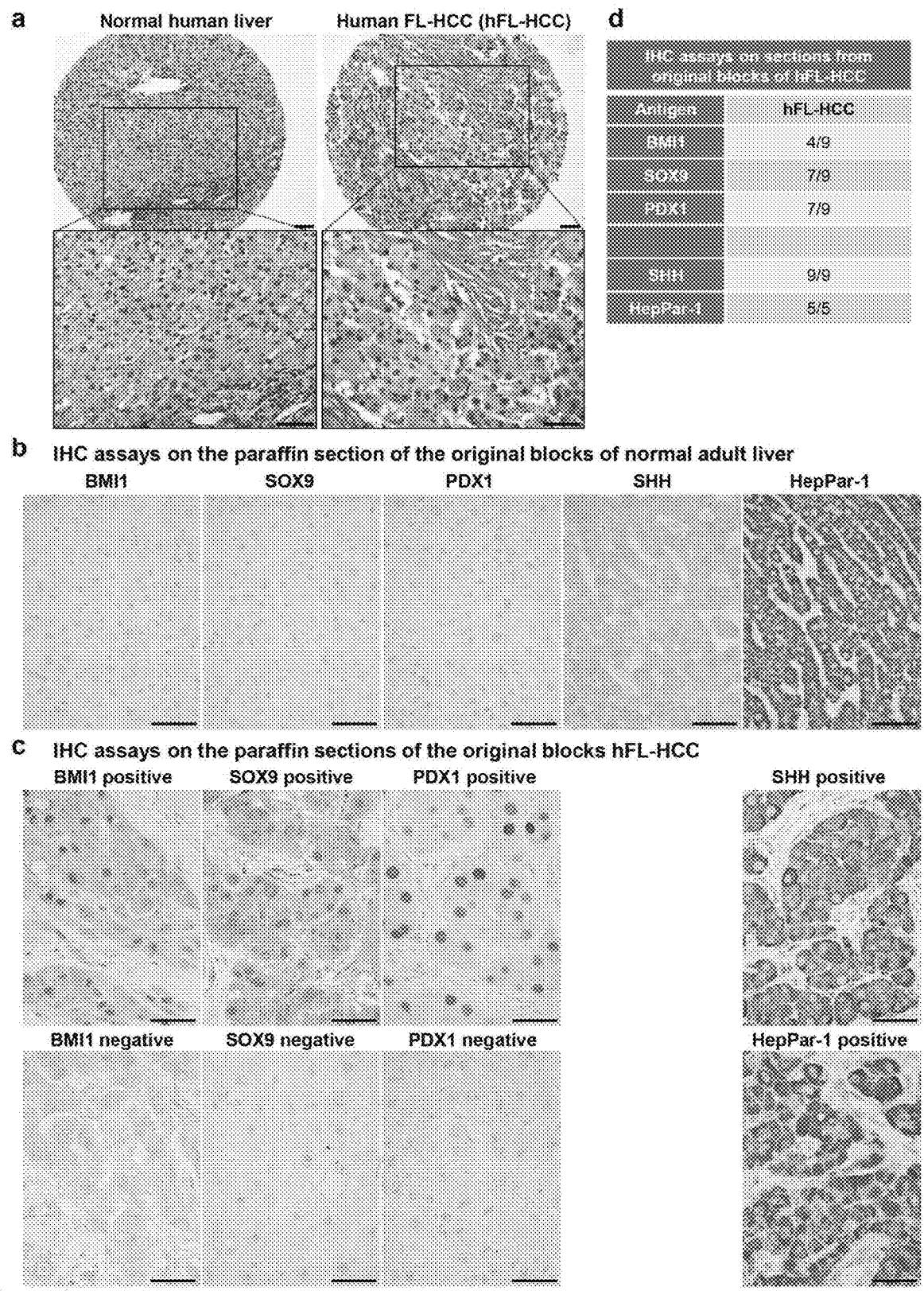
FIG. 1 shows the analysis of human FL-HCCs compared to normal adult livers using tissue microarrays (TMAs) and immunohistochemistry (IHC) assays. (a) Hematoxylin/eosin stained paraffin sections of TMAs. (b, c) Representative IHC assays on sections from the original blocks of normal adult liver versus hFL-HCC tumors. (d) Complete results of IHC assays. Additional details are given in FIG. 7. The scale bar is 50 μm (a), 25 μm (b-c).

Fibrolamellar carcinomas (FLCs), also referred to as fibrolamellar hepatocellular carcinomas (FL-HCC), occur primarily in children and young adults without evidence of any chronic disease. FLCs were recognized only recently, within the last approximately 45 years, but now account for approximately 1-5% of liver cancers worldwide. The epidemiological factors remain unknown. To date, FLCs are treatable only by surgery, which however is unproductive if there is metastatic disease at the time of diagnosis. Other forms of therapy, such as chemo- and external radiation therapies, or specific drugs commonly used for hepatocellular carcinomas (HCCs), have proven ineffective for FLCs. The average time to death post-diagnosis for FLC patients is only about 18 months. This disclosure is related to tools for studying the disease (e.g., a transplantable tumor line), including drug screening and testing, as well as methods of suppressing the growth of fibrolamellar hepatocellular carcinomas (FL-HCC).

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined by below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

Definitions

As used herein, the singular terms "a," "an," and "the" include plural referents unless the context clearly dictates otherwise. Thus, for example, reference to a cell can include multiple cells unless the context clearly dictates otherwise.

The term "about," as used herein when referring to a measurable value such as an amount or concentration (e.g., the percentage of collagen in the total proteins in the biomatrix scaffold) and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

Also as used herein, "and/or" refers to and encompasses any and all possible combinations of one or more of the associated listed items, as well as the lack of combinations when interpreted in the alternative ("or").

As used herein, the term "aggregates" refer to a plurality of cells that are amassed together. The aggregates may vary in both size and shape or may be substantially uniform in size and/or shape. The cell aggregates used herein can be of various shapes, such as, for example, a sphere, a cylinder (preferably with equal height and diameter), or rod-like among others. Although other shaped aggregates may be used, in one embodiment of the disclosure, it is generally preferable that the cell aggregates be spherical or cylindrical. If the aggregates are comprised of only one cell type, they are referred to as "spheroids; if they are a mixture of multiple cell types (e.g. epithelia and mesenchymal cells), they are referred to as "organoids." In addition, the term "spheroid" indicates a floating aggregate of cells all being the same cell type (e.g. an aggregate from a cell line); an "organoid" is a floating aggregate of cells comprised of multiple cell types, an epithelial cell and its mesenchymal partner cells, typically an endothelial cell and a stromal cell. The cells can be stem/progenitors of these categories of cells or can be mature cells.

As used herein, the term "cell" refers to a eukaryotic cell. In some embodiments, this cell is of animal origin and can be a stem cell or a somatic cell. The term "population of cells" refers to a group of one or more cells of the same or different cell type with the same or different origin. In some embodiments, this population of cells may be derived from a cell line; in some embodiments, this population of cells may be derived from a sample of organ or tissue.

The term "biliary tree stem cells" refers to stem cells found throughout the biliary tree with the ability to transition into committed hepatic and/or pancreatic progenitor cells. They are found in both the extramural glands—tethered to the surface of the bile ducts—and the intramural glands—within the bile duct walls. The generic biomarkers for the biliary tree stem cells (hBTSCs) include pluripotency genes (e.g. OCT4, SOX2, NANOG, SALL4, KLF4, KLF5); one or another of the isoforms (standard or variant) of CD44, the hyaluronan receptors; CXCR4; cytokeratins 8 and 18. There are 3 stages identified so far: stage 1 hBTSCs: expresses sodium iodide symporter, CXCR4 but not LGR5 or EpCAM; stage 2 hBTSCs express less of NIS but gain expression of LGR5 but not EpCAM; stage 3 hBTSCs (found in the gallbladder, in the large intrahepatic bile ducts and hepato-pancreatic common duct) expresses LGR5 and EpCAM and is a precursor to the hepatic stem cells (in the liver) and to the pancreatic stem cells (in the hepato-pancreatic common duct.

As used herein the term "cancer stem cells" refers to the cells found within solid tumors or hematological cancers that possess characteristics associated with normal stem cells, specifically the ability to self-replicate and to be multi potent, that is give rise to multiple cell types.

The term "hepatic stem cells" refers to stem cells found in the canals of Hering, intrahepatic bile ductules, connecting the ends of the biliary tree to the liver and retaining the ability to self-replicate and be multipotent. The biomarkers for these cells include epithelial cell adhesion molecule (EpCAM) found in the cytoplasm and at the plasma membrane, neural cell adhesion molecule (NCAM), very low levels (if any) of albumin, an absence of alpha-fetoprotein (AFP), an absence of P450 A7, an absence of secretin receptor (SR). Hepatic stem cells and hepatoblasts express cytokeratins 8 and 18 and 19.

The term "hepatoblasts" refers to bipotent hepatic cells that can give rise to hepatocytic and cholangiocytic lineages, that have an extraordinary ability to proliferate (that is expand) but with less ability to self-replicate than is observed in hepatic stem cells. These cells are characterized by a biomarker profile that overlaps with but is distinct from hepatic stem cells, expressing EpCAM primarily at the plasma membrane, intercellular adhesion molecule (ICAM-1) but not NCAM, P450A7, cytokeratin 7, secretin receptor, albumin, high levels of AFP, and minimal (if any) pluripotency genes.

As used herein the term "committed progenitor" refers to a unipotent progenitor cell that gives rise to a single cell type, e.g. a committed hepatocytic progenitor cell (usually recognized by expression of albumin, AFP, glycogen, ICAM-1, various enzymes involved with glycogen synthesis) gives rise to hepatocytes and a committed biliary (or cholangiocytic) progenitor (recognized by expression of EpCAM, cytokeratins 7 and 19, aquaporins, CFTR, and membrane pumps associated with management of bile) gives rise to cholangiocytes.

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

The term "culture" or "cell culture" means the maintenance of cells in an artificial, in vitro environment. A "cell culture system" is used herein to refer to culture conditions in which a population of cells may be grown as monolayers or in suspension (spheroids, organoids).

"Culture medium" is used herein to refer to a nutrient solution for the culturing, growth, or proliferation of cells. Culture medium may be characterized by functional properties such as, but not limited to, the ability to maintain cells in a particular state (e.g. a pluripotent state, a quiescent state, etc.), to mature cells—in some instances, specifically, to promote the differentiation of progenitor cells into cells of a particular lineage. Non-limiting examples of culture media are Kubota's medium, a medium designed for endodermal stem/progenitors, a hormonally defined medium (HDM) designed to drive the stem/progenitors either to hepatocytes (HDM-H), to cholangiocytes (HDM-C), or to pancreatic islets (HDM-P), which are further defined herein below. In some embodiments the medium may be a "seeding medium" used to present or introduce cells into a given environment. In other embodiments, the medium may be a "differentiation medium" used to facilitate the differentiation of cells. Such media are comprised of a "basal medium" or a mixture of nutrients, minerals, amino acids, sugars, lipids, and trace elements and supplemented either with serum (serum supplemented media or SSM) or with a defined mix of purified hormones, growth factors and nutrients (HDM) and used for maintenance of cells ex vivo. As used herein, "HDM-H" is an HDM used in combination with substrata of type IV collagen and laminin to drive the differentiation of endodermal stem/progenitors to mature hepatocytes. "HDM-C," as used herein, refers to an HDM used in combination with substrata of type I/III collagen and fibronectin and designed to drive the differentiation of endodermal stem/progenitors to mature cholangiocytes. "HDM-P" is an HDM used in combination with substrata of type IV collagen and laminin to drive the differentiation of endodermal stem/progenitors to a mature pancreatic islet fate. Basal media are buffers comprised of amino acids, sugars, lipids, vitamins, minerals, salts, and various nutrients in compositions that mimic the chemical constituents of interstitial fluid around cells. Basal media are the starting points for buffers used for cell cultures. In addition, cell culture media are usually comprised of basal media supplemented with a small percentage (typically 2-10%) serum to provide requisite signaling molecules (hormones, growth factors) needed to drive a biological process (e.g. proliferation, differentiation). Although the serum can be autologous to the cell types used in cultures, it is most commonly serum from animals routinely slaughtered for agricultural or food purposes such as serum from cows, sheep, goats, horses, etc. Serum is also used to inactivate enzymes that are part of tissue dissociation processes.

The terms "equivalent" or "biological equivalent" are used interchangeably when referring to a particular molecule, biological, or cellular material and intend those having minimal homology while still maintaining desired structure or functionality.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. Further, the expression level of multiple genes can be determined to establish an expression profile for a particular sample. As used herein, the term "lower level" in reference to expression level refers to an amount in a cancer cell that is less than the amount in a non-cancer control sample.

Exemplary growth factors include, but are not limited to, epidermal growth factors (EGFs), fibroblast growth factors (FGFs), hepatocyte growth factors (HGFs), insulin-like growth factors (IGFs), transforming growth factors (TGFs), nerve growth factors (NGFs), neurotrophic factors, interleukins, leukemia inhibitory factors (LIFs), vascular endothelial cell growth factors (VEGFs), platelet-derived growth factors (PDGFs), stem cell factor (SCFs), colony stimulating factors (CSFs), GM-CSFs, erythropoietin, thrombopoietin, heparin binding growth factors, IGF binding proteins, placental growth factors, Wnt signals.

As used herein, the term "functional" may be used to modify any molecule, biological, or cellular material to intend that it accomplishes a particular, specified effect.

The term "gene" as used herein is meant to broadly include any nucleic acid sequence transcribed into an RNA molecule, whether the RNA is coding (e.g., mRNA) or non-coding (e.g., ncRNA).

As used herein, the term "hyaluronan," or "hyaluronic acid," refers to a polymer of a uronic acid and an aminosugar [1-3] composed of a disaccharide unit of glucosamine and gluronic acid linked by β1-4, β1-3 bonds and salts thereof. Thus, the term hyaluronan refers to both natural and synthetic hyaluronan.

As used herein, the term "immunocompromised" in reference to an animal is one with an impaired immune system such that it is incapable of fully reacting immunologically to pathogens. Those skilled in the art will recognize that this may be due to a genetic disorder, disease process, irradiation or drugs, such as corticosteroids or immunosuppressive agents, given to treat a disorder that inhibits immune function. Examples of drugs that suppress the immune system are methotrexate, cyclophosphamide, 6-mercaptopurine, vincristine, and the like. Suitable immunocompromised animals for use in the practice of the present disclosure are the athymic nude mouse, SCID mouse, SCID/NOD, NOD scid gamma (NSG), BNX immunodeficient mouse, and the like.

In one preferred embodiment, the host will be immunocompromised if the transplant of hFL-HCC cells is allogeneic or xenogeneic The term "isolated" as used herein refers to molecules or biologicals or cellular materials being substantially free from other materials.

"Kubota's medium" as used herein refers to any basal medium containing no copper, low calcium (<0.5 mM), insulin, transferrin/Fe, free fatty acids bound to purified albumin and, optionally, also high density lipoprotein. Kubota's Medium or its equivalent is serum-free and contains only purified and defined mix of hormones, growth factors, and nutrients. In certain embodiments, the medium is comprised of a serum-free basal medium (e.g., RPMI 1640 or DME/F12) containing no copper, low calcium (<0.5 mM) and supplemented with insulin (5 μg/mL), transferrin/Fe (5 μg/mL), high density lipoprotein (10 μg/mL), selenium (10-10 M), zinc (10 12 M), nicotinamide (5 μg/mL), and a mixture of purified free fatty acids bound to a form of purified albumin. Non-limiting, exemplary methods for the preparation of this media have been published elsewhere, e.g., Kubota H, Reid L M, Proceedings of the National Academy of Sciences (USA) 2000; 97:12132-12137, the disclosure of which is incorporated herein in its entirety by reference.

The term "mesenchymal cell" refer to cells of the mesenchyme. These are loose cells embedded in a mesh of proteins and fluid (i.e. extracellular matrix). Mesenchyme gives rise to most of the body's connective tissues.

The terms "nucleic acid," "polynucleotide," and "oligonucleotide" are used interchangeably and refer to a polymeric form of nucleotides of any length, either deoxyribonucleotides or ribonucleotides or analogs thereof. Polynucleotides can have any three dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double and single stranded molecules. Unless otherwise specified or required, any aspect of this technology that is a polynucleotide encompasses both the double stranded form and each of two complementary single stranded forms known or predicted to make up the double stranded form.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the term "subject" and "patient" are used interchangeably and are intended to mean any animal. In some embodiments, the subject may be a mammal. In further embodiments, the subject may be a human or non-human animal (e.g. a mouse or rat).

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. In addition, when a cancer cell is said to "substantially not express" a particular gene, this refers to less than or equal to ±10% (or more preferably less than or equal to ±5%) as compared to a non-cancer cell.

The term "transplantable" in reference to a tumor line refers to a tumor grown in a laboratory animal. The term "xenotransplantable" is one that has or will be transplanted between members of different species, for example, a human tumor that is transplantable into a mouse. A tumor from a donor animal (e.g. a human) is removed and often prepared into a single-cell suspension and administered to the host/recipient animal (e.g. a mouse). Some tumors must be propagated by transplanting small pieces of tumor or minced tumor material.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

Many embodiments described herein relate to a non-human animal that is immunocompromised and able to be transplanted with human tumor cells without immunologically rejecting the human cells. Such a host is used for establishment of a transplantable human fibrolamellar hepatocellular carcinoma (hFL-HCC) tumor line such as TU-2010, a non-human, immunocompromised animal carrying a transplantable human tumor of fibrolamellar hepatocellular carcinoma cells; the tumor line is called TU-2010.

The immunocompromised animal can be, for example, devoid of T cells, devoid of B cells, lacking functional NK cells, and/or deficient in cytokine signaling. In some embodiments, the non-human animal is an immunocompromised mouse. The immunocompromised mouse can be, for example, a NOD scid gamma mouse (or NOD.Cg-Prkdc$^{scid}$ Il2rg$^{tm1 Wjl}$/SzJ).

In some embodiments, the xenotransplanted tumor in the non-human animal is a subcutaneous tumor. In some embodiments, the xenotransplanted tumor in the non-human animal is an intraperitoneal tumor, an ascites. The xenotransplanted tumor, once depleted of the host cells, can comprise, for example, approximately $10^6$ to $10^7$ hFL-HCC cells/gram The hFL-HCC tumor line, TU-2010, is unusually rich in cancer stem cells. Whereas hepatocellular carcinomas (HCCs) are comprised typically of ~0.5-3% cancer stem cells, and cholangiocarcinomas (CCAs) are comprised typically of ~10% cancer stem cells, the transplantable tumor line, TU-2010, is comprised of more than 60% cancer stem cells, a finding indicating the uniqueness of the TU-2010 tumor line.

The transplantable tumor line, TU-2010, is further comprised of a large percentage of mesenchymal cells derived from the host, the immunocompromised, non-human animal. The mesenchymal cells can comprise, for example, precursors to stellate cells, endothelial cells, stromal cells or pericytes. The non-human mesenchymal cells can account for 50% or more of the tumors transplanted subcutaneously and over 90% of those transplanted intraperitoneally.

The hFL-HCC cells of the TU-2010 transplantable tumor line express a fusion transcript DNAJB1-PRKACA that has been found in the majority (~70%) of human FL-HCC tumors.

The hFL-HCC cells of the TU-2010 transplantable tumor line do not express HDAC9.

The hFL-HCC cells of the TU-2010 transplantable tumor line express LGR5 but substantially do not express or express negligible level of epithelial cell adhesion molecule (EpCAM)

Human fibrolamellar hepatocellular carcinomas, including the cells in TU-2010, have phenotypic traits indicative of an origin from one or another of the biliary tree stem cell (hBTSC) populations. These include expression of one or more of the following markers:

endodermal stem/progenitor transcription factors (SOX9, SOX17, PDX1, FOXA1)

one or more stem cell genes such as the hyaluronan receptors (CD44), SALL4, LGR5, TROP-2, prominin (CD133), and Sonic Hedgehog (SHH)

one or more pluripotency genes and genes indicative of self-replication selected from NANOG, OCT4, KLF4, KLF5, SOX2, BMI1, AGR2 and SALL4.

one or more hepatic markers selected from CK7, CK18, CK19, CD68, DCLK1, HepPar-1, and KRT20 (KRT20 is found also in the epithelial cells of the intestine)

one or more pancreatic/endocrine markers such as PDX1, NGN3, PCSK1.

Fibrolamellar hepatocellular carcinomas, including the FL-HCCs in TU-2010, express various markers indicative of malignancy. The TU-2010 line expresses high levels of anterior gradient protein 2 homolog (AGR-2), associated with the down regulation of the phosphoprotein, P53, a tumor suppressor, and it secretes large amounts of enzymes that degrade extracellular matrix components. These findings are relevant to regulation of p53.

The hFL-HCC tumors, including the cells of the TU-2010 tumor line, express high levels of the aryl hydrocarbon receptor (AHR) implicating a possible pathogenic and oncogenic process involving dioxins or dioxin-like molecules.

The hFL-HCC tumors have aberrations or loss of expression of one (or more) histone deacetylases. For example the TU-2010 tumor line's cells have a lack of expression of HDAC 9, a member of a family of histone deacetylases involved in epigenetic repression and involved in regulation of transcription, development and cell cycle. HDAC 9 serves deacetylation of lysine residues on the N-terminal part of certain core histones (H2A, H2B, H3 and H4).

The non-human host used for transplantable human tumors, such as the transplantable human tumor line, TU-2010, is, of necessity, an immunocompromised host since the transplants are xenogeneic. The immunocompromised host can be, for example, devoid of T cells, devoid of B cells, lacking functional NK cells, and/or deficient in cytokine signaling. In some embodiments, the non-human host is an immunocompromised mouse. The immunocompromised mouse can be, for example, a NOD scid gamma (NSG) mouse.

The tumor cells of the transplantable tumor line can be transplanted subcutaneously or intraperitoneally in the non-human host.

The hFL-HCC tumors are rich in cancer stem cells. TU-2010 transplantable tumor line is particularly rich in human cancer stem cells. Whereas hepatocellular carcinomas (HCCs) are comprised typically of ~0.5-3% cancer stem cells, and cholangiocarcinomas (CCAs) are typically ~10% cancer stem cells, the TU-2010 transplantable tumor line is more than 60% cancer stem cells.

The hFL-HCCs can be highly desmoplastic, meaning that the tumor cells elicit a strong reaction from mesenchymal cells located near to the tumor cells. The TU-2010 tumor line is representative of this ability of hFL-HCCs to elicit desmoplastic responses; it comprises a mixture of hFL-HCC cells and a large percentage of host (i.e. murine) mesenchymal cells that can comprise, for example, precursors to stellate cells and endothelial cells. The host mesenchymal cells can account for over half of the cells of the tumor in subcutaneous tumors and over 90% of them in intraperitoneal tumors The human FL-HCC cells of the tumor line, TU-2010, express the fusion transcript DNAJB1-PRKACA, found in ~80% of FL-HCC tumors.

The cells of the human transplantable tumor line, TU-2010, express LGR5 but substantially do not express or express negligible levels of EpCAM.

In some embodiments, the human FL-HCC cells of the tumor line, TU-2010, express one or more markers indicative of an origin in one or another of the biliary tree stem cell subpopulations. These include one or more of the following biomarkers:
  endodermal stem/progenitor transcription factors (SOX9, SOX17, PDX1, FOXA1),
  stem cell genes such as the hyaluronan receptors (CD44), LGR5, TROP-2, prominin (CD133), and Sonic Hedgehog (SHH)
  one or more pluripotency genes and genes indicative of self-replication selected from NANOG, OCT4, KLF4, KLF5, SOX2, BMI1, and SALL4
  one or more hepatic markers selected from CK7, CK18, CK19, CD68, DCLK1, and HepPar-1, and KRT20 (also found in the epithelial cells of the intestine)
  one or more pancreatic/endocrine markers such as PDX1, NGN3, PCSK1.

The human FL-HCC cells, such as occurs in the TU-2010 tumor line, express biomarkers of malignancy. These include high levels of the anterior gradient protein 2 homolog (AGR-2), associated with the down regulation of the phosphoprotein, p53, a tumor suppressor and/or secrete high levels of enzymes that degrade extracellular matrix components.

The human FL-HCC cells, such as those of the TU-2010 tumor line and in primary FL-HCCs, express high levels of the aryl hydrocarbon receptor (AHR) implicating a possible pathogenic/oncogenic process involving dioxins or dioxin-like molecules as contributing to the development of the TU-2010 tumor cells and other FL-HCCs.

Human FL-HCCs have aberrations in or loss of expression of one or another of the histone deacetylase genes, a family of genes involved in regulation of transcription, development and the cell cycle through enzymatic removal of acetyl groups from histones. For example, the TU-2010 tumor line's cells have a lack of expression of HDAC9, HDAC 9 is involved in deacetylation of lysine residues on the N-terminal part of certain core histones H2A, H2B, H3 and H4). HDAC9 is low in primary FL-HCC tumors and also in HCCs as well.

Further embodiments relate to a tissue sample obtained from the tumor line.

hFL-HCC Cell Cultures.

Many embodiments described herein also relate to a cell culture comprising human FL-HCC cells. Ideally the hFL-HCCs are maintained in culture in a serum-free medium. In some embodiments, the serum-free medium is Kubota's Medium, one that culture selects for endodermal stem/progenitors and is non-permissive for cells at later maturational lineage stages.

Kubota's Medium is a wholly defined medium originally designed for rodent hepatoblasts and later found effective also human hepatoblasts (hHBs), human hepatic stem cells (hHpSCs), human biliary tree stem cells (hBTSCs), human pancreatic stem cells and for human hepatic and pancreatic progenitors. In some embodiments, Kubota's Medium comprises any basal medium (e.g., RPMI 1640 or DMEM-F12) with no copper, low calcium (e.g., 0.3 mM), ~$10^{-9}$ M selenium, ~0.1% bovine serum albumin or human serum albumin (highly purified and fatty acid free), ~4.5 mM nicotinamide, ~0.1 nM zinc sulfate heptahydrate, ~$10^{-8}$ M hydrocortisone, ~5 µg/ml transferrin/Fe, ~5 µg/ml insulin, ~10 µg/ml high density lipoprotein, and a mixture of purified free fatty acids that are added after binding them to purified serum albumin. The free fatty acid mixture consists of ~100 mM each of palmitic acid, palmitoleic acid, oleic acid, linoleic acid, linolenic acid, and stearic acid In some embodiments used for maintaining the cells as stem cells, the serum-free medium is further supplemented with hyaluronans or substrata of hyaluronans are used.

In some embodiments when the cells are being differentiated towards an adult fate, the serum-free hormonally defined medium is comprised of Kubota's Medium is further supplemented with at least one growth factor or cytokine. The growth factor can be, for example, epidermal growth factor (EGF), hepatocyte growth factor (HGF) fibroblast growth factor (FGF) and/or vascular endothelial cell growth factor (VEGF).

In some embodiments as when the cells are being differentiated towards a hepatocyte fate, the serum-free hormonally defined medium is comprised of Kubota's Medium is further supplemented with: calcium to a level of 0.6 mM; ~$10^{-12}$ M copper; EGF (~10 ng/ml); bFGF (~20 ng/ml); tri-iodothyronine or T3 (~$10^{-9}$ M); glucagon (7 µg/L), galactose (2 g/L), oncostatin M (~10 ng/ml); and HGF (~20 ng/ml). For more optimal differentiation to an hepatocyte fate, this HDM is used in combination with embedding the cells into a mixture of type IV collagen, laminin, and hyaluronans.

In some embodiments as when the cells are being differentiated towards a cholangiocyte fate, the serum-free hormonally defined medium is comprised of Kubota's Medium that is further supplemented with: calcium to a level of ~0.6 mM; ~$10^{-12}$ M copper; bFGF (~20 ng/ml); T3 (~$10^{-9}$M); VEGF (20 ng/ml) and HGF (10 ng/ml). For more optimal differentiation to a cholangiocyte fate, this HDM-C is used in combination with embedding the cells into a mix of type I collagen and hyaluronans In some embodiments as when the cells are being differentiated towards a pancreatic islet fate, the serum-free hormonally defined medium is comprised of Kubota's Medium is prepared without hydrocortisone and then further supplemented with: calcium to a level of ~0.6 mM; ~$10^{-12}$ M copper; bFGF (~20 ng/ml); B27 (~2%), ascorbic acid (~0.1 mM), cyclopamine (~0.25 µM), retinoic acid (~1 µM); furthermore, the bFGF is used for the first 4 days and then is replaced with exendin-4 (50 ng/ml) and HGF (20 ng/ml) for the remainder of the time. For more optimal differentiation to a pancreatic islet fate, this HDM-P is used in combination with embedding cells into a mix of type IV collagen, laminin, and hyaluronans In some embodiments, the cultures are primary cultures of the dispersed tumor and so are a mix of the hFL-HCCs and the host (e.g. murine) mesenchymal cells.

In some embodiments, the human cells can be purified by immune-selection from the tumor cell suspensions such that the cultures are predominantly (>90%) the human FL-HCC cells.

In some embodiments, the human FL-HCC cells of the cell cultures are rich in cancer stem cells. If the host (e.g. murine) mesenchymal cells have been depleted by immune-selection technologies, the hFL-HCCs are dominant (>90% of the cells in culture) and comprised of cancer stem cells that are over 50% and up to 70% of the human cells in the cultures.

In some embodiments, the human FL-HCC cells are plated onto a culture substratum such as plastic; in some, the substratum can be a purified form of a matrix component (e.g. hyaluronan, a collagen, an adhesion molecule such as laminin); in some, the substratum can be a complex extracellular matrix extract such as a biomatrix scaffold or Matrigel.

In some embodiments, the human FL-HCC cells of the cell culture can be established as spheroids or organoids, floating aggregates of cells. In other embodiments, the hFL-HCC cells of the cell culture are in the form of monolayers.

Methods for Establishing and Maintaining hFL-HCC Tumor Lines

In some embodiments, the hFL-HCC cells are obtained from an ascites fluid; in some embodiments, the hFL-HCC cells are obtained from a solid tumor from a patient suffering from the disease. To establish a tumor line, the tumor cells must first be culture selected for the cancer stem/progenitors present in the tumor. The culture selection makes use of restrictive conditions that are not permissive for other lineage stages of cells other than the ones desired. The method comprises culturing cells obtained from the ascites fluid or from the solid tumor with a wholly defined, serum-free media (e.g., Kubota's Medium), designed to culture select endodermal stem/progenitor cells (such as the cancer stem cells in the human FL-HCC tumors).

Many embodiments described herein also relate to a method for obtaining a human FL-HCC tumor line, comprising isolating human FL-HCC cells from a human subject suffering from FL-HCC; culture selecting the cancer stem/progenitor cell population(s) under conditions permissive for the cancer stem cells but not for the later maturational lineage stages of cells; and then transplanting them into an immunocompromised, non-human animal. The immunocompromised non-human animal can be, for example, an immunocompromised mouse such as NOD scid gamma (NSG) mouse.

In some embodiments, the hFL-HCC cells isolated from the human subject are transplanted subcutaneously into the immunocompromised non-human animal. In some embodiments, the hFL-HCC cells isolated from the human subject are transplanted intraperitoneally into the immunocompromised non-human animal.

In some embodiments, the method comprises transplanting from 10 to $10^8$ hFL-HCC cells, or about $10^2$ to $10^7$ hFL-HCC cells, or about $10^2$ to $10^3$ hFL-HCC cells, or about $10^3$ to $10^4$ hFL-HCC cells, or about $10^4$ to $10^5$ hFL-HCC cells, or about $10^5$ to $10^6$ hFL-HCC cells, or about $10^6$ to $10^7$ hFL-HCC cells, into the immunocompromised non-human animal. In some embodiments, the method comprises monitoring the immunocompromised non-human animal for tumor formation for 2 to 9 months. Depending on the number of cells transplanted (with more transplanted cells correlating with more rapid tumor formation), for example, formation of a xenografted human tumor can occur in about 2-3 months (with transplantation of over $10^6$ cells), and ranging to 7-9 months (with transplantation of 10-100 cells).

Many embodiments described herein also relate to a method for maintaining a human FL-HCC tumor line, comprising obtaining human FL-HCC cells from a first passaged xenografted tumor, dispersing the cells by enzymatic or mechanical methods into a cell suspension, and transplanting the human FL-HCC cells into a second immunocompromised non-human animal. The first and second immunocompromised non-human animals can be, for example, immunocompromised mice such as NOD scid gamma mice.

In some embodiments, the method comprises culturing cells obtained from the xenografted tumor with a serum-free medium (e.g., Kubota's Medium) to culture select human FL-HCC cells. In some embodiments, the serum-free medium is supplemented with hyaluronans. In some embodiments, the serum-free medium is supplemented with one or more growth factors. The growth factors can be, for example, HGF, FGF, EGF, and/or VEGF.

In some embodiments, the human FL-HCC cells obtained from the first immunocompromised non-human animal are transplanted subcutaneously into the second immunocompromised non-human animal. In some embodiments, the human FL-HCC cells obtained from the first immunocompromised non-human animal are transplanted intraperitoneally into the second immunocompromised non-human animal.

Method for Culturing hFL-HCC Cells

Many embodiments described herein also relate to a method for culturing human FL-HCC cells, comprising separating human FL-HCC cells of a xenografted tumor from non-human cells, suspending the separated human FL-HCC cells in a serum-free medium (e.g., Kubota's Medium), and plating the hFL-HCC cells onto culture plastic, or onto a purified matrix component (e.g. hyaluronan, a collagen, an adhesion molecule such as laminin) or into/onto a complex extracellular matrix extract (e.g. biomatrix scaffolds, Matrigel).

In some embodiments, the human FL-HCC cells of the xenografted tumor are separated from non-human cells (e.g.

murine mesenchymal cells) by magnetic immuno-selection or by an equivalent immune-selection technology (e.g. flow cytometry) or any technology that distinguishes human from non-human cells.

In some embodiments, the culture substratum comprises a culture plastic. In some embodiments, the culture substratum comprises a monolayer coating or a 3-dimensional form (e.g. hydrogel) of a purified extracellular matrix component (e.g. hyaluronan, a collagen, an adhesion molecule such as laminin), a mix of one or more of the matrix component, or an extract enriched in extracellular matrix (e.g. biomatrix scaffolds, Matrigel).

In some embodiments, the human FL-HCC cells are suspended in the medium and aggregation of the cells occurs to form spheroids if only the hFL-HCC are part of the aggregates or organoids if the aggregates contain hFL-HCC and other cell types (e.g. vascular or mesenchymal cells). In some embodiments, the plated hFL-HCC cells form monolayers.

Method for Drug Screening and Testing

Many embodiments described herein also relate to a method for drug screening, comprising contacting a candidate drug with cultured hFL-HCC cells, and monitoring the effect(s) of the candidate drug on the cultured hFL-HCC cells.

In some embodiments, the cultured hFL-HCC cells are in the form of floating aggregates of cells, spheroids or organoids.

Many embodiments described herein also relate to a method for drug testing, comprising administering a candidate drug to a non-human animal that has been transplanted with a tumor containing human FL-HCC cells, and monitoring the effect of the candidate drug on the xenotransplanted tumor.

Many embodiments described herein also relate to a method for suppressing the growth of human FL-HCC cells, comprising treating the hFL-HCC cells with a hedgehog signaling pathway inhibitor and/or a histone deacetylase inhibitor and/or some other candidate drug.

In some embodiments, the method comprises treating the human FL-HCC cells with a hedgehog signaling pathway inhibitor (e.g., GDC-0449). In some embodiments, the method comprises treating the human FL-HCC cells with a histone deacetylase inhibitor (e.g., SAHA or SBHA).

Many embodiments described herein also relate to a method for treating FL-HCC in a human patient, comprising administering to the patient an effective amount of a hedgehog signaling pathway inhibitor and/or a histone deacetylase inhibitor.

In some embodiments, the method comprises administering to the patient an effective amount of a hedgehog signaling pathway inhibitor (e.g., GDC-0449). In some embodiments, the method comprises administering to the patient an effective amount of a histone deacetylase inhibitor (e.g., SAHA or SBHA).

Method for Diagnosis of hFL-HCCs

At present, the only biomarker identified for ~80% of human FL-HCCs is the fusion gene, DNAJB1-PRKACA. Histologically, the tumor is recognizable as aggregates of large polygonal cells with abundant eosinophilic cytoplasm, large, vesiculated nuclei and large nucleoli; the tumor cells are nestled within bands of stroma. In addition to the fusion gene and the distinctive histological traits, one can identify hFL-HCCs by phenotypic traits typical of biliary tree stem cells. These hFL-HCC tumors are hypothesized to derive from one or another of the biliary tree stem cell subpopulations that constitute the native stem cells and progenitors for both liver and pancreas.

Recognition of the Origins of hFL-HCCs from hBTSC Subpopulations is Indicated by the Expression of:
  one or more endodermal transcription factors (e.g. SOX9, SOX17, PDX1, FOXA1)
  one or more pluripotency genes and genes indicative of self-replication (e.g. NANOG, OCT4, KLF4, KLF5, SOX2, BMI1, TROP-2, and SALL4) and evidence for multipotency
  one or more hepatic markers (e.g. alpha-fetoprotein, albumin, CK7, CK18, CK19, CD68, DCLK1, and HepPar-1), and KRT20 (also found in the epithelial cells of the intestine)
  one or more pancreatic/endocrine markers (e.g. PDX1, NGN3, PCSK1, insulin, glucagon, amylase, MUC or mucin).

Recognition of Malignancy in hFL-HCCs is Indicated by:
  Expression of high levels of anterior gradient protein 2 homolog (AGR-2), associated with the down regulation of the phosphoprotein, p53, a tumor suppressor.
  Release of high levels of enzymes that degrade and dissolve extracellular matrix (e.g. heparanase, matrix metalloproteinases—MMPs)
  Aberrant regulation of 03, a tumor suppressor Recognition of factors contributing to the pathogenic/oncogenic process in hFL-HCCs is indicated by: high levels of the aryl hydrocarbon receptor (AHR) implicating a possible contribution of dioxins or dioxin-like molecules in the aetiology of hFL-HCCs Recognition of key genes that are affected in hFL-HCCs is indicated by: aberrations in or absence of one or more histone deacetylases (HDAC), enzymes critically associated with regulation of transcription, development, cell proliferation, and the cell cycle.

In addition, the human FL-HCC tumors will have biomarkers of malignancy. Some of the biomarkers indicative of malignancy include high levels of expression of AGR2, over-production of matrix-degrading enzymes (e.g. heparanase, matrix metalloproteinases or MMPs), very high levels of AHR and aberrant levels of one or another HDAC gene and/or aberrations in the regulation of p53, a tumor suppressor.

In some embodiment, the method further comprises culturing cells obtained from an ascites fluid or solid tumor derived from a human subject and subjecting it to culture conditions that are wholly serum-free and in a medium (e.g., Kubota's Medium), designed for culture selection of endodermal cancer stem/progenitors and then detecting the formation of spheroids or organoids.

Methods for Determining Whether a Patient has FL-HCC and Treating a Patient Diagnosed with FL-HCC In one aspect is provided a method of determining whether a patient has fibrolamellar hepatocellular carcinoma (FL-HCC), comprising: (a) measuring gene expression levels of at least one of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, and TNRC6C; and (b) comparing the gene expression level to one or more control samples.

In some embodiments, overexpression of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163 or TNRC6C relative to the control sample is associated with presence of FL-HCC. On the other hand, a lack of increased expression of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163 or TNRC6C relative to the control sample indicates that the patient is not likely to have FL-HCC.

In other embodiments, overexpression of PCSK1, CA12, NOVA1, SLC16A14, TNRC6C, TMEM163, and RPS6KA2 relative to the control sample is associated with presence of FL-HCC. On the other hand, a lack of increased expression of PCSK1, CA12, NOVA1, SLC16A14, TNRC6C, TMEM163, and RPS6KA2 relative to the control sample indicates that the patient is not likely to have FL-HCC.

In yet other embodiments, overexpression of C10orf128, OAT, PAK3, PCSK1, PHACTR2, SLC16A14, TMEM163, and TNRC6C relative to the control sample is associated with presence of FL-HCC. On the other hand, a lack of increased expression of PCSK1, CA12, NOVA1, SLC16A14, TNRC6C, TMEM163, and RPS6KA2 relative to the control sample indicates that the patient is not likely to have FL-HCC.

In some embodiments, the control sample is selected from the group consisting of hepatocellular carcinomas (HCCs), cholangiocarcinomas (CCAs), normal liver cells, and normal cholangiocytes.

As used herein, the term "overexpression" refers to the level of mRNA and/or protein of a specific, for example, C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163 or TNRC6C, expressed in a suspected tumor cell of a sample collected from a patient being elevated in comparison to the level as measured in a control sample. The mRNA and/or protein expression level may be determined by a number of techniques known in the art including, but not limited to, quantitative RT-PCR, western blotting, immunohistochemistry, and suitable derivatives of the above.

In some embodiments, the gene expression of PCSK1 and at least one additional gene selected from the group consisting of C10orf128, CA12, CREB3L1, GALNTL6, IRF4, ITPRIP, KCNE4, NOVA1, OAT, PAK3, PHACTR2, RPS6KA2, SLC16A14, TMEM163, and TNRC6C is measured. In another embodiment, the gene expression of PCSK1 and at least one additional gene selected from the group consisting of C10orf128, CA12, CREB3L1, GALNTL6, IRF4, ITPRIP, KCNE4, NOVA1, OAT, PAK3, PHACTR2, RPS6KA2, SLC16A14, TMEM163, and TNRC6C is overexpressed.

In some embodiments, at least two, at least three, at least four, at least five, at least six, at least seven or all eight of genes C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163 and TNRC6C are measured. In some embodiments, at least two, at least three, at least four, at least five, at least six, at least seven or all eight of genes C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163 and TNRC6C are overexpressed. In some embodiments, any one of the listed genes is expressly excluded from the genetic signature of hFL-HCC.

In one aspect is provided a method of treating a patient determined to have FL-HCC by administering to the patient an effective amount of at least one therapeutic that decreases expression of at least one of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, or TNRC6C.

In some embodiments, the at least one therapeutic is selected from the group consisting of a small molecule, RNA interference, and a locked nucleic acid (LNA). In other embodiments, the at least one therapeutic is an immunotherapy.

In one aspect is provided a method of treating a patient determined to have hFL-HCC by administering to the patient an effective amount of at least one therapeutic that regulates PRKACA or SRC network hubs.

In another aspect is provided method of treating a patient determined to have hFL-HCC by administering to the patient an effective amount of at least one therapeutic that regulates substrate targets of the kinase PRKACA (Protein kinase A catalytic subunit alpha) or carbonic anhydrases.

Working Examples

Human fibrolamellar hepatocellular carcinomas (hFL-HCCs) are rare liver cancers occurring in young people, have an unknown aetiology, and are currently treatable only by surgery. Immunohistochemistry (IHC) of 9 hFL-HCCs and tissue microarrays of 18 FL-HCCs indicated robust expression of endodermal stem/progenitor markers (SOX9, PDX1, SOX17, sonic hedgehog—SHH, SALL4, OCT4). A first-ever, transplantable hFL-HCC tumor line, TU-2010, established in immunocompromised mice, proved rich in cancer stem cells, indicated functionally by spheroid/organoid formation, limiting dilution tumorigenicity, and culture; by flow cytometric and IHC evidence of pluripotency (e.g. KLF4, OCT4, NANOG) and endodermal stem/progenitor markers (e.g., LGR5, SOX9, PDX1, CD44, SHH); and effects of differentiation media on these traits. Transcriptomic analyses revealed a global expression profile for human FL-HCCs indicating their derivation from biliary tree stem cells, stem cell precursors to liver and pancreas. A recurrent fusion gene unique to hFL-HCCs, DNAJB1-PRKACA, was confirmed. In vitro studies and phenotypic traits suggest hedgehog proteins and histone deacetylases to be therapeutic targets. Oikawa et al. (2015) Nature Communications 6:8070, incorporated by reference in its entirety.

Materials and Methods 1.1. Paraffin Sections of Normal Livers Versus hFL-HCCs.

Sections (5 μm) prepared from the original paraffin blocks of 9 hFL-HCC tumors and ones from Tissue MicroArrays (TMAs) of 19 normal adult livers and 18 hFL-HCC patients were obtained from Memorial Sloan Kettering Cancer Center (MSKCC, New York City, NY) and used for IHC assays. They were obtained with approval of the IRB at MSKCC. Handling of all the samples fully met compliance and privacy requirements as per HIPAA laws.

1.2. Original Fibrolamellar Hepatocellular Carcinoma (hFL-HCC) Used to Establish the Tumor Line, TU-2010.

A male patient, age 25, presented in August 2008 to Greenwich Hospital (Yale/New Haven Hospital, Greenwich, CT) with acute swelling of his right lower leg. During the initial evaluations, he was found to have an extensive venous thrombus extending from his right ankle into his inferior vena cava. A CT of his chest/abdomen/pelvis revealed multiple small pulmonary emboli and a large mass in his left liver with evidence of metastatic disease in the perihepatic lymph nodes, omentum and peritoneum. He had a venous filter inserted above the thrombus, was started on anticoagulation and transferred to MSKCC for further studies and therapy. The patient underwent a liver biopsy resulting in a pathologic diagnosis of hepatocellular carcinoma (HCC) and subsequently had an extensive debulking procedure which included a left hepatic lobectomy and debulking of peritoneal and omental nodules. Macroscopically, the peritoneal and omentum nodules proved to be tumors and histologically revealed tumor tissue consistent with a diagnosis of hFL-HCC. Surgical pathology revealed tumor cells positive for HepPar1 and cytokeratin 7 (CK7). Analyses of EMA (epithelial membrane antigen) and AFP (α-fetoprotein) were not conclusive and neither were tissues stained for reticulin, iron, or PAS-3.

A summary of the characterization of the original tumor by the pathologists at Memorial Sloan Kettering Cancer Center (MSKCC) is given in Table 1. A later round of biopsies resulted in similar pathology reports. These included cytology on pleural fluid found replete with tumor cells, which also had a pathology consistent with a diagnosis of FL-HCC.

TABLE 1

Summary of findings on the original hFL-HCC tumor used to establish the TU-2010 transplantable tumor line.
(patient data from Memorial Sloan Kettering Cancer Center-MSKCC)**

| BIOMARKERS | ASSAYS | Staining Intensity (% cells Staining) or Gene Expression Change | Comments |
| --- | --- | --- | --- |
| Ribonucleotide reductase subunit M1 (RRM1) | IHC | 2+ (80%) | Certain drugs, such as gemcitabine, are of little benefit due to high expression of RRM1 |
| Breast Cancer Resistant Protein (BCRP) | IHC | 2+ (75%) | Obviates usefulness of cisplatin and carboplatin |
| Secreted Protein Acidic and Rich in Cysteine (SPARC) | IHC | 2+ (35%) | Nab-paclitaxel |
| SPARC | Microarray | Increased (3.51) | Nab-paclitaxel |
| Multidrug Resistance associated Protein 1 (MRP1) | IHC | 2+ (30%) | Minimal effects expected with etoposide, vincristine |
| ABCC1 | Microarray | Increased (3.03) | Minimal benefit with Paclitaxel, Topotecan |
| Her2/Neu | IHC | 2+ (10%) and 1+ (30%) | FISH analyses were done, and 60 interphase nuclei were examined; the ratio of HER2/neu signals to chromosome 17 signals was 1.63 to 1 indicating no amplification of this gene |
| HIF1A | Microarray | Increased (10.66) | Agents associated with clinical benefits include sorafenib, sunitinib, bevacizumab |
| PDGFRB | Microarray | Increased (2.3) | Agents associated with clinical benefits include sorafenib, sunitinib, imatinib |
| TOP2B | Microarray | Increased (4.55) | Beneficial agents include doxorubicin, epirubicin, liposomal doxorubicin |
| ADA | Microarray | Increased (4.05) | Beneficial agents include pentostatin |
| Estrogen receptor, progesterone receptor, androgen receptor | | Negative | Classic hormone therapies are not logical for use with the tumor |

**Approval for the research studies on the tumor and on the patient was given by the IRB at MSKCC (New York City, NY), and compliance with HIPAA regulations was met.

The patient was subsequently treated with various oncoloytic agents including sorafenib, doxorubicin, gemcitabine, cisplatinum, 5-FU, bevacizumab, and thalidomide with limited or no response. In September of 2009 after showing progressive enlargement in the perihepatic and retroperitoneal nodes, recurrent disease in the liver, and increasing size of omental and peritoneal nodules, the patient returned to MSKCC to obtain further tissue for tumor sensitivity studies and debulking. Biopsies were taken, but his disease was too extensive for debulking. Paclitaxel and thalidomide were then started based on sensitivity studies but was poorly tolerated with continued disease progression, so treatment was stopped. After 4 months it was realized that he had widely disseminated disease especially in the ascites fluid. In early February 2010, a palliative paracentesis was done for massive ascites, and approximately 5 liters of fluid were removed and transferred to several researchers, including those in the UNC research lab, in hopes that studies on the tumor might identify alternate treatments. A week later the patient passed away peacefully.

1.3. Ascites Fluid.

Four liters of ascites fluid were received at UNC within 10 hours of removal from the patient. The cells were centrifuged and pooled, yielding about $2 \times 10^7$ cells, and plated on plastic or other substrata (laminin, hyaluronans, types I, III or IV collagens) in serum-free Kubota's Medium (KM) prepared in either RPMI 1640 or in DMEM-F12 and presented as two-dimensional (2D) monolayers or three-dimensional (3D) hydrogels. Serum-free Kubota's Medium (KM) has been found to select for endodermal stem cells and progenitors and is not permissive for survival of mature cells. Culture selection for tumor cells with stem cell properties was done in monolayer (2D) cultures and did best on plastic and in KM in DMEM-F12. Those in 3-D hydrogels behaved similarly in KM prepared in either DMEM-F12 or RPMI 1640, grew more slowly, and, in parallel, caused dissolution of hydrogels by hFL-HCC's considerable enzyme secretions that degrade extracellular matrix. This culture selection process proved successful for establishment of the transplantable tumor line as clarified in further details below.

1.4. Culture Conditions.

All media were sterile-filtered (0.22-µm filter) and kept in the dark at 4° C. before use. Hyaluronans were obtained from Glycosan Biosciences (Salt Lake City, Utah; now part of Biotime, Alameda, CA). Type III and IV collagens and laminin were obtained from Becton Dickinson (Research Triangle Park, NC).

1.5. Kubota's Medium.

(KM) is a serum-free medium designed originally for rodent hepatoblasts and then found effective also for human hepatoblasts, hepatic stem cells (hHpSCs), biliary tree stem cells (hBTSCs), and for pancreatic progenitors. It contains any basal medium (here being RPMI 1640) with no copper, low calcium (0.3 mM), $10^{-9}$ M selenium, 0.1% BSA, 4.5 mM nicotinamide, 0.1 nM zinc sulfate heptahydrate, $10^{-8}$ M hydrocortisone, 5 µg/ml transferrin/Fe, 5 µg/ml insulin, 10 µg/ml high density lipoprotein, and a mixture of purified free fatty acids that are added after binding to purified human serum albumin. Kubota's Medium is available commercially from PhoenixSongs Biologicals (Branford, CT).

1.6. Hormonally Defined Media (HDM).

Supplements can be added to KM to generate a serum-free, hormonally defined medium (HDM) that will facilitate differentiation of the normal hepatic or biliary tree stem cells to specific adult fates. These include supplementation with calcium to achieve at or above 0.6 mM concentration, 1 nM tri-iodothyronine (T3), $10^{-12}$ M copper, 10 nM of hydrocortisone and 20 ng/ml of basic fibroblast growth factor (bFGF). The medium conditions over and above these needed to selectively yield hepatocytes (HDM-H) versus cholangiocytes (HDM-C) versus pancreatic islets (HDM-P) are:

(1) HDM-H: supplementation further with 7 µg/L glucagon, 2 g/L galactose, 10 ng/ml epidermal growth factor (EGF) and 20 ng/ml hepatocyte growth factor (HGF).
(2) HDM-C: supplementation further with 20 ng/ml vascular endothelial cell growth factor (VEGF) 165 and 10 ng/ml HGF.
(3) HDM-P: prepared without glucocorticoids and further supplemented with 1% B27, 0.1 mM ascorbic acid, 0.25 µM cyclopamine, 1 µM retinoic acid, 20 ng/ml of FGF-7 for 4 days, then changed with one supplemented with 50 ng/ml exendin-4 and 20 ng/ml of HGF for 6 more days of induction.

1.7. Tissue Sourcing of Normal Tissue.

Adult, normal, human biliary tissues were dissected from intact livers and pancreases obtained but not used for transplantation into a patient. They were obtained through organ donation programs via United Network for Organ Sharing (UNOS). Those used for these studies were considered normal with no evidence of disease processes. Informed consent was obtained from next of kin for use of the tissues for research purposes, protocols received Institutional Review Board approval, and processing was compliant with Good Manufacturing Practice. The research protocol was reviewed and approved by the Institutional Review Board for Human Research Studies at the University of North Carolina at Chapel Hill, NC, USA.

1.8. Animals.

In preliminary studies, immunocompromised mice of several species (e.g. athymic nudes, SCID/NODs, NSGs) were obtained from suppliers or were obtained from breeding colonies on the UNC campus and used as hosts for the human FL-HCC cells. The findings were most successful with NOD.Cg-Prkdc$^{scid}$ Il2rg$^{tm1Wjl}$/SzJ. These are known commonly as NOD scid gamma or NSGs. These mice are devoid of T or B cells, lack functional NK cells and are deficient in cytokine signaling. The strain combines the features of the NOD/ShiLtJ (Stock Number 001976) background, the severe combined immune deficiency mutation (scid, which is caused by a spontaneous mutation in the Prkdc gene), and the IL2 receptor gamma chain deficiency. The animals were maintained in the quarters maintained by the Division of Laboratory Animals (DLAM). Procedures were performed according to protocols approved by the UNC School of Medicine at Chapel Hill IACUC. All species were inbred and housed in UNC's DLAM sterile facility in micro-isolated autoclaved cages with free access to autoclaved water and radiation sterilized food.

1.9. Transplantation of the Human FL-HCC Cells.

Efforts to establish a tumor line by transplanting the original ascites tumor cells immediately after removal from the patient were not successful. Rather, success was achieved with cells that survived and so were culture selected in serum-free Kubota's Medium (KM) and on culture plastic or on a substratum of hyaluronans. The culture-selected tumor cells were transplanted and yielded tumors after an initial passage of more than 6 months in the NSG mice. Thereafter, xenografted established tumors passaged by mincing tumor in KM supplemented with 1% hyaluronans (uncross-linked) and further supplemented with 50 ng/ml each of HGF and VEGF. The tumor mince (approximately 20 mgs) in the KM+1% hyaluronans+growth factors was injected subcutaneously into mice. The tumor mince form tumors in the absence of hyaluronans and growth factors but do so more slowly and will not yield tumors at all in some mice. Consistent, reproducible tumor formation occurred with the use of the supplements. If transplanted intraperitoneally, the tumor cells spread onto the serosal surfaces throughout the peritoneum and also onto the liver and pancreas.

Tissue processing of the human FL-HCC tumors to generate cell suspensions for ex vivo studies was conducted in RPMI 1640 supplemented with 0.1% bovine serum albumin, 1 nM selenium and antibiotics. Enzymatic processing buffer contained 600 U/ml type IV collagenase and 0.3 mg/ml deoxyribonuclease at 32° C. with frequent agitation for 15-20 min. Enriched suspensions were pressed through a 75 gauge mesh and spun at 1200 RPM for 5 min before re-suspension. Estimated cell viability by trypan blue exclusion was routinely higher than 95%.

1.10. Magnetic Immunoselection of Cells.

Human tumor cells were isolated from xenografted tumors. Negative sorting was done using EasySep magnetic bead immunoselection using the magnetic cups and beads (StemCell Technologies, Vancouver, Canada) and according to the manufacturer instructions. Briefly the dissociated cells were washed in phosphate-buffered saline (PBS) with 3% fetal bovine serum (FBS) (staining medium) were treated with FcR blocking antibody and incubated with a cocktail of biotin-conjugated anti-mouse antibody against lineage cells (Miltenyi Biotec Inc, Auburn, CA), and with biotin-conjugated anti-mouse-MHC class I (H-2K$^d$) (clone; SF1-1.1) and -CD31 (clone; MEC13.3) antibodies (BD Biosciences, San Jose, CA) at room temperature for 15 min.

Cells were incubated with biotin selection cocktail for 15 min, and then incubated with magnetic nanoparticles at room temperature for 10 min. The cups were magnetized, and cells or clumps of cells bound to the walls of the cup; those not bound (the human cells) were collected into a separate container. The cells bound to the cups were the mouse cells that were discarded. The human cells were suspended in KM and then plated.

The cells were plated onto culture plastic or on or in hyaluronan hydrogels (some of them supplemented with type III or IV collagen or laminin) and provided with serum-free KM. For the initial plating, the medium was supplemented with 2-5% FBS (HyClone, Waltham, MA). After a few hours, the medium was changed to the serum-free version, and this was used for all subsequent medium changes.

For the cultures of xenografted tumors, the human cells were sorted by immunoselection away from the murine (host) mesenchymal cells and then were plated in serum-free KM from the outset.

1.11. Immunocytochemistry and Immunohistochemistry.

For immunofluorescent staining, 5 μm frozen sections or cultured cells were fixed with 4% paraformaldehyde (PFA) for 20 min at room temperature, rinsed with PBS, blocked with 10% goat serum in PBS for 2 hours, and rinsed. Fixed cells were incubated with primary antibodies at 4° C. for 14 hours, washed, incubated for 1 hour with labeled isotype-specific secondary antibodies, washed, counterstained with 4',6-diamidino-2-phenylindole (DAPI) for visualization of cell nuclei and viewed using Leica DMIRB inverted microscope (Leica, Houston, TX) or a Zeiss ApoTome Axiovert 200M (Carl Zeiss Inc, Thornwood, NY).

For immunohistochemistry (IHC), the tissues were fixed in 4% PFA overnight and stored in 70% ethanol. They were embedded in paraffin and cut into 5-μm sections. After deparaffinization, antigen retrieval was performed with sodium citrate buffer (pH 6.0) or ethylenediaminetetraacetic acid (EDTA) buffer (pH 8.0) in a steamer for 20 min. Endogenous peroxidases were blocked by incubation for 15 min in 3% $H_2O_2$. After blocking, primary antibodies reacted against human but not mouse cells and were applied at 4° C. overnight. M.O.M immunodetection kit (Vector Laboratories, Burlingame, CA) was used for detecting primary mouse anti-human antibodies on mouse xenotransplant FL-HCC tumor to avoid the inability of the anti-mouse secondary antibody to endogenous mouse immunoglobulins in the tissue. Sections were incubated for 30 min at room temperature with ImmPRESS peroxidase-micropolymer staining kits and 3,3'-diaminobenzidine substrate (Vector Laboratories). Sections were lightly counterstained with hematoxylin. Antibodies used are listed in Table 2. Control images are given in FIG. 9.

TABLE 2

Antibodies for Immunohistochemistry

| Antibody | Species | Isotype | Manufacture | Reactivity | Retrieval |
|---|---|---|---|---|---|
| ABCG2 | Mouse | IgG2a | Millipore | H | CB |
| AFP | Mouse | IgG2a | SIGMA | H, D, P but, not M | CB |
| BMI1 | Rabbit | IgG | Abcam | H | CB |
| CD44 | Mouse | IgG2a | Abcam | H | CB |
| CD68 | Mouse | IgG3 | DAKO | H | CB |
| CK7 | Mouse | IgG1 | DAKO | H | CB |
| CK18 | Mouse | IgG1 | DAKO | H | CB |
| CK19 | Mouse | IgG2a | Abcam | H | CB |
| E-cadherin | Mouse | IgG2b | Abcam | H | CB |
| EpCAM | Mouse | IgG1 | Cell Signaling | H | CB |
| HepPar-1 | Mouse | IgG1 | DAKO | H | CB |
| KLF4 | Rabbit | IgG | NOVUS | H | CB |
| LGR5 | Rabbit | IgG | NOVUS | H | CB |
| MDR-1 | Mouse | IgG2a | Abcam | H | EDTA |
| MUC6 | Mouse | IgG1 | Santa Cruz | H | CB |
| NANOG | Mouse | IgG1 | Cell Signaling | H | EDTA |
| NCAM | Mouse | IgG1 | DAKO | H | CB |
| NGN3 | Rabbit | IgG | NOVUS | H | EDTA |
| OCT4 | Rabbit | IgG | Cell Signaling | H | EDTA |
| PDX1 | Rabbit | IgG | NOVUS | H | CB |
| SALL4 | Mouse | IgG1 | Abcam | H | EDTA |
| SHH | Rabbit | IgG | Millipore | H | CB |
| SOX2 | Rabbit | IgG | Cell Signaling | H | CB |
| SOX9 | Rabbit | IgG1 | SIGMA | H | CB |
| SOX17 | Mouse | IgG1 | Abcam | H | CB |
| SYNDECAN-1 (HS-PG-1) | Goat | IgG | R&D | H | CB |
| VCAM-1 | Mouse | IgG1 | Santa Cruz | H | CB |

H = human,
D = dog,
M = mouse,
P = pig,
R = rat.

1.13. Flow Cytometric Analyses.

The dissociated cells were incubated at 4° C. for 30 min with fluorescein isothiocyanate (FITC)- or biotin-conjugated anti-mouse-WIC class I (against H-2K$^d$) (clone; 34-1-2S) (eBioscience, San Diego, CA) and anti-human antibodies (see Table 3) for cell surface markers. For biotinylated antibody, allophycocyanin (APC)-streptavidin (BD Biosciences, San Jose, CA) was used for visualization. The cells were washed with staining medium before analysis. For the intracellular staining of LGR5, the cells were incubated with antibodies against the cell surface antigens as usual, and then, were fixed with 4% PFA/PBS at 4° C. for 20 min. After washing with staining medium, the cells were resuspended in permeabilization buffer (PBS with 1% FCS, 0.1% sodium azide, and 0.1% saponin) with PE-conjugated anti-LGR5 antibody at 4° C. for 30 min. Antibodies used are listed in Table 3. The labeled cells were washed with permeabilization buffer and then analyzed by FACSCalibur™. (BD Biosciences, San Jose, CA).

TABLE 3

Antibodies for Flow Cytometric Analyses

| Name | Clone | Host/isotype | Manufacture |
|---|---|---|---|
| APC-CD13 | WM15 | Mouse IgG1 | eBioscience |
| PE-CD24 | ML5 | Mouse IgG2a | BD Biosciences |
| FITC-CD29 (Integrin β1) | TS2/16 | Mouse IgG1 | eBioscience |
| APC-CD44 | BJ18 | Mouse IgG1 | BioLegend |
| FITC-CD49f (Integrin α6) | GoH3 | Rat IgG2a | BD Biosciences |
| FITC-CD54 (ICAM) | HA54 | Mouse IgG1 | BioLegend |
| APC-CD56 (NCAM) | MEM-188 | Mouse IgG2a | Abcam |
| FITC-CD90 (THY-1) | 5E10 | Mouse IgG1 | eBioscience |
| APC-CD117 (c-KIT) | YB5.B8 | Mouse IgG1 | BD Biosciences |
| APC-CD133/1 | AC133 | Mouse IgG1 | Miltenyi Biotec |
| APC-CD184 (CXCR4) | 12G5 | Mouse IgG2a | eBioscience |
| APC-CD324 (E-cadherin) | 67A4 | Mouse IgG1 | Miltenyi Biotec |
| FITC-CD326 (EpCAM) | VU-1D9 | Mouse IgG1 | Stem Cell Technologies |
| PE-TROP-2 | 77220 | Mouse IgG2a | R&D |
| PE-LGR5 | 2A2 | Mouse IgG1 | Origene |

APC, allophycocyanin;
PE, R-phycoerythrin;
FITC, fluorescein isothiocyanate.

1.14. Differentiation Assays.

$1 \times 10^5$ hFL-HCC cells, depleted of host mesenchymal cells by magnetic sorting, were seeded into each well of a 12-well plate coated with 5 µg/cm² hyaluronan and cultured with KM+2% FBS for overnight. After 16-20 hours, the cells were incubated for 7 days with either serum-free KM (as the undifferentiated control) or with serum-free HDM-H, HDM-C or HDM-P. After a total of 7 days culture, cells were harvested for analyses of gene expression.

1.15. Invasion Assay.

Invasion activity of the cells was analyzed using Cultre-Coat 96 Well BME-Coated Cell Invasion Optimization Assay Kit (TREVIGEN, Gaithersburg, MD) according to manufacturer's protocol. The hFL-HCC, depleted of host mesenchymal cells by magnetic sorting, or the human hepatocellular carcinoma cell line, Huh7 cells, were cultured with serum-free medium for starvation. After 20 hours of serum starvation, cells were collected. Then $2.5 \times 10^4$ cells were resuspended in 25 µl of serum-free Kubota's Medium (hFL-HCC) or serum-free DMEM (HuH7), and seeded into each well of a 96-well culture plates (top chambers). A total of 150 µl of each culture medium+10% FBS were added to the bottom chambers, and cells were cultured for 24 hours. After washing, cells were dissociated and fluorescently labeled with Cell Dissociation Solution/Calcein AM. After incubation at 37° C. for 1 hour, top chambers were removed and the absorbance at 485 nm excitation, 520 nm emission was measured.

1.16. Quantitative Reverse Transcription and Polymerase Chain Reactions (qRT-PCR).

Total RNA was extracted from the cells using RNeasy Micro Kit or RNeasy Mini Kit (Qiagen GmbH, Valencia, CA). First-strand cDNA synthesized using the Primescript 1st strand cDNA synthesis kit (Takara, Otsu, Japan) was used as a template for PCR amplification. Quantitative analyses of mRNA levels were performed using Power SYBR Green PCR Master Mix with Applied Biosystems 7500 Real-Time PCR System (Applied Biosystems, Foster City, CA). The primers were annealed at 50° C. for 2 min and 95° C. for 10 min, followed by 40 cycles of 95° C. (15 s) and 60° C. (1 min). Expression of glyceraldehyde-3-phosphate dehydrogenase (GAPDH) was used as a control standard. Primer sequences are listed in Table 4.

TABLE 4

Primers for qRT-PCR

| Name | F/R | Primer Sequence | Product length | GenBank Accession |
|---|---|---|---|---|
| CD44 | F | TGCCGCTTTGCAGGTGTAT | 66 | NM_000610.3 |
|  | R | GGCCTCCGTCCGAGAGA |  |  |
| CDH1 | F | TCACAGTCACTGACACCAACGA | 67 | NM_004360 |
|  | R | GGCACCTGACCCTTGTACGT |  |  |
| CFTR | F | AAAAGGCCAGCGTTGTCTCC | 170 | NM_000492.3 |
|  | R | TGAAGCCAGCTCTCTATCCCA |  |  |
| KRT7 | F | TGCTGCCTACATGAGCAAGGT | 99 | NM_005556.3 |
|  | R | TCTGTCAACTCCGTCTCATTGAG |  |  |
| KRT18 | F | GCCCGCTACGCCCTACA | 57 | NM_000224.2 |
|  | R | TGACTCAAGGTGCAGCAGGAT |  |  |
| KRT19 | F | CCGCGACTACAGCCACTACT | 97 | NM_002276.4 |
|  | R | GTCGATCTGCAGGACAATCC |  |  |
| LGR5 | F | GAGGATCTGGTGAGCCTGAGAA | 151 | NM_001277227.1 |
|  | R | CATAAGTGATGCTGGAGCTGGTAA |  |  |
| NANOG | F | AAATCTAAGAGGTGGCAGAAAAACA | 60 | NM_024865.2 |
|  | R | CTTCTGCGTCACACCATTGC |  |  |
| PDX1 | F | CCCATGGATGAAGTCTACC | 262 | NM_000209.3 |
|  | R | GTCCTCCTCCTTTTTCCAC |  |  |

TABLE 4-continued

Primers for qRT-PCR

| Name | F/R | Primer Sequence | Product length | GenBank Accession |
|---|---|---|---|---|
| POU5F1 | F | GAGAGGCAACCTGGAGAATTTG | 58 | NM_001173531.1 |
| | R | GATCTGCTGCAGTGTGGGTTT | | |
| PROM1 | F | TCCACAGAAATTTACCTACATTGG | 77 | NM_001145851.1 |
| | R | CAGCAGAGAGCAGATGACCA | | |
| SOX2 | F | AAATGGGAGGGGTGCAAAAGAGGAG | 112 | NM_003106.3 |
| | R | CAGCTGTCATTTGCTGTGGGTGATG | | |
| TACSTD1 | F | GACTTTTGCCGCAGCTCAGGAAG | 135 | NM_002354.1 |
| | R | GCCAGCTTTGAGCAAATGACAGTATTTTG | | |
| GAPDH | F | AAGGTGAAGGTCGGAGTCAA | 108 | NM_002046.3 |
| | R | AATGAAGGGGTCATTGATGG | | |

1.17. Cell Proliferation and Chemo-Resistance Assays.

For cell proliferation assays, $3 \times 10^4$ hFL-HCC cells of TU-2010 were depleted of host mesenchymal cells by magnetic sorting of xenotransplantable tumor cell suspension and then were seeded into each well of a 96-well plate and cultured overnight with Kubota's Medium+5% FBS. After 16-20 hours, the specific hedgehog inhibitor Vismodegib (GDC-0449) (Selleckchem Bio, Houston, TX) or the histone deacetylase (HDAC) inhibitors, suberic bis-hydroxamic acid (SBHA) or suberoylanilide hydroxamic acid (SAHA) (SIGMA, St. Louis, MO) were added for 3 days. Cell proliferation was evaluated using the Cell Proliferation Reagent WST-1 (Roche Applied Science, Mannheim, Germany). After incubation at 37° C. for 2 hours, the absorbance at 450 nm was measured.

1.18. Spheroid Formation Assays.

For spheroid formation assays, $1 \times 10^4$ hFL-HCC cells of TU-2010, depleted of host mesenchymal cells by magnetic sorting, were seeded into each well of a 6-well plate coated with Ultra-Low Attachment surface (Corning, Lowell, MA) and cultured with serum-free Kubota's Medium in the presence (or absence) of the specific hedgehog inhibitor Vismodegib (GDC-0449) or the HDAC inhibitors, SBHA or SAHA. For secondary spheroid formation assays, the 1st spheroids were collected, subsequently dissociated with NeuroCult Chemical Dissociation Kit (STEMCELL Technologies). Cell suspension was centrifuged at 700 rpm 10 min and resuspended with KM. After 2 weeks, the number of spheroids (100 μm>) were counted.

1.19. Transmission Electron Microscopy.

The hFL-HCC spheroids of Tu-210 were fixed with 3% glutaraldehyde in 0.15M sodium phosphate buffer, pH 7.4, for 1 hour at room temperature and stored at 4° C. until processed. Following three rinses with 0.15 M sodium phosphate buffer, pH 7.4, the samples were post-fixed for 1 hour with 1% osmium tetroxide/1.25% potassium ferrocyanide/0.15M sodium phosphate buffer, pH 7.4, followed by rinses in deionized water. The spheroids were dehydrated using increasing concentrations of ethanol (30%, 50%, 75%, 100%, 100%, 10 min each) and 2 changes of propylene oxide (15 min each). Following infiltration overnight in a 1:1 mixture of propylene oxide/Polybed 812 epoxy resin (Polysciences, Inc.) and 24 hours in 100% resin for 24 hours, the spheroids were embedded in fresh Polybed 812 epoxy resin. The spheroids were sectioned transversely at 70 nm using a diamond knife and a Leica Ultracut UCT microtome (Leica Microsystems, Wetzlar, Germany). Ultrathin sections were mounted on 200 mesh copper grids and stained with 4% aqueous uranyl acetate and Reynolds' lead citrate. The grids were observed at 80 kV using a LEO EM910 transmission electron microscope (Carl Zeiss SMT, LLC). Digital images were taken using a Gatan Orius SC 1000 CCD Camera with DigitalMicrograph 3.11.0 software (Gatan, Inc., Pleasantan, CA).

1.20. RNA-Sequencing and Gene Expression Analysis.

RNA was purified using Qiagen RNeasy Kit from human adult hepatocytes, hepatoblasts, hepatic stem cells, and biliary tree stem cells, each from three different donors, as well as four FL-HCC tumor samples of passaged TU-2010. In addition, RNA was purified from three cancer stem cell populations of the liver from tumors that are presumptive transformants of: (1) HpSCs, giving rise to hepatocellular carcinoma (HCC); (2) late stage (EpCAM+) BTSCs, giving rise to cholangiocarcinoma (CCA); and (3) primitive BTSCs (EpCAM−, CD44+), giving rise to fibrolamellar carcinoma (FLC). RNA integrity (RIN) analysis was performed using an Agilent 2000 Bioanalyzer. cDNA libraries were generated using the Illumina TruSeq Stranded mRNA preparation kit and sequenced on the Illumina HiSeq 2500 platform. Two samples were sequenced per lane, occupying a total of 8 lanes for all of the samples (one flow cell). Quality control analysis was completed using FastQC, mapping of sequence reads to the human genome (hg19) was performed with MapSplice2 using default parameters, transcript quantification was carried out by RSEM analysis, and DESeq was used to normalize gene expression and identify differentially expressed genes. MapSplice2 was also used to detect candidate fusion transcripts. Fusion calls were based on the depth and complexity of reads spanning candidate fusion junctions. Gene expression profiles were compared using Pearson's correlation analysis and hierarchical clustering was performed in R. Pathway enrichment analysis was performed with the Ingenuity Pathway Analysis (IPA) software.

Genes were determined to be differentially expressed between cancer types if they had >50 average normalized counts in at least one tumor type, exhibited >2-fold change, and had an adjusted p-value <0.05. Within the 163 genes found to be significantly differentially expressed in FLC compared to HCC or CCA, 16 genes were further identified for which the expression level in all FLC samples was greater than the expression level in 95% of HCC and 95% of CCA samples. The expression of these 16 genes was compared between a FLC patient-derived xenograft (PDX) model and normal biliary tree stem cells that were previously sequenced as described above. For RNA-seq analysis across 24 different tumor types, pre-processed RNA-seq data were downloaded from TCGA and plotted in R.

1.21. Normal Human Biliary Tree Stem Cells (hBTSCs).

The biliary tree contains stem cell niches, peribiliary glands (PBGs), mucinous glands scattered as intramural PBGs within the walls of the bile ducts and also found as extramural PBGs that are tethered to the bile ducts. The phenotypes of the cells within the PBGs can be relatively homogeneous in some sites (e.g. hepato-pancreatic common duct and intrahepatic, large bile ducts) and quite heterogeneous in other sites (e.g. cystic duct, common duct, hepatic duct). The pattern of phenotypic traits of the PBG cells was found to implicate maturational lineages in a radial axis from the fibromuscular layer within the duct walls to the lumen of the bile ducts and in a proximal (duodenum)-to-distal axis from the duodenum to either liver or pancreas.

The PBGs deepest within the bile ducts and near the fibromuscular layer contain the most primitive stem cells, those that co-express transcription factors for both liver and pancreas (e.g. SOX 17, PDX1) and that also co-express multiple pluripotency genes (e.g. OCT4, SOX2, KLF4, NANOG). These cells do not express epithelial cell adhesion molecule (EpCAM) or even LGR5. These are referred to as stage 1 biliary tree stem cells (hBTSCs) They transition to PBGs with cells expressing LGR5 (stage 2 hBTSCs) and then to ones positive for both LGR5 and EpCAM (stage 3 hBTSCs) found at levels that are intermediate within the bile ducts. With transition to the luminal surface of the ducts, there is acquisition of cells with mature phenotypic markers. If the ducts are near or within the liver, the mature markers are those for liver; if they are within the hepato-pancreatic common duct, the mature markers are pancreatic.

1.22. Cultures of Normal hBTSCs.

Figure 18:
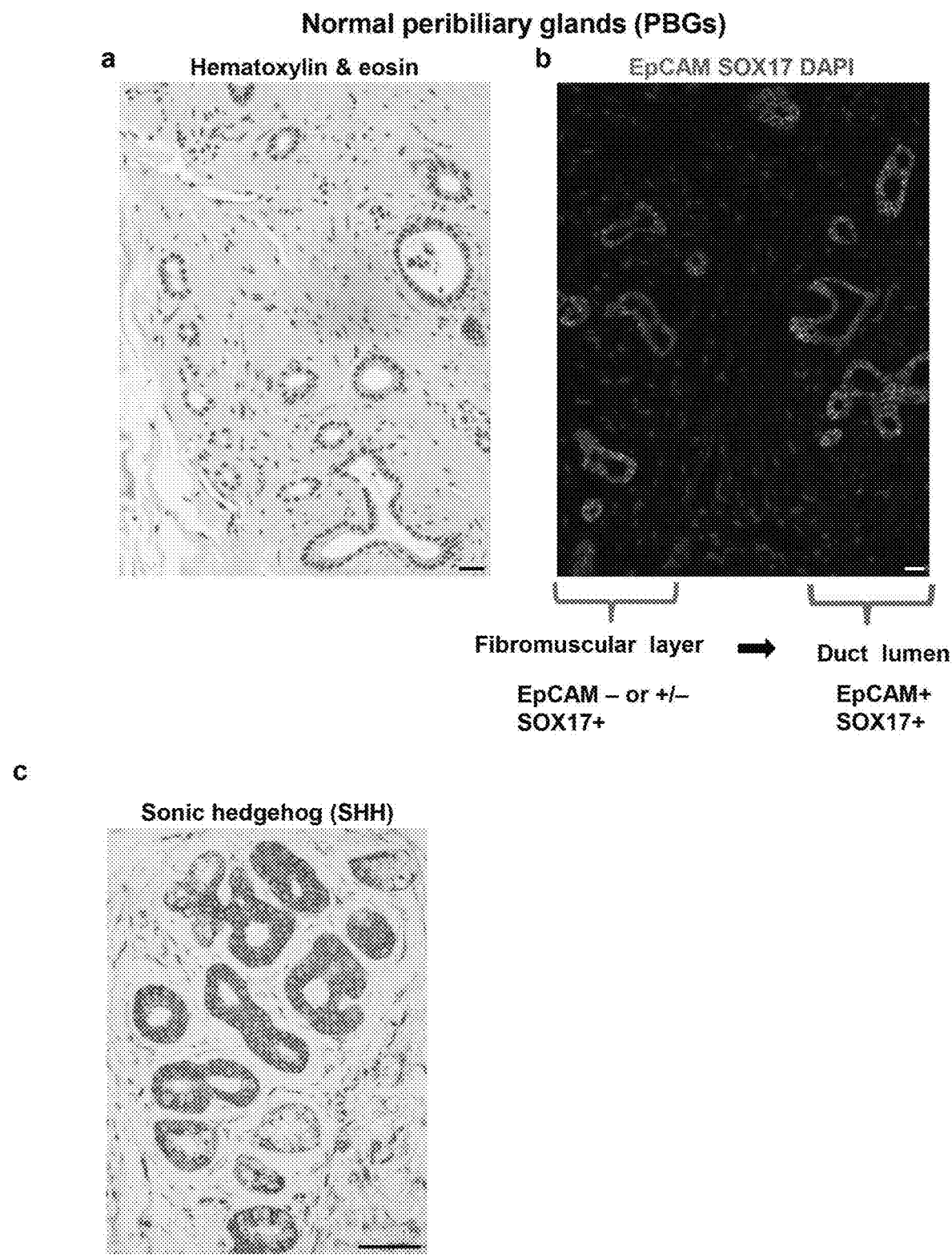
FIG. 18 shows images of normal peribiliary glands. The biliary tree is replete with peribiliary glands found throughout the duct wall (intramural glands) and others attached by tethers to the bile duct surface (extramural glands). Those within the duct wall contain cells of varying phenotypic traits that are found to be in a pattern indicating a maturational lineage. (a) Hematoxylin/eosin stained section of biliary tree and showing the peribiliary glands. (b) Radial axis of maturation lineage of biliary tree cells. The most primitive biliary tree stem cells (stage 1-hBTSCs) are located deep within the walls of the bile ducts and near the fibromuscular layer. These cells do not express LGR5 or EpCAM but do express pluripotency genes (e.g. OCT4, SOX2, KLF4, NANOG) and endodermal stem cell markers (e.g. SOX9, SOX17, PDX1). As one moves towards the lumen of the bile duct, the cells lose the stem cell traits and gradually acquire mature cell traits. At intermediate stages in this process, the cells acquire LGR5 (stage-2-hBTSCs) and then EpCAM (stage-3-hBTSCs). At the lumen, no stem cell traits are found but instead only markers of mature cells. If near the liver, those markers are hepatic; if near the pancreas, the markers are pancreatic; if in-between, the markers are those of bile ducts. (c) Sonic hedgehog expression in stage-3-hBTSCs. The scale bar=100 μm.
Figure 19:
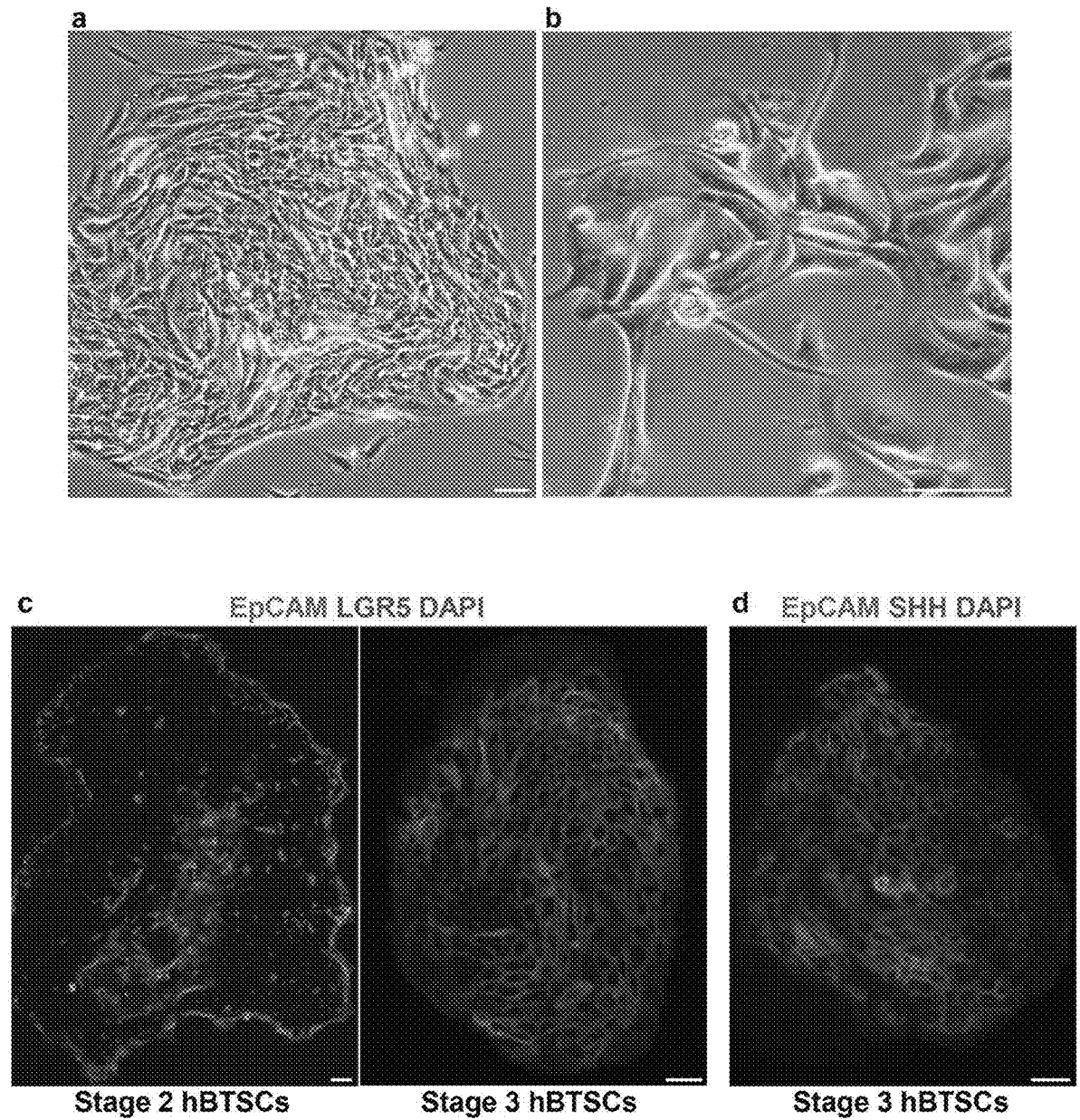
FIG. 19 shows images of cultures of normal biliary tree stem cells. Cultures of stage 2 of stage-3-hBTSC stages are achievable by plating onto culture plastic (or hyaluronans) and in serum-free Kubota's Medium. These conditions have not yet proven successful for stage-1-hBTSCs. Stage-2-hBTSCs form colonies of cells that are undulating and highly motile (a). They remain so in the cholangiocyte hormonally defined medium (HDM-C) as shown in (b). They do not express EpCAM (or CK19) on the cells within the centers of the colonies but have slightly larger cells at the perimeters of the colonies and that do express these traits (albeit muted relative to that seen in the stage-3-hBTSC colonies). (c) stage-3-hBTSCs form carpet-like colonies in which every cell expresses EpCAM (and also CK19). (d) The stage 2 and 3 colonies and the intermediates between them all express sonic hedgehog. The scale bar=50 μm.

The stage 1 hBTSCs have not yet been successfully cultured under the conditions tested. These have yet to be observed in culture under the conditions used. Two stages of hBTSCs that have been observed under the conditions used are stage 2 and 3 hBTSCs. See FIGS. 18 to 20. The stage 3-hBTSC colonies strongly express both LGR5 and EpCAM in every cell and form colonies of relatively uniform, cuboidal shaped cells that are tightly bound to each other. They are distinct from stage 2-hBTSCs that are undulating, swirling cells that can form extensions, are highly motile and have variable connections with neighboring cells. These colonies strongly express LGR5 throughout all of the cells, but are devoid of EpCAM expression on the interior of the colonies and yet express it at their edges in cells that are slightly larger and more differentiated. Treatment of the stage 2 hBTSC colonies with any of several different growth factors (e.g. EGF, HGF) or with laminin results in rapid transition to stage 3 hBTSCs with activation of expression of EpCAM throughout the colony. The net results indicate that the stage 2-hBTSCs [LGR5+, EpCAM –negative cells], are precursors of the stage 3-hBTSCs (LGR5+, EpCAM+].

A summary of phenotypic traits of biliary tree stem cells versus hepatic stem cells is given in Table 5. They indicate that the lineages of biliary tree stem cells are precursors of hepatic and pancreatic stem cells and are assumed to contribute to organogenesis of liver versus pancreas. A chart of the lineage stages identified is given in FIG. 20. The cells in the hFL-HCC tumor line, TU-2010, are most closely similar to the stage 2-hBTSCs.

TABLE 5

Phenotypic Profile of Normal Stem Cells in Liver and Biliary Tree and of Pancreatic Committed Progenitors Versus Human Fibrolamellar Hepatocellular Carcinoma Cells (hFL-HCC) of the TU-2010 tumor line

| | Liver | | | → Pancreas | |
|---|---|---|---|---|---|
| Property | hHpSCs (in Canals of Hering) | hBTSC Subpopulations (in peribiliary glands) | | Committed Progenitors (in Pancreatic Duct Glands) | hFL-HCC Cells of TU-2010 |
| Endodermal markers | SOX 9, LGR5, HNF4A, FOXL1 | SOX 9, SOX17 LGR5 FOXL1 HNF4A | SOX 9, SOX17, PDX1 FOXL1 HNF4A | SOX 9, PDX1 LGR5 FOXL1 HNF4A | PDX1, LGR5 | SOX 9, SOX17, PDX1, LGR5, FOXL1, HNF4A |
| Markers of Epithelia | | CK 8 and 18, CK 7 and 19, E-cadherin | | | | |
| Cell Adhesion Molecules | NCAM, EpCAM+ ITGB1 (CD29) | NCAM, EpCAM+ ITGA6 (CD49f), ITGB4, ITGB1 (CD29) | NCAM EpCAM– | NCAM, EpCAM+ | EpCAM+ | NCAM, VCAM, EpCAM± (negligible) ITGA6 (CD49f), ITGB4, ITGB1 (CD29) |
| Pluri- potency Genes | OCT4, SALL4, NANOG | KLF4/KLF5, NANOG, OCT4, SALL4, TROP-2, BMI1 | | | None | KLF4/KLF5, OCT4, NANOG, SALL4, BMI1 |
| Other Stem Cell Markers | CXCR4, CD133, Hedgehog proteins (Indian, Sonic), ALDH | CXCR4, CD133; and Hedgehog proteins (Indian and Sonic), ALDH | | | None | CD133, Sonic Hedgehog, ALDH |

TABLE 5-continued

Phenotypic Profile of Normal Stem Cells in Liver and Biliary Tree and of Pancreatic Committed Progenitors Versus Human Fibrolamellar Hepatocellular Carcinoma Cells (hFL-HCC) of the TU-2010 tumor line

| | Liver | | → Pancreas | |
|---|---|---|---|---|
| Property | hHpSCs (in Canals of Hering) | hBTSC Subpopulations (in peribiliary glands) | Committed Progenitors (in Pancreatic Duct Glands) | hFL-HCC Cells of TU-2010 |
| Protein Matrix components Receptors | Laminin, type III collagen, Oncostatin M receptor | Laminin, Oncostatin M receptor | Fetal islets: collagens IV, V, VI, Laminin, Nidogen, elastin, fetal acinar cells: fibrillar collagens, fibronectin | Laminin, Oncostatin M receptor, CD68 |
| GAGs/PGs | Minimally sulfated CS-PGs, Hyaluronans | Hyaluronans, CD44. | Hyaluronans, CD44, fetal islets have syndecans (HS-PG-1 and 3), glypicans, fetal acinar cells have CS-PGs | Hyaluronans, CD44, Syndecan-1 (HS-PG-1) |
| Liver-specific traits | Albumin+/−, AFP−, HNF4A, HepPar1+, KRT7, DLK1 | KRT7, HNF4A | None | AFP−, HNF4A HepPar-1+; KRT7 |
| Pancreatic-specific traits | PDX1 | PDX1 / PDX1, ISL1, NGN3 | PDX1, NGN3, MAFA, MUC6, Nkx6, PTF1a, GLUT2 | PDX1, KRT20, NGN3 |
| Multidrug resistance genes | | MDR-1, ABCG2 | None | MDR-1 ABCG2 |

Experimental Results.

Endodermal Stem/Progenitor Markers were Expressed in hFL-HCCs.

Sections from original blocks of 9 hFL-HCC tumors from Memorial Sloan Kettering Cancer Center (MSKCC) were subjected to IHC assays (FIGS. 1 and 7). All sections assayed were positive for HepPar-1 and SHH. Positive expression was also observed in 7/9 for SOX9 and PDX1 and 4/9 for BMI1.

Figure 8:
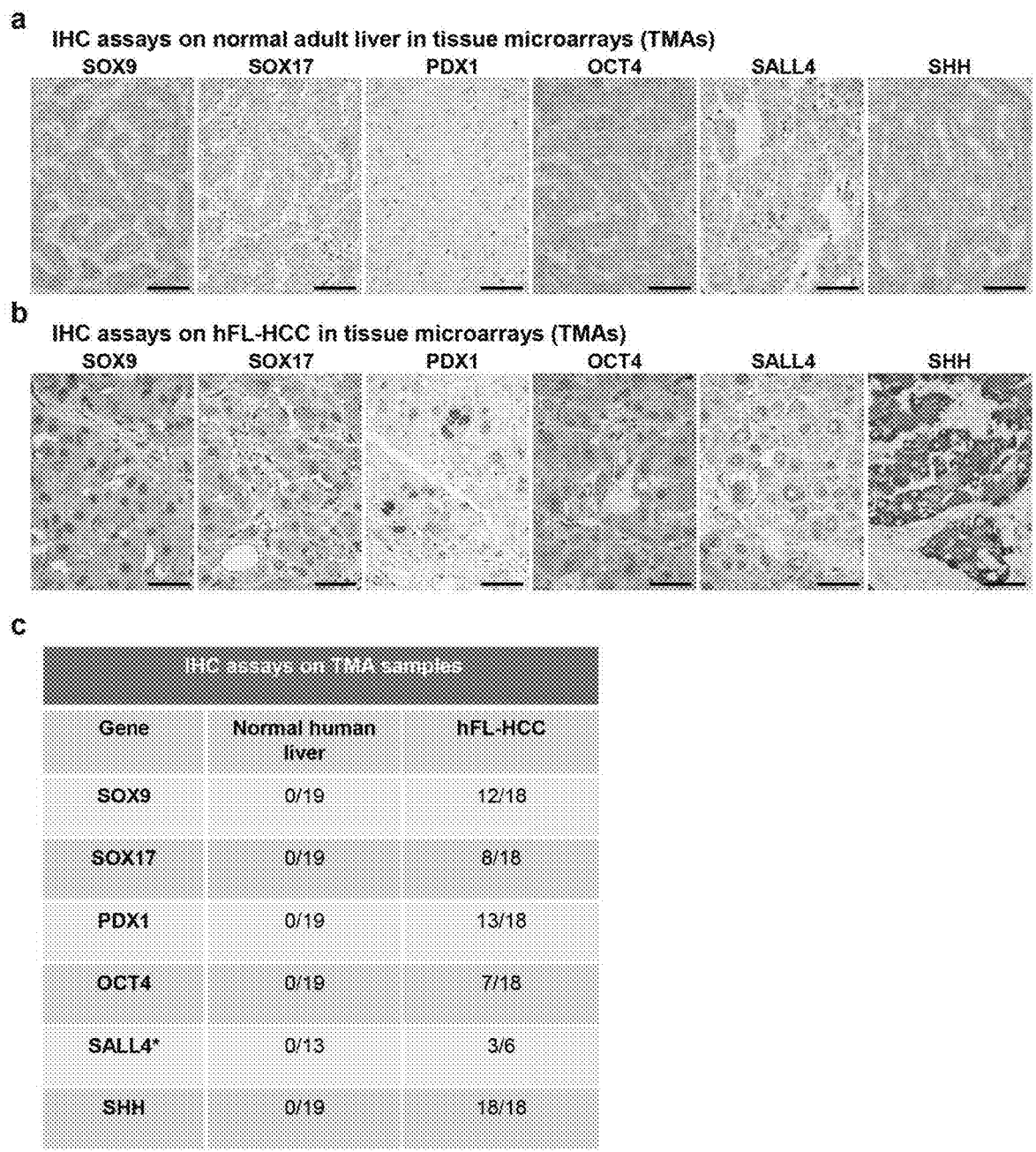
FIG. 8 shows the results of IHC assays on the TMA samples of 18 hFL-HCCs versus 19 normal livers. (a) Tissue microarrays (TMAs) of normal human liver versus (b) a human fibrolamellar hepatocellular carcinomas (hFL-HCC). (c) Table with summary of the number of positive versus negative assays on the TMA samples. *With SALL4 staining, some paraffin sections were lost due to the buffer conditions used for antigen retrieval. The scale bar=25 μm.

Tissue microarrays (FIG. 8) from Memorial Sloan Kettering Cancer Center (MSKCC) provided additional evidence from primary tumors. Whereas stem/progenitor traits were not observed in any of the 19 normal livers, all hFL-HCCs were positive for multiple stemness markers: SOX9 (12/18), SOX17 (8/18), OCT4 (7/18), SALL4 (3/6), SHH (18/18), and PDX1 (13/18).

A Transplantable hFL-HCC Tumor Line, TU-2010, was Established Successfully by Use of Culture-Selected Endodermal Stem/Progenitors.

A young, male patient was diagnosed with FL-HCC and was subjected to liver surgery and chemotherapies, all of which proved unsuccessful (Table 1). Within 2 years, the tumor had metastasized and generated ascites tumor cells. Approximately 5 liters of ascites fluid were removed from the patient. Cells from one liter were immediately transplanted into immune-compromised mice, but no tumors formed. Cells from the remaining 4 liters were subjected to culture selection in Kubota's Medium (KM) for endodermal stem/progenitors, and $2 \times 10^7$ cells were transplanted into nod scid gamma (NSG) mice. Tumor formation occurred after >6 months.

Passaging of hFL-HCC of TU-2010 was Stabilized by Supplements and Occurred with Different Kinetics in Subcutaneous Versus Intraperitoneal Sites.

Figure 2:
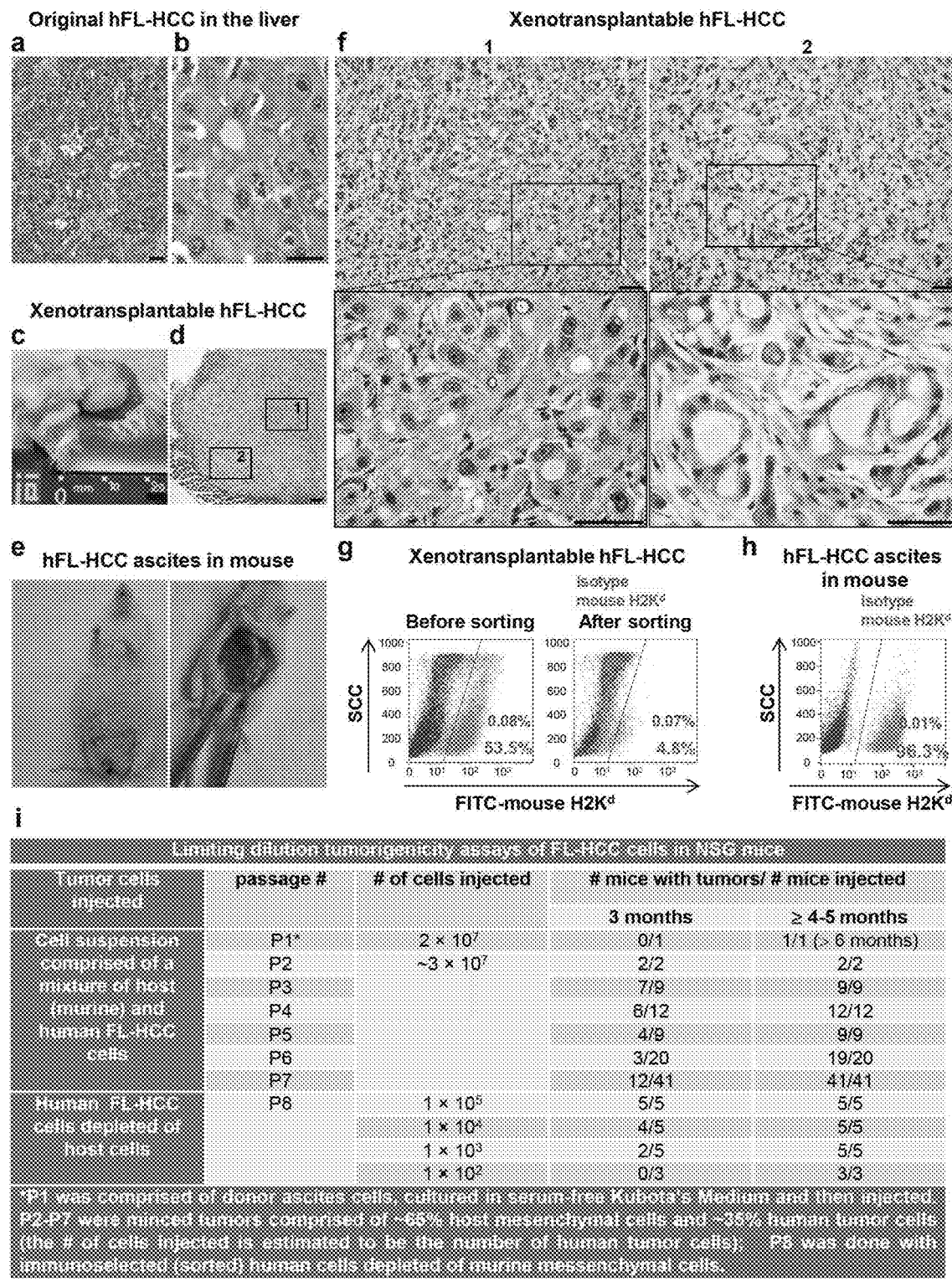
FIG. 2 shows the characterization and tumorigenicity of the transplantable human FL-HCC tumor line, TU-2010. (a, b) Hematoxylin/eosin stained sections of the original solid tumor found in the liver. (c, d) Subcutaneous tumor generated in NSG mice. (e) Intraperitoneal transplants. (f) Histology of the centers (1) versus perimeters (2) of the subcutaneous tumor at low and high magnifications. Histology and IHC assays on the original hFL-HCC cells from the ascites tumor of TU-2010 are given in FIG. 9a. The scale bar=25 (g) Proportion of human tumor cells to host cells in subcutaneous tumors. Flow cytometric analyses of tumors dispersed into single cell suspensions indicated that the cell suspensions were over 50% and up to 70% host cells. Shown is one in which the cell suspension was comprised of 53.5% murine mesenchymal cells and the remainder are human tumor cells. By negatively sorting for cells positive for $H-2K^d$, the enrichment of the human tumor cells reached above 95% routinely. (h) Proportion of human tumor cells to host cells in intraperitoneal tumors of TU-2010. With intraperitoneal transplantation the passaging can be done every about 8 weeks. Flow cytometry contrasting side scatter (SCC) versus expression of $H-2K^d$ in hFL-HCCs derived from the ascites cells from the peritoneum of mice. The murine ascites fluid and the cells bound to the serosal surfaces comprise about 3.5% tumor cells and over 96% host cells indicating the extraordinary extent of desmoplastic response with intraperitoneal transplants. (i) Limiting dilution tumorigenicity assays of hFL-HCCs from TU-2010. The original tumor sample includes 4 liters of ascites tumor cells that were centrifuged, plated onto culture plastic and in serum-free Kubota's Medium (KM) for several weeks. Phase images of the original cultures are given in FIGS. 4a and 4b (see also FIG. 10). Culture selection for endodermal stem/progenitors was performed. The tumors from the initial passage appeared in about 5 months. Subsequently tumors appeared by about 3 months if about $10^6$ to $10^7$ tumor cells were transplanted in KM supplemented with hyaluronans, HGF and VEGF. At passage 8, the tumor cells were dispersed, and the host mesenchymal cells depleted by sorting negatively for cells positive for $H-2K^d$. The purified hFL-HCC cells were transplanted subcutaneously at cell numbers from $10^2$ to $10^6$. At all concentrations from $10^5$ cells and higher tumors formed in 100% of the mice by 3 months; at $10^3$-$10^4$ cells, all formed tumors within 4-5 months. At 100 cells, one tumor formed at 5 months; one at 6 months; and one by 9 months.

Tumors were passaged every 3-5 months and stabilized at about 3 months with transplantation of about $10^6$ cells in KM supplemented with 1 mg/ml hyaluronans and with 50 ng/ml each of hepatocyte growth factor (HGF) and vascular endothelial cell growth factor (VEGF) (FIG. 2). The passageable, subcutaneous tumors were nodular and difficult to mince. If transplanted intraperitoneally (FIGS. 2e and 2h), ascites tumors formed, requiring passaging every about 8 weeks and giving rise to nodules on serosal surfaces throughout the peritoneum and on liver and pancreas.

Histology of Xenografted Tumor Cells of TU-2010 Matched that of the Original Tumor.

The histology of the original tumor (FIG. 2a-2b) and of the ascites tumor cells (FIG. 9a) versus those of xenografts (FIG. 3d-3g and FIG. 9b) revealed differences between the tumor centers (FIGS. 2d1 and 2f1) and their perimeters (FIGS. 2d2 and 2f2), sites at which tumors interfaced with host tissues. Tumor centers demonstrated histology similar to that of the original tumor with large polygonal cells, abundant eosinophilic cytoplasm, large, vesiculated nuclei and large nucleoli. By contrast, the histology at tumor perimeters comprised incomplete ductular structures with partially stabilized lumens and with features similar to those of intrahepatic, mixed-type cholangiocarcinomas (CCs) with ductular areas.

The FL-HCC Tumors of TU-2010 were Comprised Primarily of Host Cells.

Mesenchymal cells within tumors were a mix of precursors to stellate cells (desmin+, alpha-smooth muscle actin+) and endothelia (CD31+) and comprised, on average, 55-70% of cell suspensions from subcutaneous tumors and >95% of those from intraperitoneal tumors (FIG. 2g). Enrichment of hFL-HCCs to ≥95% (FIG. 2h) was achieved by negative sorting using magnetic bead immunoselection to eliminate murine cells, ones positive for H-2K$^d$ (FIG. 2g). Tumors contained, on average, about 8×10$^6$ hFL-HCC cells/gm of tumor.

Expression of Stem/Progenitor Markers in TU-2010 Cells was Confirmed by Flow Cytometry.

Figure 3:
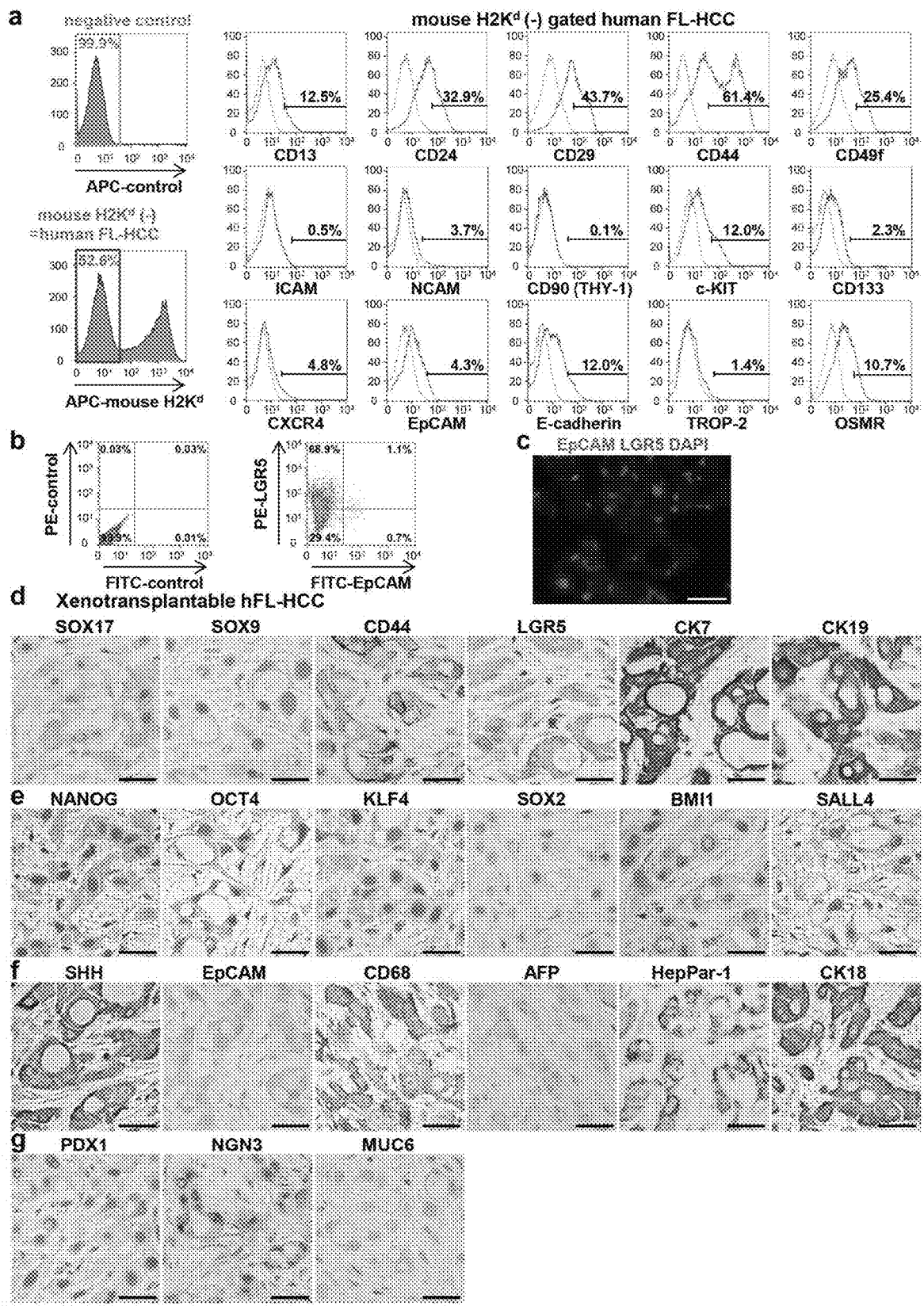
FIG. 3 shows the results of IHC and flow cytometric assays on the xenotransplantable tumor line, TU-2010. (a) Representative FACS characterizations of sorted hFL-HCC cells (cell suspensions depleted of murine host cells) from TU-2010. LGR5$^+$ cells accounted for 68.9% of the cells in the tumors. Other antigens that were expressed by a significant percentage of the cells from TU-2010 included CD44, the hyaluronan receptor (61.4%); CD49f (25.4%); Signal transducer CD24 (32.9%); CD13, alanine aminopeptidase (12.5%); c-KIT (12.0%); E-cadherin (12.0%); and oncostatin M receptor (OSMR) (10.7%). Other antigens found routinely in a smaller percentage of cells included CXCR4, also called fusin or CD184 (4.8%), EpCAM (4.3%), CD133, also called prominin (2.3%), TROP-2 (1.4%); and ICAM intercellular adhesion molecule (0.5%). (b) The hFL-HCCs of TU-2010 were depleted of murine cells and sorted for LGR5$^+$ cells by flow cytometry. Of these, only 1.1% were also EpCAM$^+$. (c) IHC assay on the sorted LGR5$^+$ cells demonstrated strong expression of LGR5 and an absence of EpCAM. (d, e, f, g) Paraffin sections (5 μm) from hFL-HCC tumors (subcutaneous) were prepared and subjected to IHC assays for an array of antigens. Of those shown, all were positive with the exceptions of EpCAM, alpha-fetoprotein (AFP), and MUC6. The survey comprised assays for endodermal stem/progenitor transcription factors and markers: SOX17, SOX9, CD44, LGR5, CK7 and CK19 (d); pluripotency genes and genes indicative of self-replication: NANOG, OCT4, KLF4, SOX2, BMI1 and SALL4 (e); hepatic and other markers: SHH, EpCAM (essentially negative), CD68, HepPar-1, CK18, AFP (negative) (f); and pancreatic/endocrine markers: PDX1, NGN3, and MUC6 (negative), which was strongly expressed (g). CD68 is a marker identified previously as routinely found in hFL-HCC cells. Additional assays and controls are given in FIG. 9b. The scale bar is 25 μm for all Figure panels.

Immunoselected hFL-HCCs, depleted of murine cells, were characterized by multiparametric flow cytometry (FIG. 3a-3b). The majority of cells were positive for LGR5 (68.9%) and CD44 (61.4%); a significant percentage were positive for CD29 (43.7%), CD24 (32.9%), CD49f (25.4%), CD13 (12.5%), E-cadherin (12.0%), c-KIT (12.0%) and oncostatin M receptor-OSMR (10.7%). A low but consistent percentage of cells were positive for NCAM (3.7%), EpCAM (4.3%), CXCR4 (4.8%), CD133 (2.3%), TROP-2 (1.4%) and ICAM (0.5%). A small percentage (1.1%) of LGR5+ cells were positive for EpCAM.

The hFL-HCCs of TU-2010 were Rich in Cancer Stem Cells (CSCs) as Indicated Functionally by Limiting Dilution Tumorigenicity Assays.

Cell suspensions were depleted of murine cells and transplanted subcutaneously into NSG mice in tumorigenicity assays from 100 to 10$^6$ cells and monitored for up to 8 months for tumors. Transplantation of 10$^5$ or more cells resulted in 100% of the mice developing tumors within about 3 months; 10$^3$-10$^4$ cells within 5-6 months; and 100 cells in all mice but requiring up to 9 months (FIG. 2i).

Xenografted hFL-HCCs of TU-2010 Expressed Endodermal Stem/Progenitor Markers that Collectively Suggest Derivation from Biliary Tree Stem Cells (hBTSCs).

Sections of xenografted hFL-HCCs were subjected to IHC assays (FIG. 3d-3g and FIG. 9b) and the findings compared to those from original tumor cells (FIG. 9a). The hFL-HCCs were positive for CD68, a previously observed feature of hFL-HCCs; stem/progenitor markers (SOX17, SOX9, LGR5, SHH, NCAM, BMI1); pluripotency traits (NANOG, OCT4, KLF4, SOX2, SALL4); some hepatic markers (HepPar-1,CK7,CK19,CK18); and pancreatic markers (PDX1). They were essentially negative for albumin, alpha-fetoprotein (AFP), MUC6, and weakly positive for EpCAM (FIG. 3f). The markers were suggestive of highly aggressive tumors.

Figure 20:
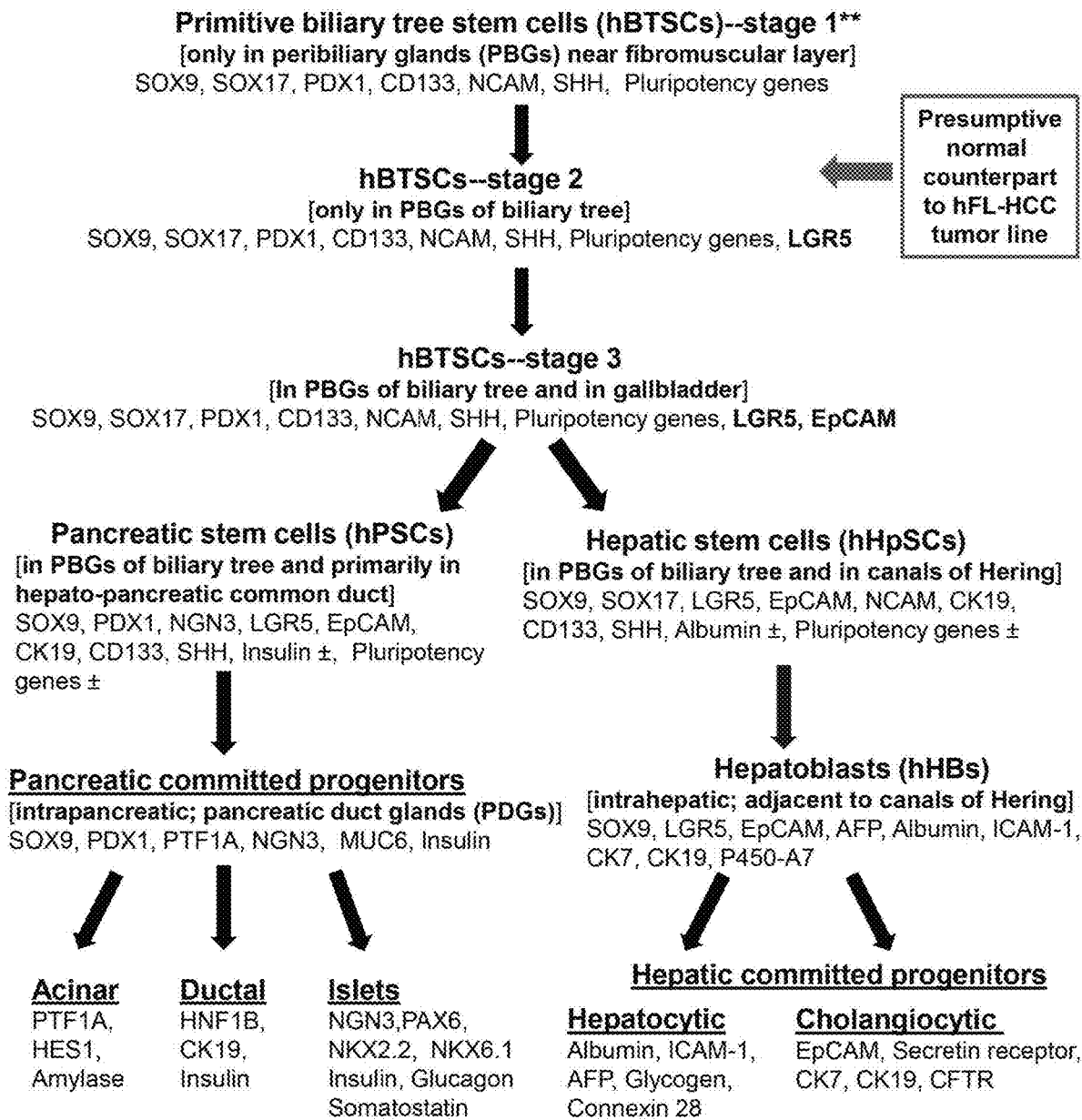
FIG. 20 shows a chart of known biliary tree stem cell populations and their lineage connections and the probable normal counterpart to the hFL-HCC tumor cells from the transplantable tumor line, TU-2010.

Other markers (FIG. 9b) in TU-2010 cells included some multidrug resistance genes and matrix components that facilitate cell survival and growth: E-cadherin; syndecan-1 (HS-PG1); hyaluronan receptors (CD44); and vascular cell adhesion molecule-1 (VCAM-1). The cells did not express hemopoietic (CD34, CD45), stellate (CD146) or endothelial cell antigens (CD31). Negative controls are shown in FIG. 9b. A summary of in situ analyses of hFL-HCC cells as well as normal human hepatic stem cells (hHpSCs), hepatoblasts (hHBs) and hBTSCs is provided in Table 5 and in FIGS. 18-20. The hFL-HCC tumor most closely resembled stage-2-hBTSCs (FIG. 20).

The hFL-HCC Cells of TU-2010 in Culture Behaved Similarly to Normal hBTSCs.

Figure 4:
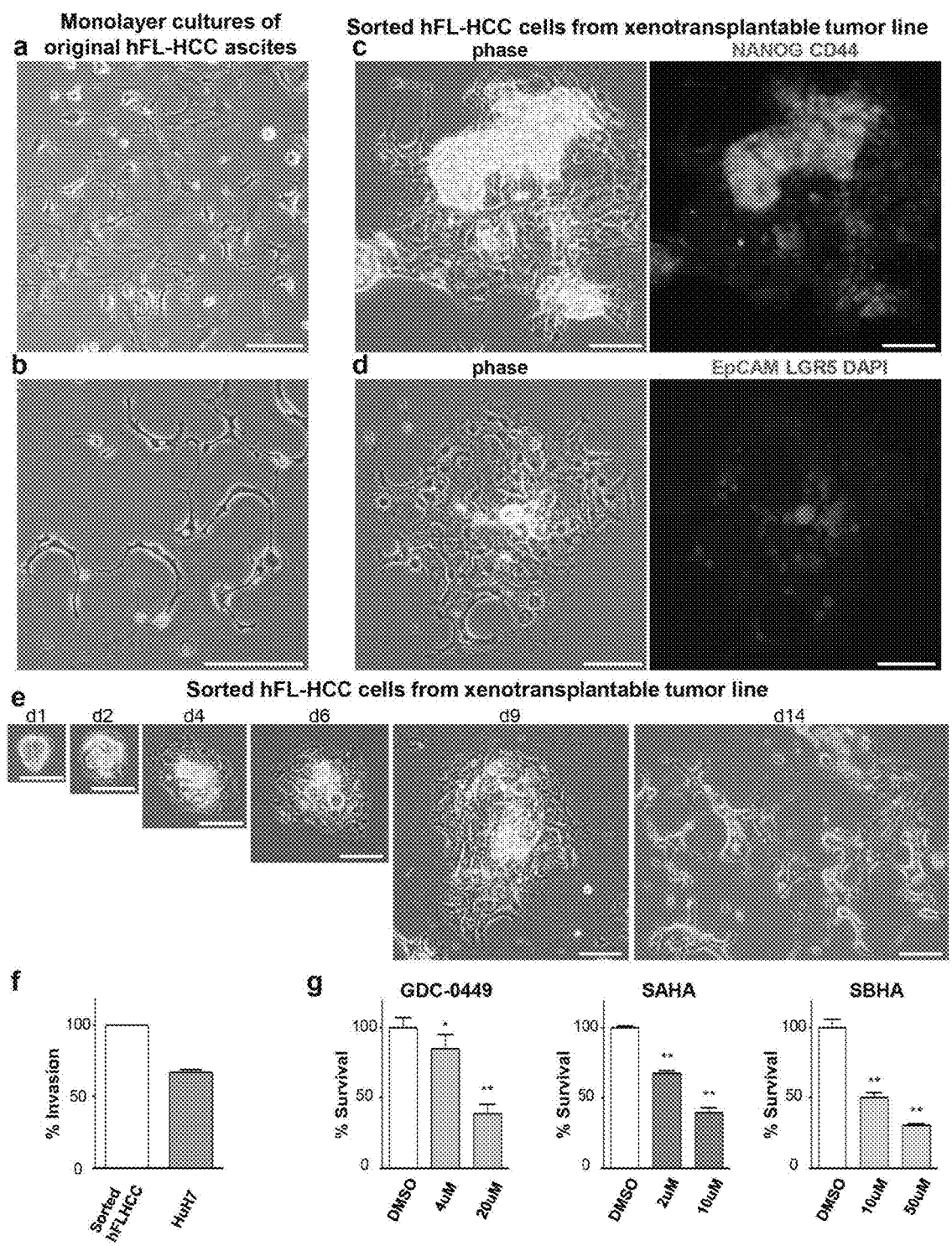
FIG. 4 shows analysis of monolayer cultures of hFL-HCC cells from TU-2010. (a) Suspensions of hFL-HCC cells from TU-2010 were plated onto culture plastic and in serum-free KM. The cells transiently attached and formed star-like cells (see also FIG. 11). (b) Subsequently, the cells became loosely attached to the dish and retained attachment to each other via E-cadherin linkages such that they formed floating cell chains ("catena"). (c) If plated with KM supplemented with 2-5% FBS during the seeding phase and then converted to serum-free KM, the cells were able to remain attached to the dishes for longer and formed colonies that were irregular and with extensions in diverse directions; they transitioned into aggregates/spheroids that eventually floated into the medium. (d) IHC of these colonies indicated that they were uniformly positive for stem cell traits such as LGR5 or NANOG. (e) The aggregates, but not monolayer cells, expressed low levels of EpCAM and cytokeratin19. Depletion of the host (murine) cells enabled hFL-HCC cells to form colonies at single cell seeding densities and that grew into colonies within 2 weeks. After 2 weeks, these cells morphologically resemble the cultures of the original ascites cells. The scale bar is 100 μm (a-e). (f) Using assays comparing invasion through filters coated with a basement membrane matrix versus uncoated filters, 100% of the hFL-HCCs from TU-2010 were able to invade compared to less than about 70% of Huh7 cells, a liver cancer cell line. (g) A screen of drug effects on monolayer cultures indicated that the hedgehog inhibitor, GDC-0449, had effects at 4 μM and especially at 20 μM to suppress survival and proliferation of hFL-HCC cells. Histone deacetylase (HDAC) inhibitors were more potent: SBHA at 10 μM and 20 μM and especially SAHA at 2 μM and 10 μM, had strong inhibitory effects on hFL-HCC cell survival and growth. Data are expressed as the mean±SD (**$p<0.01$,*$p<0.05$).
Figure 5:
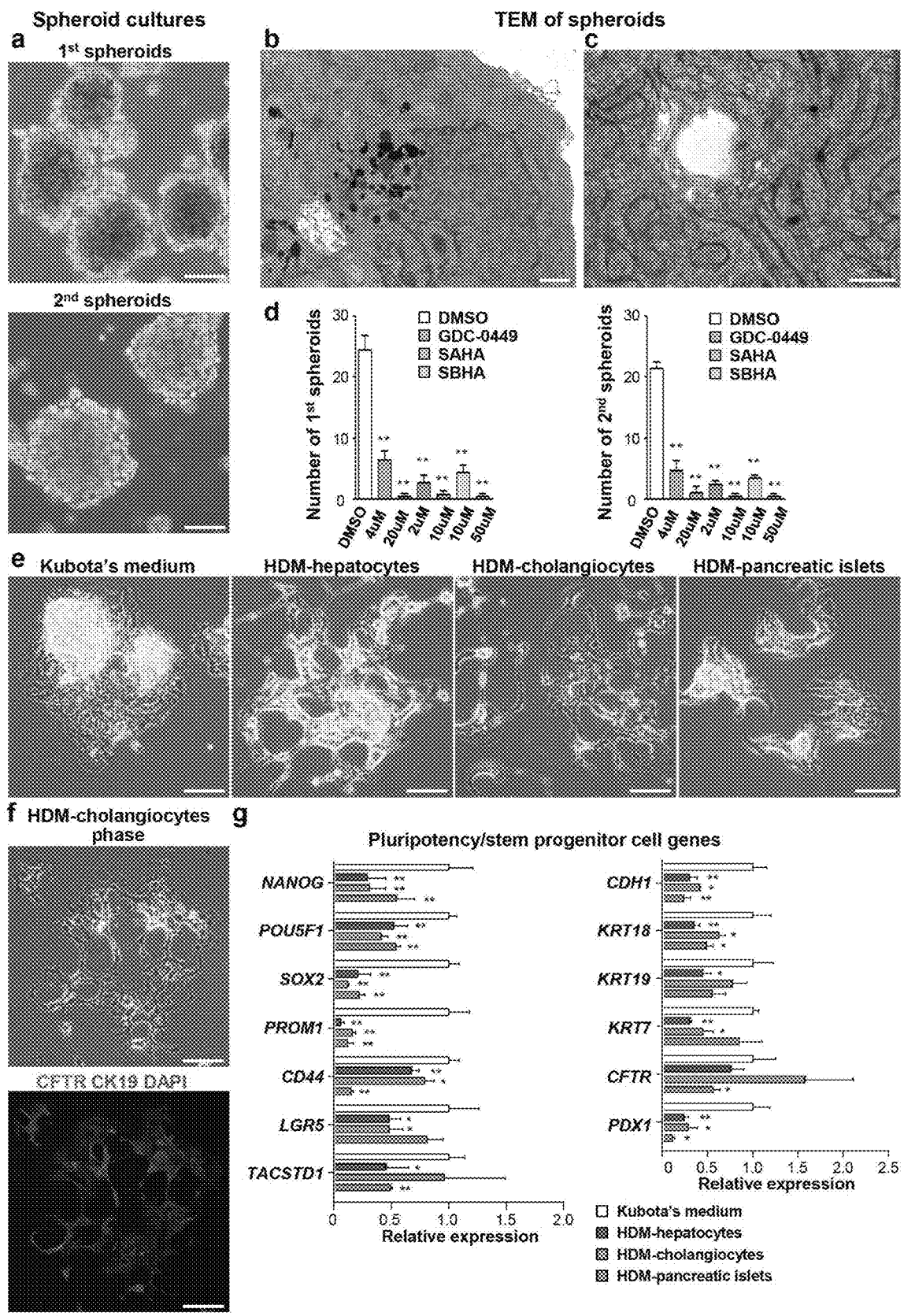
FIG. 5 shows analysis of spheroid cultures of the hFL-HCC cells from TU-2010. Plating the hFL-HCC tumor cells from TU-2010 in serum-free conditions on low attachment plates, and especially after depletion of the murine cells, resulted in spheroid formation. (a) The spheroids that formed from freshly isolated hFL-HCC cells from TU-2010 and that were depleted of murine cells (1$^{st}$ spheroids) were sustainable in culture for months and were able to be passaged to form secondary spheroids (2$^{nd}$ spheroids). The scale bar is 100 μm. (b, c) Transmission electron micrographs (TEM) of the spheroids from TU-2010 (see also FIGS. 11 and 12) indicate cell aggregates with some cell adhesion mechanisms; large numbers of secretory vesicles with electron-dense granules; partially formed ducts; and a wealth of mitochondria with aberrant cristae. The scale bar is 1 μm. (d) The HDAC inhibitors and GDC-0449 were far more effective at strongly suppressing hFL-HCC survival and growth of the spheroid cultures than when the cells were in monolayer cultures. Data are expressed as mean±SD (p<0.01). (e) KM resulted in maintenance of stemness in the cells. The differentiation media comprised serum-free hormonally defined medium (HDM) tailored for lineage restriction of normal hBTSCs to hepatocytes (HDM-H), cholangiocytes (HDM-C) or pancreatic islets (HDM-P). These media were able to partially differentiate the hFL-HCCs from TU-2010; full maturation was not achieved due to the matrix-degrading enzymes produced by the tumor cells, which induced rapid dissolution (within hours) of every matrix substratum tested. The morphology of the colonies in KM versus the several differentiation media are shown. The changes occurred were transient, as the cells transitioned rapidly towards spheroid formation. (f) During the few days when morphological changes were observed, there was an increase in expression of some markers associated with maturation to an adult fate. The example shown is CFTR, a trait of maturing or mature cholangiocytes. The scale bar is 100 μm. (g) qRT-PCR assays showed that stem cell traits (NANOG, POU5F1, SOX2, PROM1) were suppressed in all the HDM. Surprisingly, so were KRT18 and PDX1 and to a lesser extent KRT7. CD44 was partially suppressed in HDM-H and HDM-C but strongly suppressed by HDM-P; LGR5 was suppressed in HDM-H and HDM-C but not in HDM-P; TACSTD1 (EpCAM), KRT19, and CFTR were modestly suppressed in HDM-H and HDM-P, but EpCAM and especially CFTR were actually elevated in HDM-C, and KRT19 was not affected. Data are expressed as mean±SD (p<0.01, *p<0.05).
Figure 11:
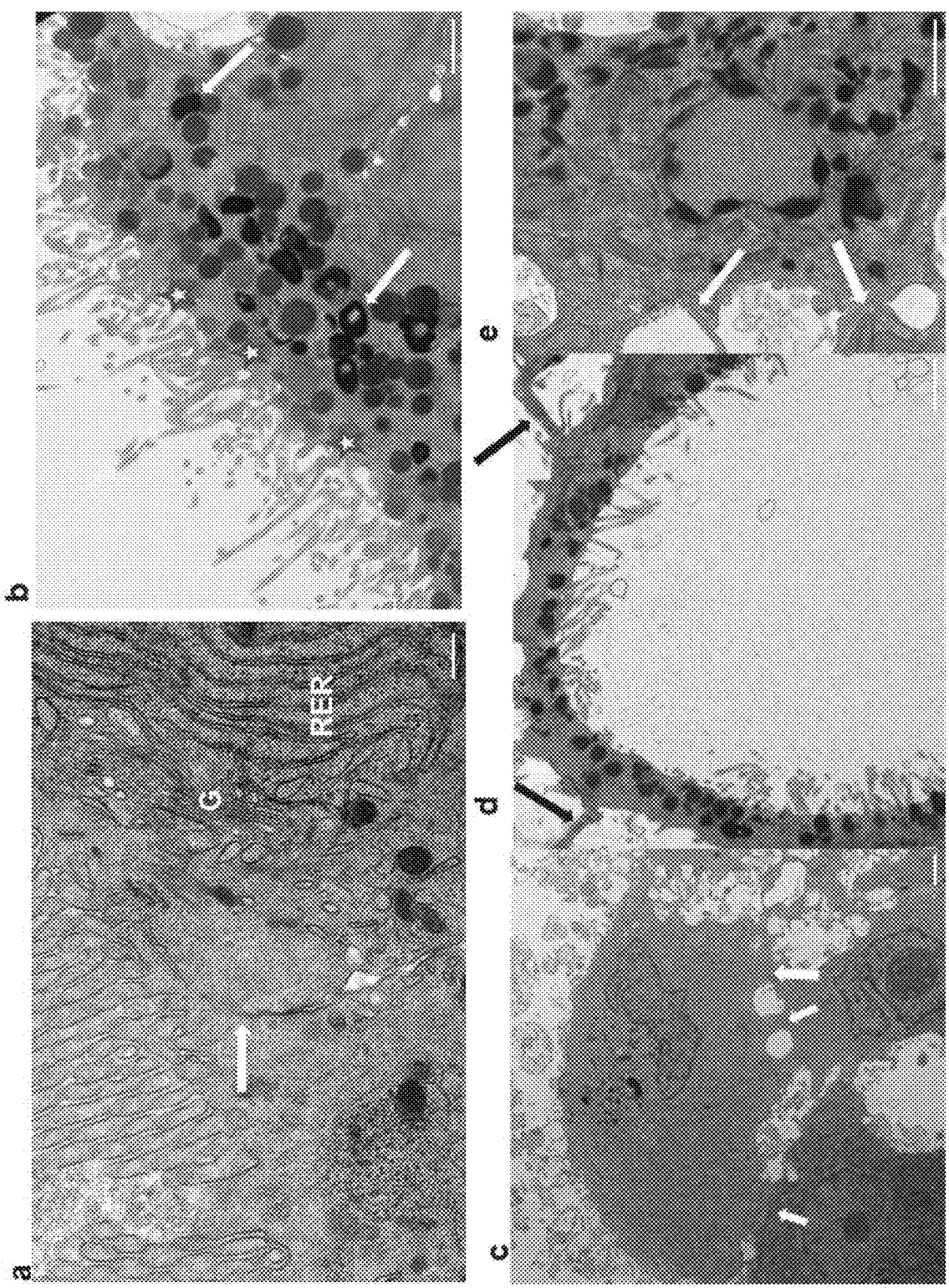
FIG. 11 shows TEM images of hFL-HCC spheroids from TU-2010 plated and maintained in serum-free KM. (a) Tumor cells displayed numerous microvilli at their apical pole and tight junctions (arrow) at cell to cell contact, meaning the tumor cells could still polarize. Cells were rich in rough endoplasmic reticulum (RER) and Golgi apparatus (G). (b) At their apical pole, tumor cells had numerous secretory vesicles containing electron-dense (white arrows) or not electron-dense (asterisks) granules. Note the presence of microvilli. (c, d, e) Tumor cells were connected with tunneling nanotubes (TNT: dark arrows in c); Filopodia-like protrusions, which proceed TNT formation, were present and established physical contact with neighboring cells (arrows in d and e). The scale bar correlates with different lengths in the different images: The scale bar=200 nm (a), 1 μm (b-e).
Figure 12:
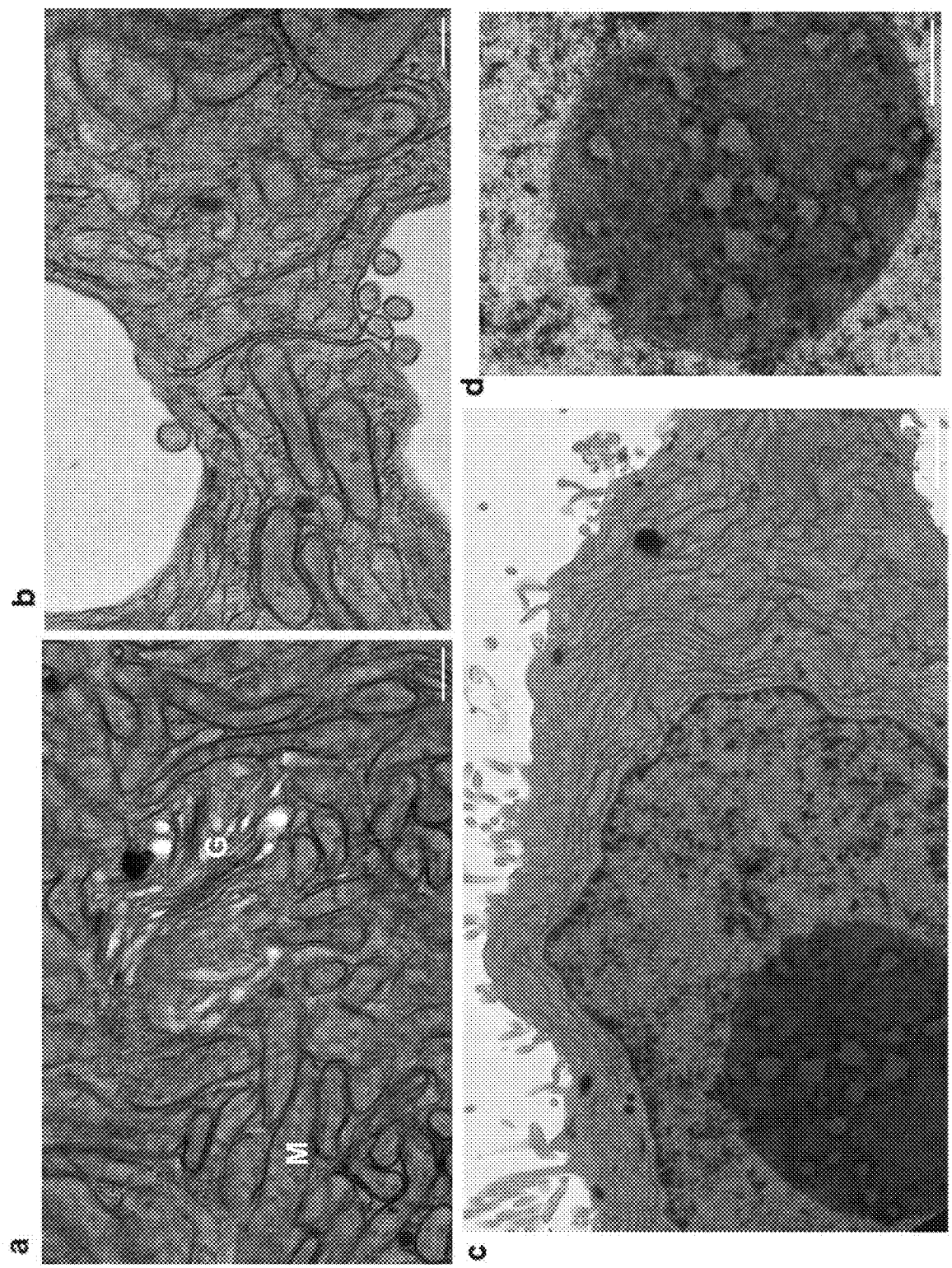
FIG. 12 shows TEM images of hFL-HCC spheroids from TU-2010 plated and maintained in serum-free KM. (a, b) Cells were especially rich in mitochondria (oncocytic condition) with numerous pleomorphic, irregularly shaped, nonlucent mitochondria with irregular cristae disorganization. G=Golgi apparatus. (c, d) Nuclei presented dispersed chromatin and large nucleoli implicating production of secretory proteins. The scale bar=200 nm (a-b), 1 μm (c-d).

That hFL-HCC cells derive from stage-2-hBTSCs was supported further by their behavior in monolayer (FIGS. 4 and 10) and in spheroid cultures (FIGS. 5, 11 and 12). In monolayer cultures, the original hFL-HCCs attached and formed star-like cells (FIGS. 4a and 10), but transitioned rapidly into cells loosely attached and connected to floating cell chains (FIG. 4b), with cells bound to each other via E-cadherin linkages.

If plated overnight with 2-5% fetal bovine serum (FBS) and then switched to serum-free KM (FIG. 4c-4d) or if depleted of murine cells and plated in KM (FIG. 4e), hFL-HCC colonies remained attached, spread and formed colonies strongly expressing pluripotency genes (e.g., NANOG) and stem/progenitor markers (e.g., CD44, LGR5). In vitro invasion assays (FIG. 4f) indicated the invasive properties of hFL-HCCs were greater than Huh7, a human liver cancer cell line, correlating with the invasive potential of hFL-HCCs in vivo, especially with intraperitoneal transplants.

Colony morphologies of hFL-HCCs of TU-2010 were similar to those of stage-2-hBTSCs (FIGS. 18 and 19)—motile cells formed partially ductular structures and were negative for EpCAM in colony centers but transitioned to weak EpCAM expression at colony perimeters.

Assays for drug effects on monolayer cultures (FIG. 4g) of TU-2010 cells indicated that the hedgehog signaling pathway inhibitor, GDC-0449, at 4 µM and especially at 20 µM, and two histone deacetylase (HDAC) inhibitors, SBHA (Suberic bis-hydroxamic acid) at 10 µM and 50 µM and SAHA (suberoylanilide hydroxamic acid) at 2 µM and 10 µM, strongly inhibited hFL-HCC cell growth.

TU-2010 Spheroids, Indicative of Self-Replicative Ability and, Therefore, of CSCs, Formed in KM.

Spheroid formation required that serum-free KM be used throughout, including for plating of cells; spheroids proved able to be passaged for months (FIG. 5a). Transmission electron microscopy (TEM) of spheroids in KM (FIGS. 5b, 11 and 12) revealed tumor cells with microvilli at their apical poles, indicating ability to polarize. Cells were rich in rough endoplasmic reticulum (RER) and Golgi (G), with numerous secretory vesicles containing electron-dense granules typically associated with neuroendocrine traits (e.g. chromogranin) such as occurs in pancreatic tumors. Nuclei contained dispersed chromatin and large nucleoli, implicating high production of secretory proteins. Cells were rich in pleomorphic, irregularly-shaped, non-lucent mitochondria with irregular disorganized cristae. Cells in spheroids proved even more sensitive to inhibition by drugs (SAHA, SBHA, GDC-0449) than in monolayers (FIG. 5d).

Differentiation Media, Used to Lineage Restrict Normal hBTSCs to Adult Fates, Caused hFL-HCCs of TU-2010 to Lose Stemness Traits.

Serum-free, hormonally defined media (HDM), established previously for lineage restriction of hBTSCs to hepatocytes (HDM-H), cholangiocytes (HDM-C) or pancreatic islets (HDM-P), were used to differentiate hFL-HCCs. Cells were monitored for morphological (FIG. 5e) and IHC changes (FIG. 5f) and were assayed by qRT-PCR (FIG. 5g) for stemness (e.g., NANOG, POU5F1, SOX2) and mature markers (e.g., CFTR). Peak levels of stemness traits occurred in KM, whereas those markers were significantly suppressed in all three HDM. In HDM-C, there was an increase in CFTR mRNA and protein (FIG. 5f). CFTR is found in normal stem cells but increases in levels during maturation to cholangiocytes. Higher levels of differentiation were blocked by hFL-HCCs production of matrix-degrading factors.

Transcriptomic Analyses Revealed that hFL-HCCs of TU-2010 Most Closely Resemble hBTSCs.

Figure 6:
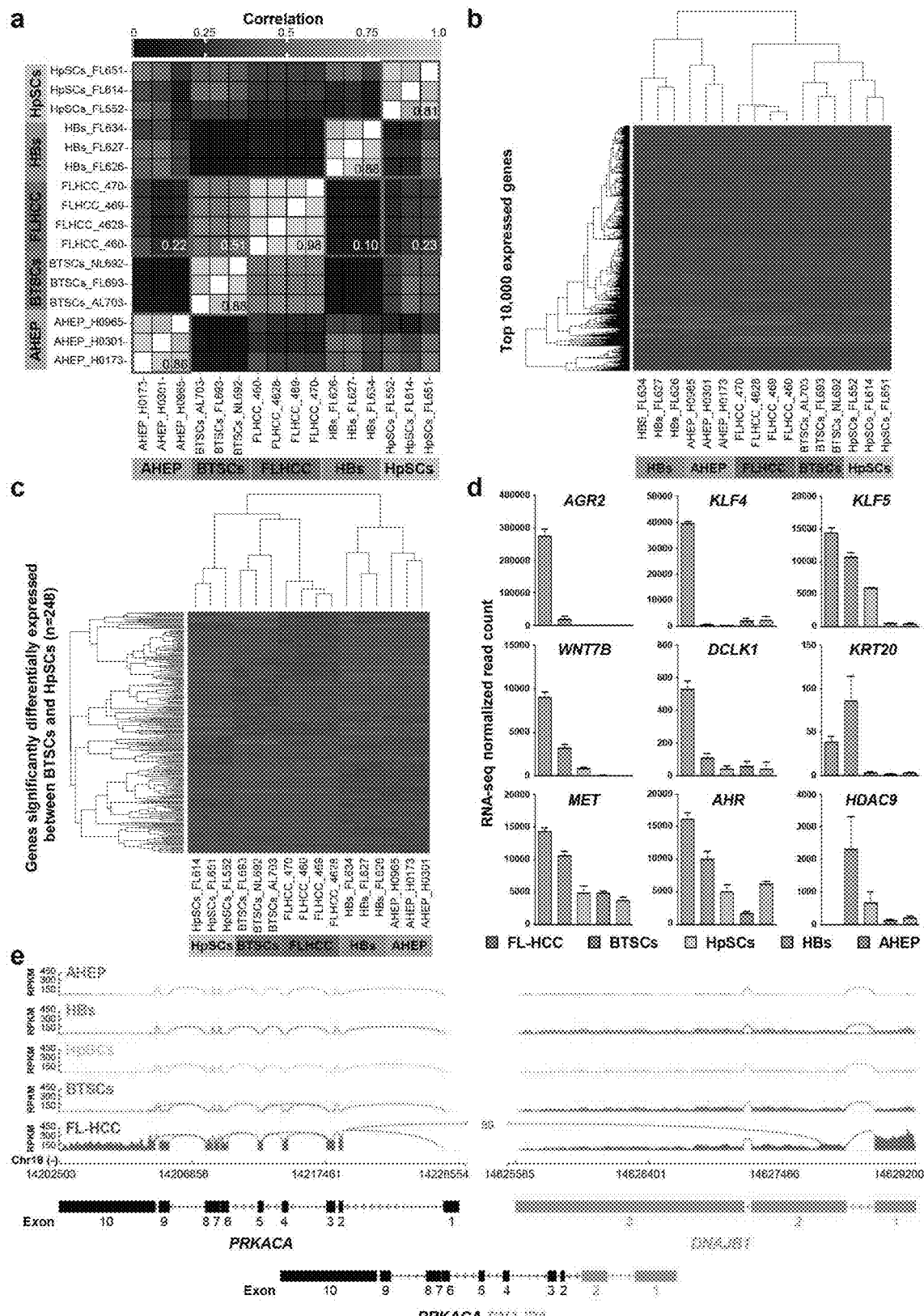
FIG. 6 shows the results of global gene expression analysis by RNA-seq. (a) A correlation heat map of gene expression profiles from RNA sequencing of adult hepatocytes (hAHEPs), biliary tree stem cells (hBTSCs), hepatoblasts (hHBs), and hepatic stem cells (hHpSCs) each from three different donors, as well as fibrolamellar hepatocellular carcinoma (hFL-HCC) from four tumors in different passaged lines of the transplantable tumor line, TU-2010. The tumor cells from TU-2010 were depleted of host (murine) cells before being analyzed by RNA-seq. Values between 0 and 1 shown in each box correspond to the median pair-wise Pearson correlation coefficient. All genes with an average normalized expected count >50 across all samples were included in the analysis (n=14,394). (b, c) Results of hierarchical clustering analysis based on Euclidian distance of gene expression profiles across the different categories of cells using either the 10,000 most highly expressed genes (b) or the 248 genes significantly differentially expressed between hBTSCs and hHpSCs (c). For both (b) and (c), only genes with an average normalized expected count >50 in at least one cell category were considered. (d) Histograms of representative genes with distinct expression patterns in hFL-HCCs are shown. These genes include anterior gradient homolog 2 (AGR2), found expressed in other hFL-HCCs; Kruppel-like factors (KLF4 and KLF5), critical regulators of stemness; WNT7B, a member of the WNT ("wingless-related integration site") family of genes; doublecortin-like-kinase-1 (DCLK1), a marker of intestinal tumor stem cells; cytokeratin 20 (KRT20), found in intestinal and pancreatic cancers; MET, which encodes for the HGF receptor; aryl hydrocarbon receptors (AHR), which can trigger malignant transformation of stem cells upon binding to dioxins and related agonists; and histone deacetylase isoform 9 (HDAC9), which regulates chromatin accessibility. (e) Sashimi plot of RNA-seq read coverage and splice/fusion junctions (shown as arcs) for the fusion gene, DNAJB1-PRKACA, found only in the cells of the hFL-HCC transplantable tumor line. Solid peaks depict reads per kilobase per million reads mapped (RPKM). The fusion junction joins part of exon 2 of DNAJB1 with the start of exon 2 of PRKACA. The four replicate samples of hFL-HCC tumors had 89, 139, 91, and 59 reads, respectively, that spanned the fusion junction. The fusion gene is not present in normal hBTSCs, hHpSCs, hHBs, or hAHEPs.
Figure 13:
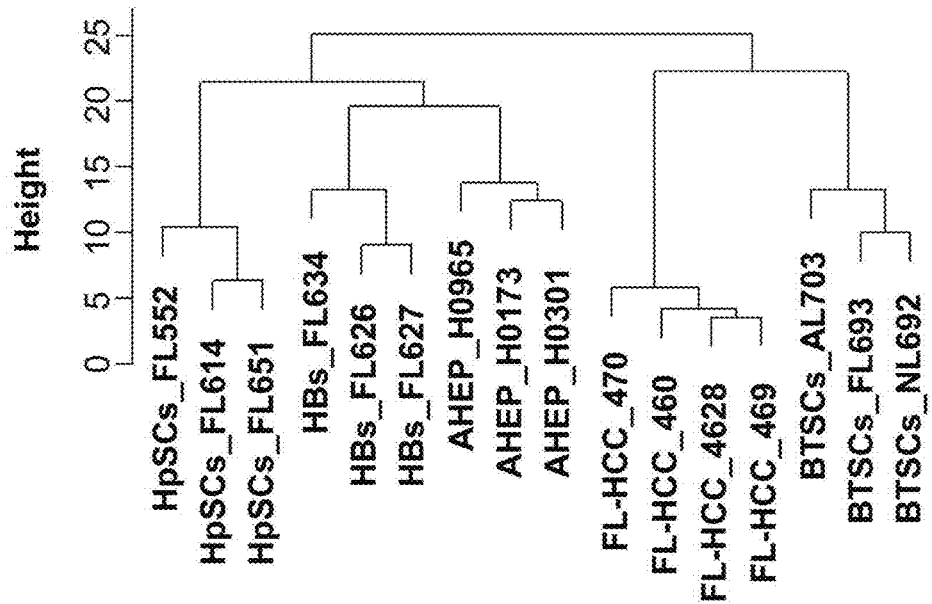
FIG. 13 shows the results of hierarchical clustering analysis. All samples were clustered based on the expression profiles of genes significantly differentially expressed between hBTSCs and hHpSCs (n=248). The hFL-HCCs from TU-2010 clustered closest to hBTSCs and furthest from hHpSCs. The hHBs and hAHEPs clustered more closely with hHpSCs than hFL-HCCs from TU-2010 and hBTSCs. Euclidean distance was used as the clustering metric.

Paired-end high-throughput RNA sequencing was conducted in purified populations of adult human hepatocytes (hAHEPs), hHBs, hHpSCs, and hBTSCs, each from three different donors, as well as four hFL-HCCs from different passaged lines of the transplantable tumor (FIG. 6). An average of about 200 million paired-end reads per sample were obtained, of which an average of about 87% mapped uniquely to the human genome. Gene expression profiles were strongly correlated among samples within each category (average Pearson's $r^2$=0.98 for the hFL-HCC preparations; 0.88 for hHBs and hBTSCs; and 0.81 for hHpSCs) (FIG. 6a). The high correlation among the hFL-HCC samples indicated remarkable stability of gene expression throughout four years of passaging in mice. Cross-category comparisons revealed that gene expression profiles of hFL-HCCs were most strongly correlated with those of hBTSCs (FIG. 6a). This finding was further supported by results of hierarchical clustering analyses, showing that hFL-HCCs are more closely related to hBTSCs than hHpSCs, hHBs, or hAHEPs (FIGS. 6b-6c and 13).

Unique features of hFL-HCCs of TU-2010 (FIG. 6d) included high expression of AGR2; DCLK1; and KRT20, all found in endodermal cancers, particularly of intestine; KLF4/5, critical regulators of stemness; and AHR, shown to trigger malignant transformation of stem cells upon binding to dioxins and related agonists. Interestingly, HDAC9, which is most highly expressed in hBTSCs, is missing altogether in hFL-HCCs and has been linked to tumor suppressive activity through effects on p53.

Figure 14:
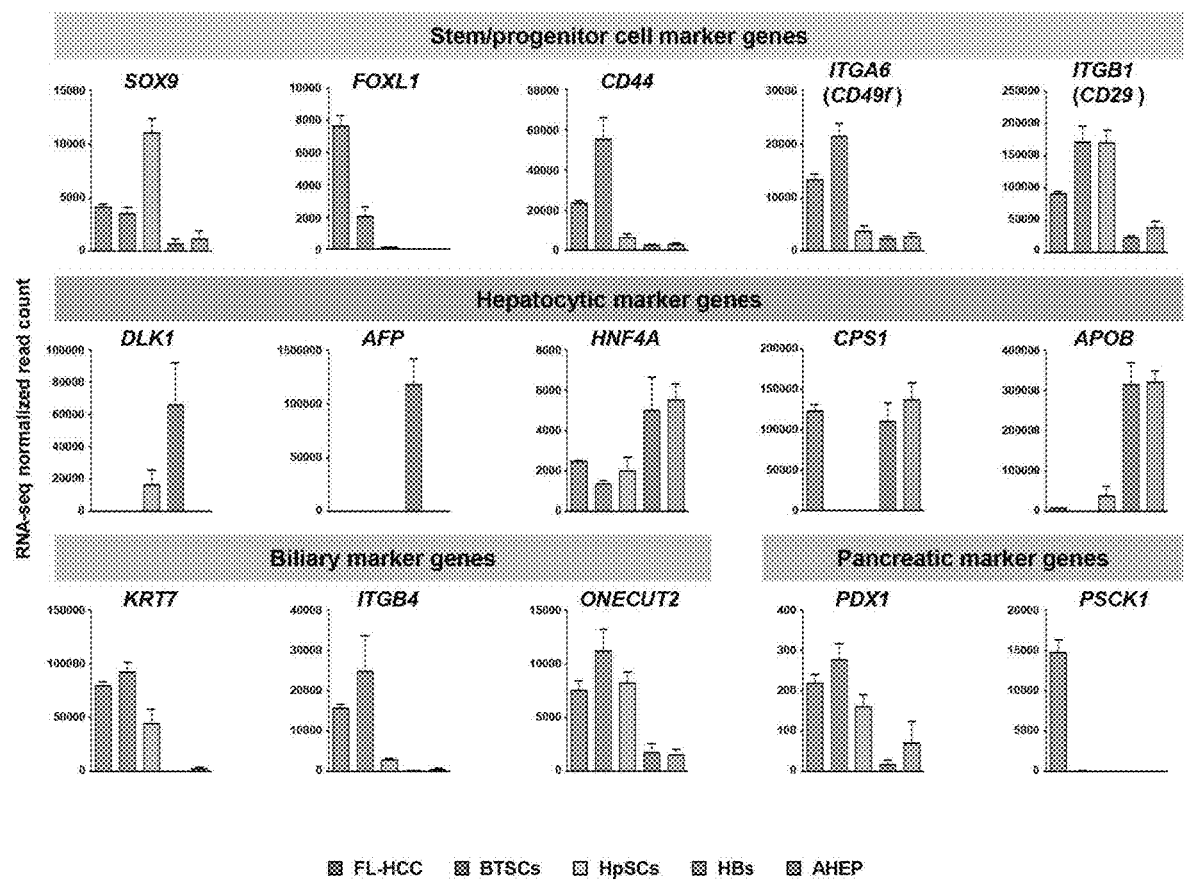
FIG. 14 shows expression data for representative cell type marker genes. RNA-seq normalized expected count data shown across all cell types for genes that have previously been reported as markers of stem cells/progenitors (SOX9, FOXL1, CD44, ITGA6 (CD49f), and ITGB1 (CD29), hepatocytes (DLK1, AFP, HNF4A, CPS1, and APOB), biliary tree (KRT7, ITGB4 and ONECUT2), and pancreas (PDX1 and PCSK1). Error bars represent standard error of the mean.
Figure 15:
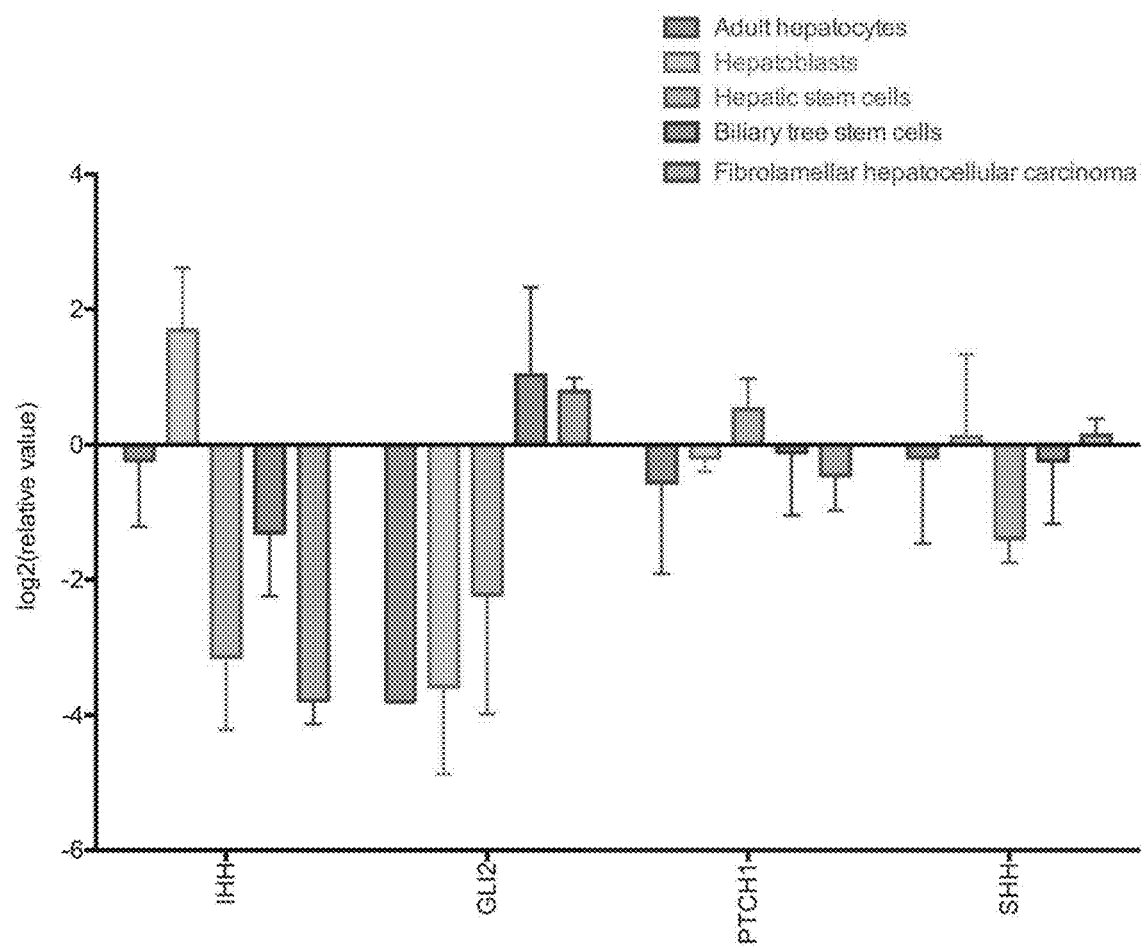
FIG. 15 shows expression data for genes in the hedgehog signaling pathway. Log$_2$ relative expression value shown across all cell types for genes in the hedgehog signaling pathway. Error bars represent standard error of the mean.
Figure 16:
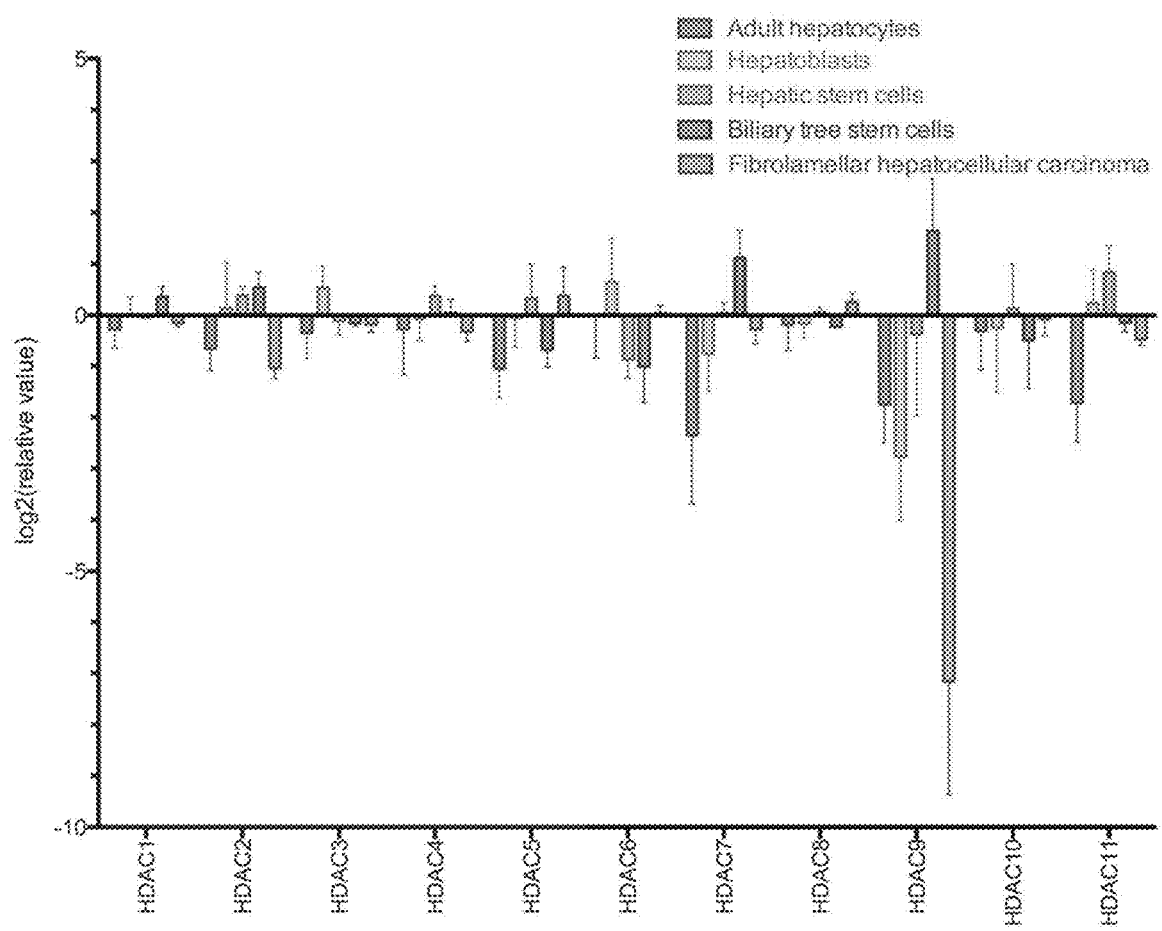
FIG. 16 shows expression data for genes encoding histone deacetylases. Log$_2$ relative expression value shown across all cell types for genes that code for histone deacetylases. Histone deacetylase 9 (HDAC9) is lost entirely in hFL-HCCs. Error bars represent standard error of the mean.

Expression data are shown for representative stem/progenitor, hepatocytic, biliary, and pancreatic genes (FIG. 14), components of the hedgehog signaling pathway (FIG. 15), and HDAC genes (FIG. 16). Results of pathway enrichment analysis for genes differentially expressed in hFL-HCCs compared to hHpSCs or hBTSCs are shown in FIG. 17.

Finally, RNA-seq data were further analyzed using MapSplice2 and detected with high confidence a recurrent fusion transcript unique to hFL-HCCs, DNAJB1-PRKACA, for which Sashimi plots are shown in FIG. 6e. This chimera was identified previously in hFL-HCC tumors, and was demonstrate to be uniquely expressed in hFL-HCCs and not in normal stem cells or adult hepatocytes.

Transcriptomic analyses revealed unique molecular signature of hFL-HCCs and candidate therapeutic targets. To further examine the molecular characteristics of hFL-HCCs, the The Cancer Genome Atlas (TCGA) liver cancer database was mined for hFL-HCCs. Based on the presence of DNAJB1-PRKACA and/or classic histological features, 7 hFL-HCC samples were identified, four of which were incorrectly annotated by TCGA as HCCs. The gene expression profiles of these 7 hFL-HCCs clustered most closely with each other and were clearly distinct from HCCs (n=262) and CCAs (n=36). Expression levels of previously suggested RNA markers of hFL-HCC were analyzed (e.g. AGR2, KRT7, and NTS), and it was found that, with the exception of PCSK1 and DNAJB1-PRKACA, none appear to uniquely mark hFL-HCC relative to HCCs, CCAs, normal livers (n=50), or normal cholangiocytes (n=9) and thus may not be clinically actionable (Data not shown).

Figure 21:
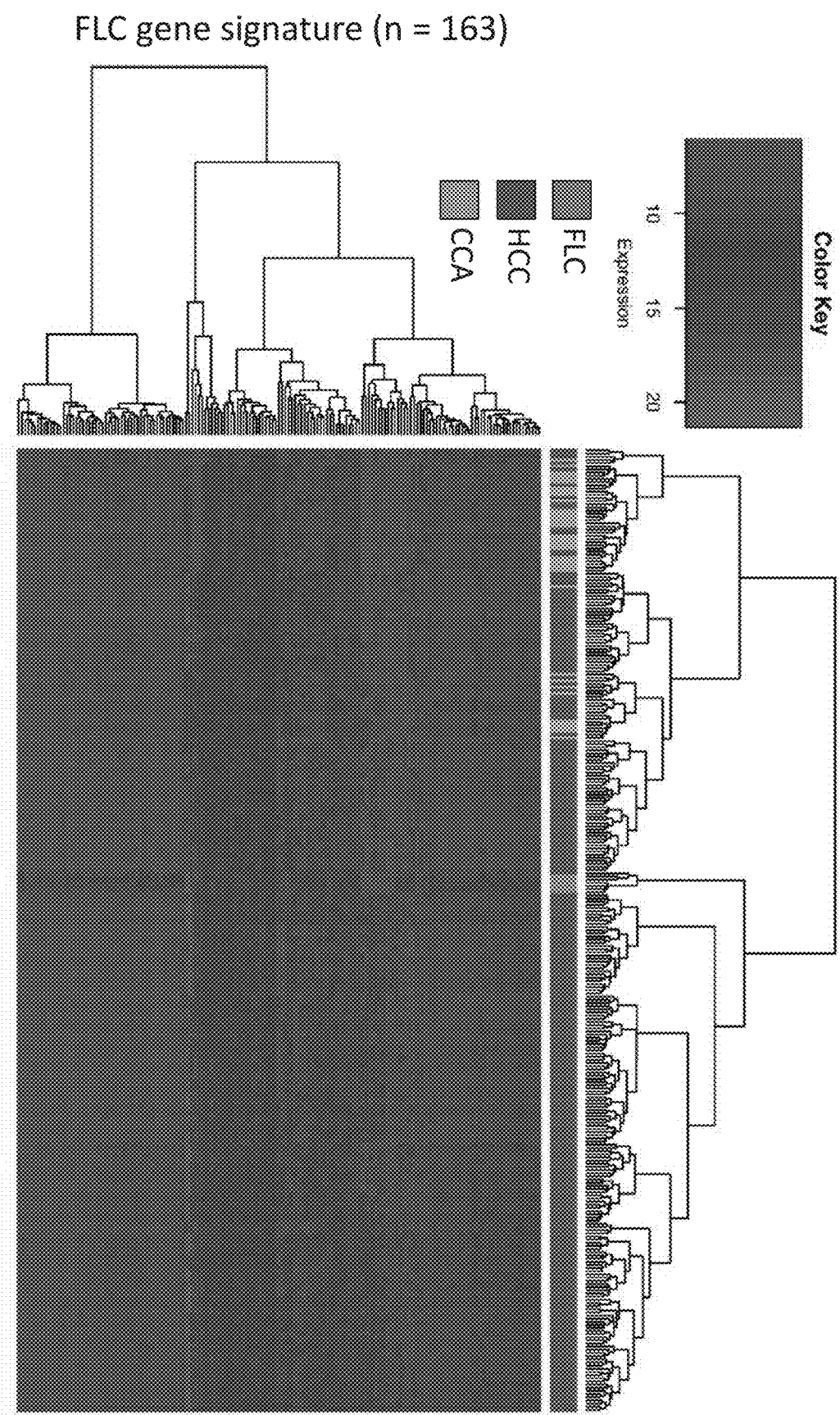
FIG. 21 shows hierarchical clustering based on RNA expression of 163 genes differentially expressed between FL-HCC tumor cells (FLC) and both hepatocellular carcinoma (HCC) and cholangiocarcinoma (CCA) uniquely clusters FLC samples.
Figure 22:
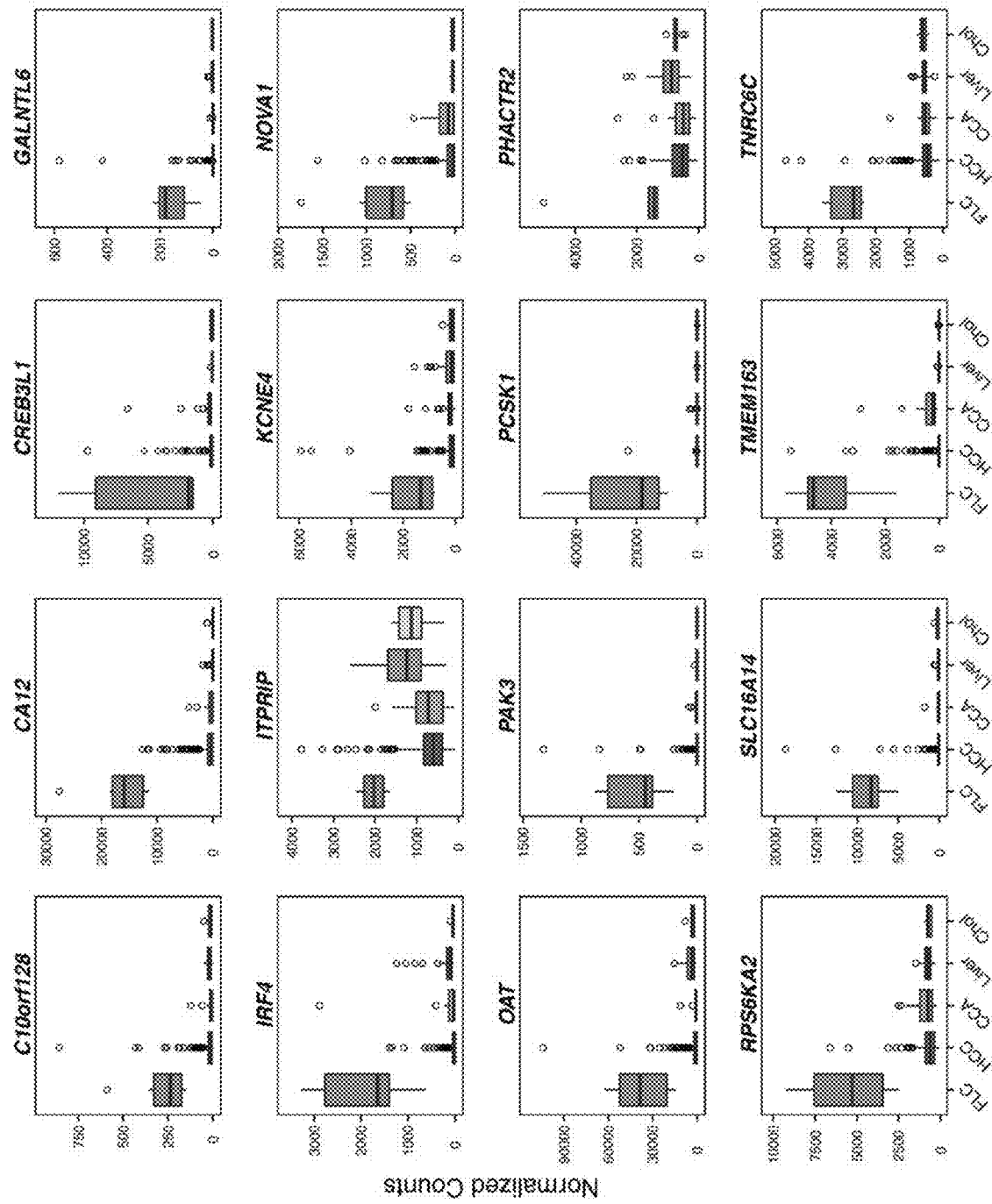
FIG. 22 shows RNA expression within a 16 gene subset of the 163 differentially expressed genes most uniquely distinguishes FLC from HCC and CCA as well as non-tumor liver (Liver) and cholangiocytes (Chol).
Figure 23:
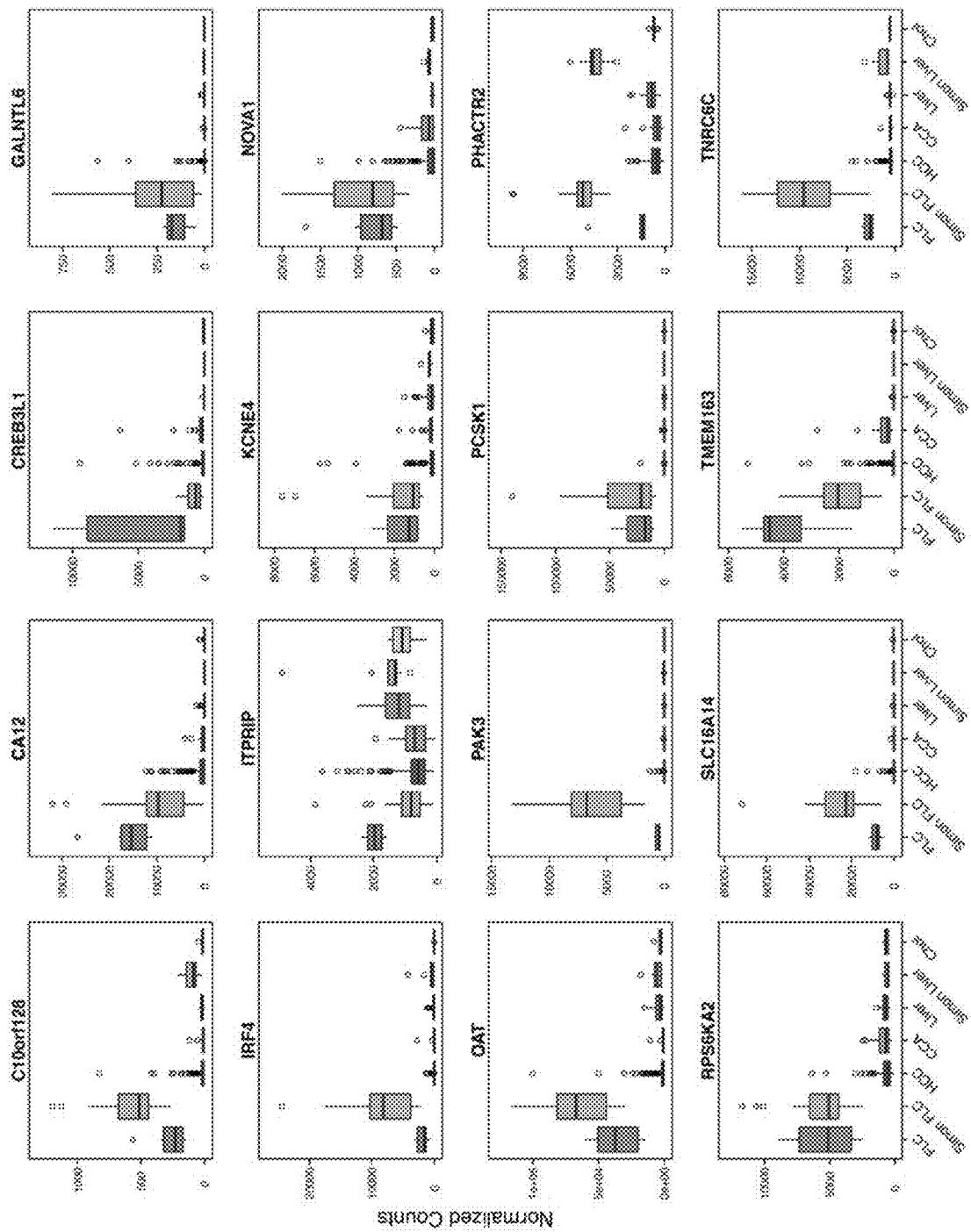
FIG. 23 shows validation of the most uniquely expressed 16 genes in FLC in an independent FLC cohort (Simon). Primary tissues shown above include The Cancer Genome Atlas (TCGA) FLC (FLC), validation FLC set (Simon FLC), TCGA HCC, TCGA CCA, TCGA non-tumor liver (Liver), validation set non-tumor liver (Simon Liver) and TCGA non-tumor cholangiocytes (Chol).
Figure 24:
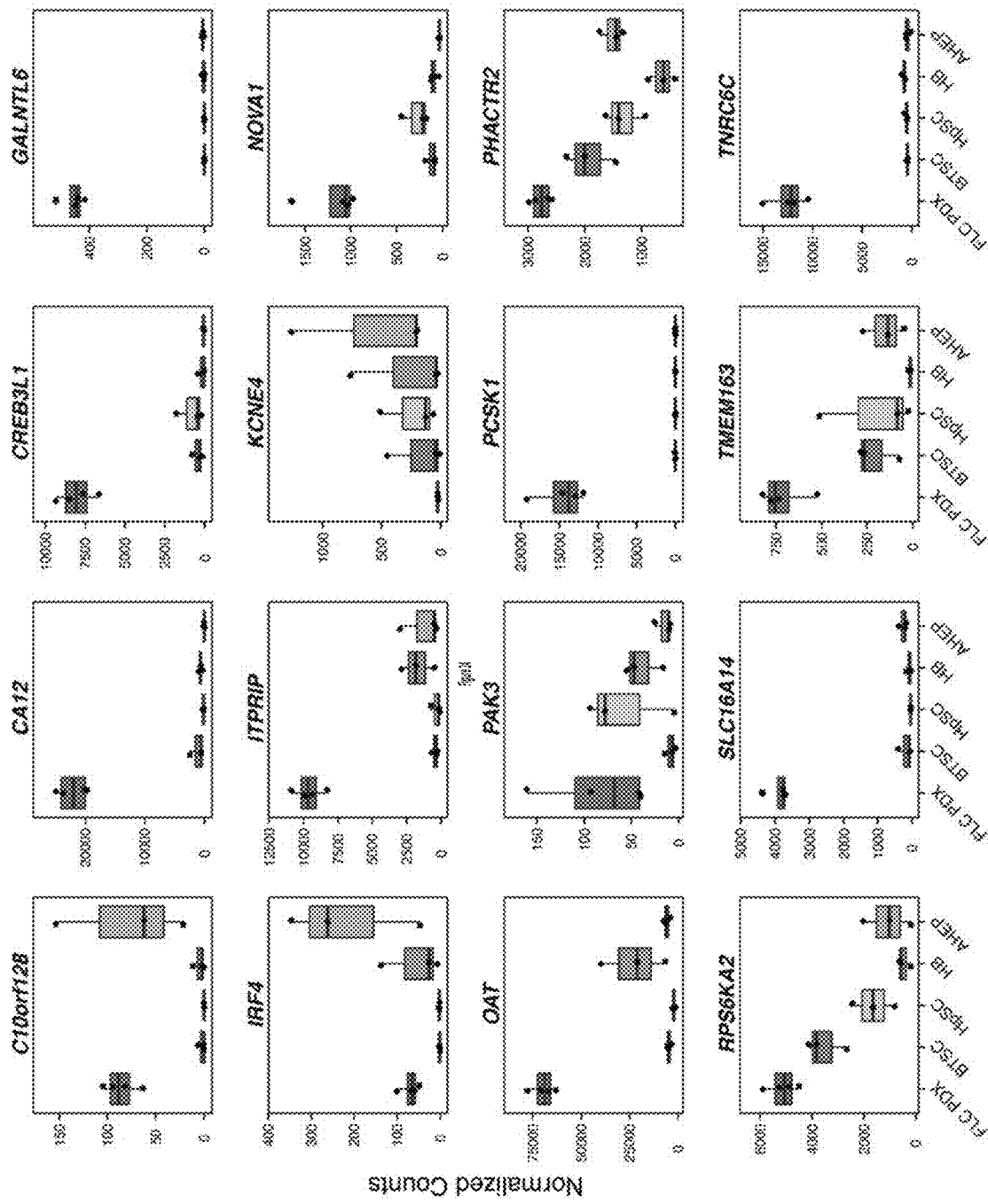
FIG. 24 depicts RNA expression within a 16 gene subset of the FLC gene signature distinguishes purified FLC tumor cells from biliary tree stem cells, the likely cell type of origin, and other cell types within the liver. Cell types shown are purified FLC tumor cells from a patient-derived xenograft (FLC PDX), biliary tree stem cells (BTSC), hepatic stem cells (HpSC), hepatoblasts (HB), and adult hepatocytes (AHEP).
Figure 25:
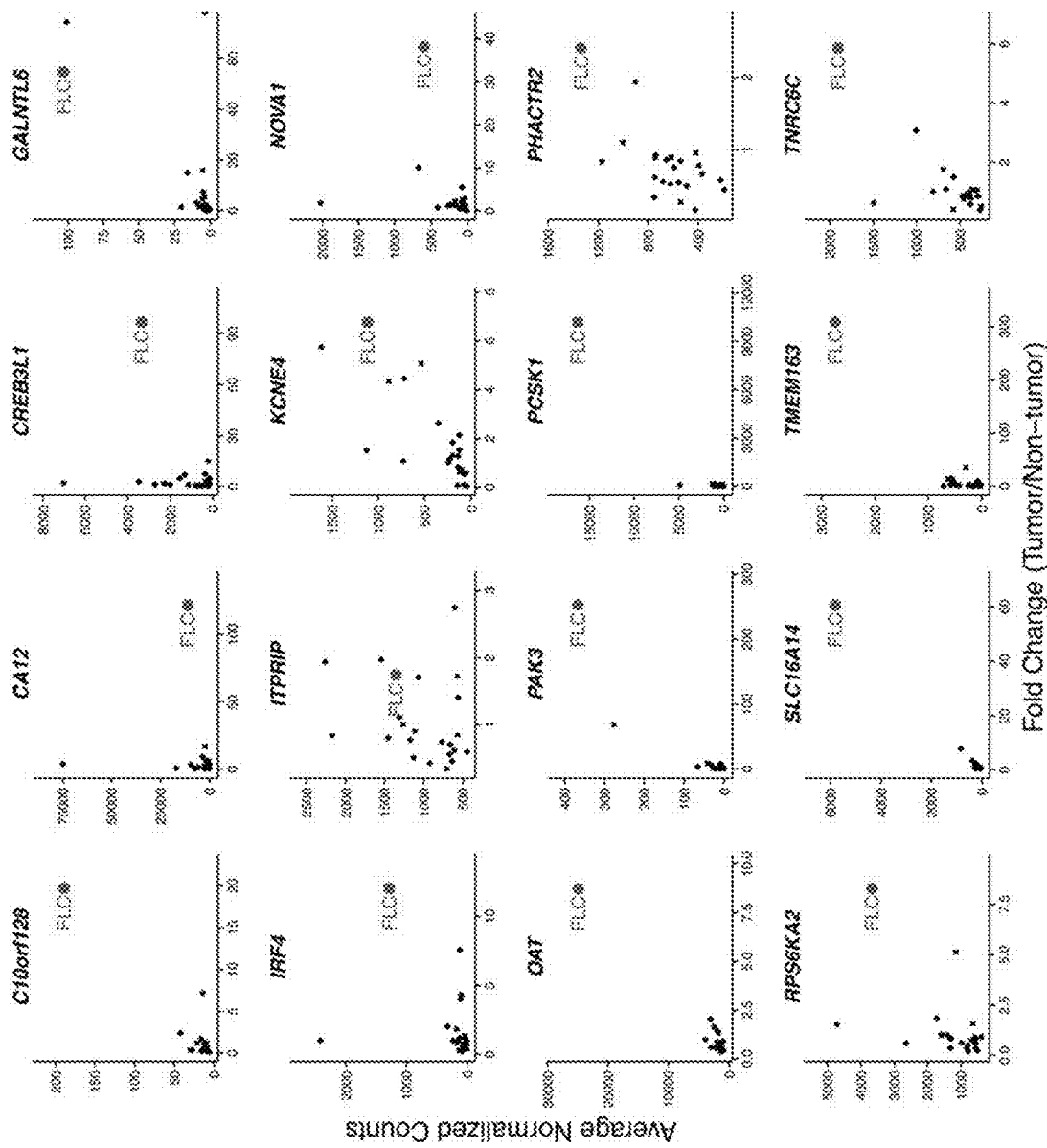
FIG. 25 depicts RNA expression within a 16 gene subset of the FLC gene signature distinguishes FLC from 23 other tumor types.

Therefore, a comprehensive transcriptomic analysis was performed and identified a suite of 165 genes that were significantly altered in hFL-HCCs relative to HCCs and CCAs (FIG. 21). Furthermore, all of the hFL-HCC samples exhibited greater expression than 95% of the HCC and CCA samples for the 16 genes (FIG. 22). The elevated expression of the 16 genes, were further validated in an independent hFL-HCC sample (set of hFL-HCC samples (originally described by Dr. Sanford Simon, Rockefeller University, NYC) and non-tumor liver and non-tumor cholangiocytes (FIG. 23). Among these, the following 7 genes were the most unique to FLC: PCSK1, CA12, NOVA1, SLC16A14, TNRC6C, TMEM163, and RPS6KA2 (FIG. 22). None of these except PCSK1 have been reported previously as hFL-HCC markers. In addition 8 genes (C10orf128, OAT, PAK3, PCSK1, PHACTR2, SLC16A14, TMEM163, and TNR6C) have a greater average of expression in hFL-HCCs as compared to 23 other tumor types from different tissue (FIG. 25). To determine which, if any, of these genes are the strongest candidates for drivers of FLC tumor progression, expression levels in the hFL-HCC tumor model was compared with its presumptive normal counterpart, BTSCs. Surprisingly, all 7 were elevated in the tumor model relative to hBTSCs, and 5 genes were significantly altered (FIG. 24). In addition, genes that are differentially expressed in hFL-HCCs relative to hBTSCs are significantly enriched for predicted target sites of several microRNAs (miRNAs), including miR-10b, which has been implicated in tumorigenesis and the maintenance of CSCs. Quantitative PCR analysis revealed that miR-10b was significantly up-regulated (~17-fold, P=0.03) in hFL-HCCs compared to BTSCs whereas a control miRNA, one not implicated in cancer stem cell maintenance, miR-33a, was unaltered (Data not shown). Together, these data suggest novel markers and drivers of cancer stem cells in hFL-HCCs.

Gene Ontology Molecular Function Analysis to Identify Network Hub Proteins for Targeted hFL-HCC Therapeutics Identifying the protein networks involved in the molecular signature of hFL-HCCs could not only help it providing potential mechanisms of action but could also help to identify additional candidate therapeutic targets. It is contemplated that by controlling "upstream" or "downstream" targets of the genes of the hFL-HCC signature, one may be able to better treat hFL-HCC.

Figure 26:
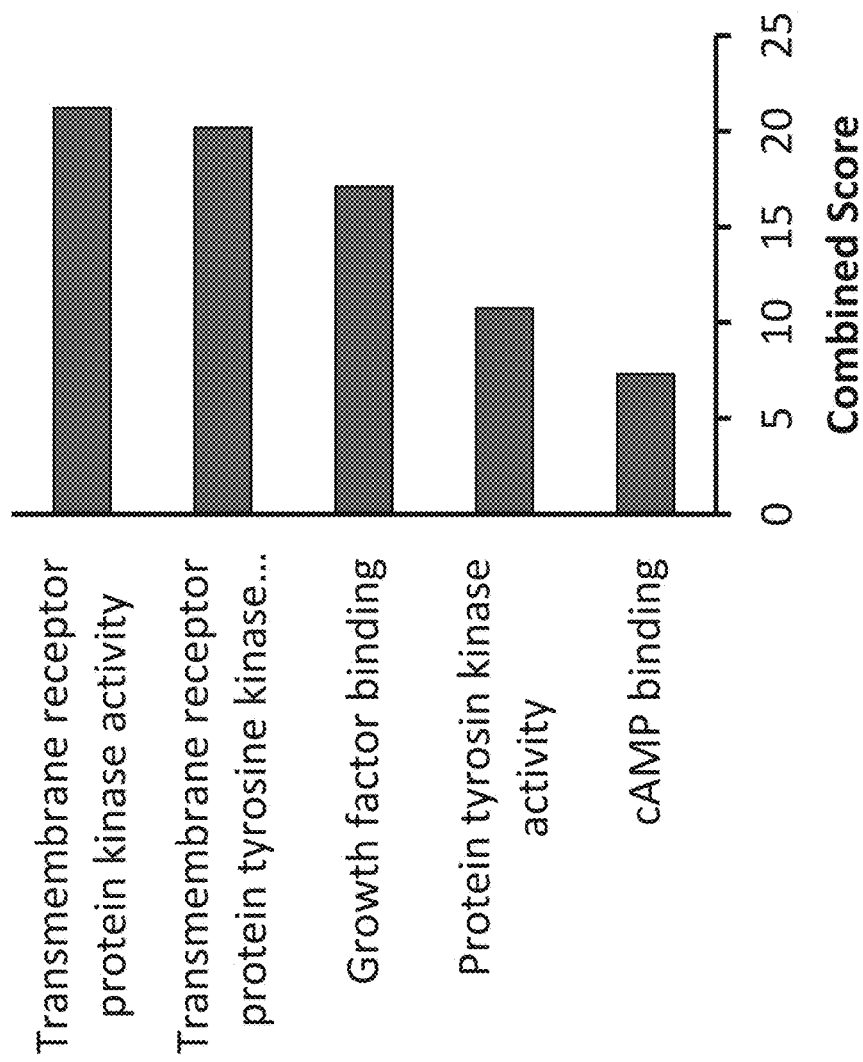
FIG. 26 summarizes Gene Ontology Molecular Function Analysis results of the 165 hFL-HCC gene signature showing enrichment in kinase activity, growth factor binding, and cyclic adenosine monophosphate (cAMP) binding.
Figure 27:
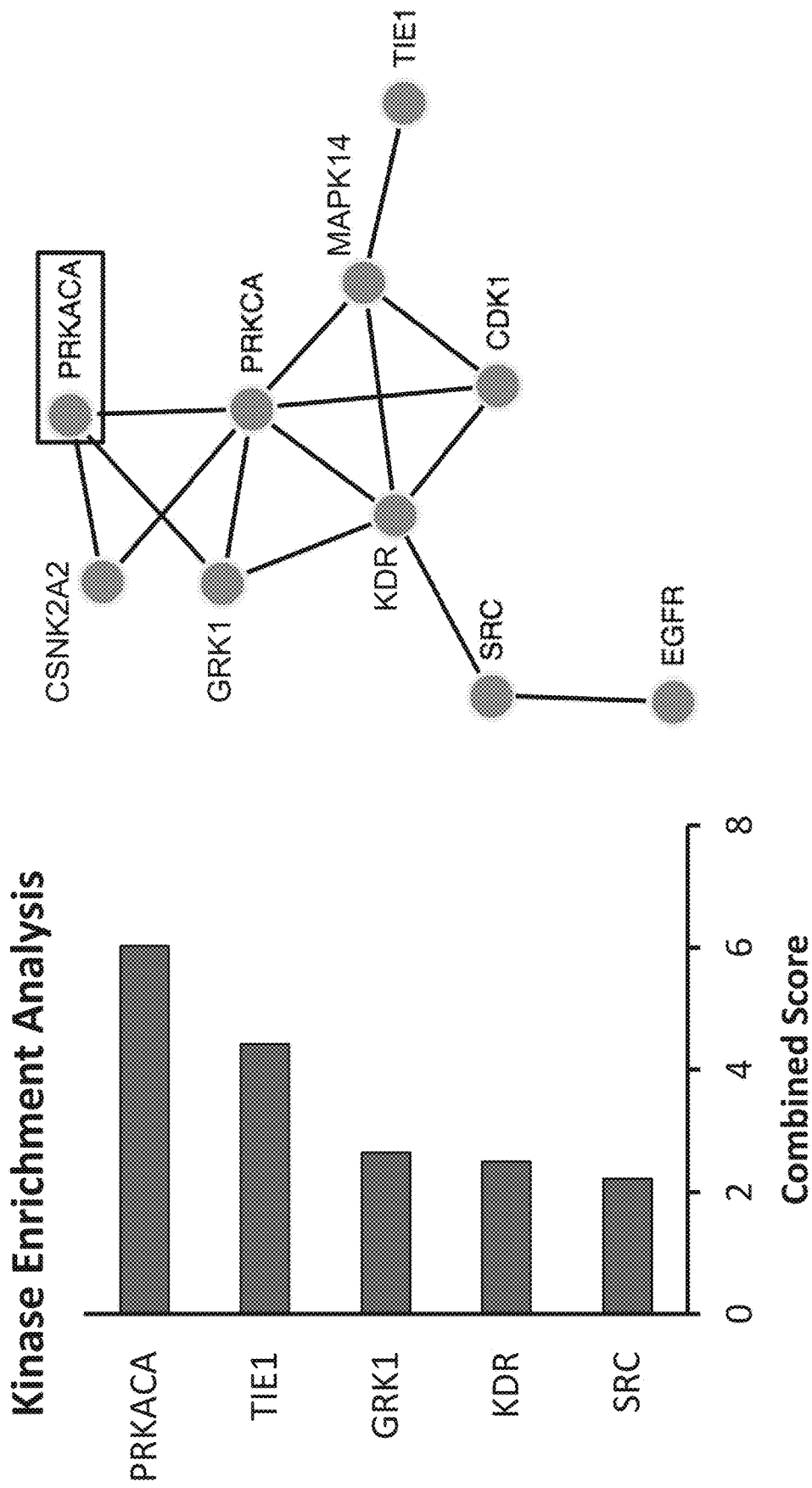
FIG. 27 depicts Kinase Enrichment Analysis results of the 165 hFL-HCC gene signature showing enrichment in substrate targets of Protein kinase A catalytic subunit alpha (PRKACA)

Gene ontology molecular function analyses were performed and revealed that the 165 hFL-HCC specific genes are enriched in kinase activity, growth factor binding, and cAMP (cyclic adenosine monophosphate) binding, suggesting potential mechanisms of action. FIG. 26. In addition, Kinase Enrichment Analysis results of the 165 hFL-HCC gene signature showed enrichment in substrate targets of Protein kinase A catalytic subunit alpha (PRKACA). These substrate targets include, for example, tyrosine kinase with immunoglobulin-like and EGF-like domains 1 (TIE1); G protein-coupled receptor kinase 1 (GRK1); kinase insert domain receptor (KDR); sarcoma (SRC) (gene); casein kinase 2 subunit alpha (CSNK2A2); protein kinase c alpha (PRKCA); mitogen-activated protein kinase 14 (MAPK14); cyclin-dependent kinase 1 (CDK1); and epidermal growth factor receptor (EGFR). FIG. 27.

Figure 28:
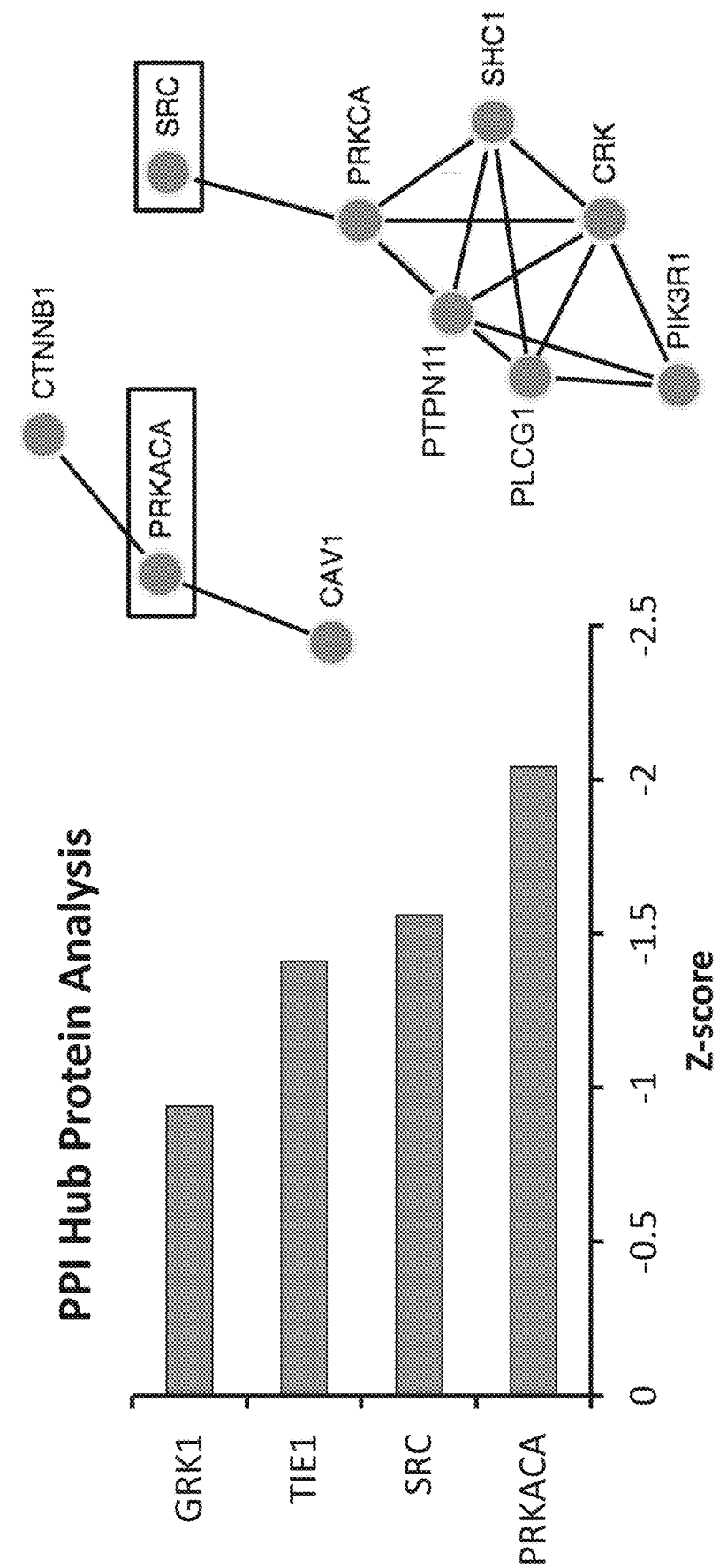
FIG. 28 summarizes the results from Protein-Protein Interaction (PPI) Hub Protein analysis and shows PRKACA and sarcoma (SRC) gene may function as network hubs in hFL-HCCs.

Protein-Protein Interaction (PPI) Hub Protein analysis showed PRKACA and sarcoma (SRC) gene may function as network hubs in hFL-HCCs. Additional proteins in these hubs include, for example, tyrosine kinase with immunoglobulin-like and EGF-like domains 1 (TIE1); G protein-coupled receptor kinase 1 (GRK1); catenin beta-1 (CTNNB1); caveolin-1 (CAV1); protein kinase c alpha (PRKCA); protein tyrosine phosphatase, non-receptor type 11 (PTPN11); Src homology 2 domain containing transforming protein 1 (SHC1); phospholipase C, gamma 1 (PLCG1); V-crk avian sarcoma virus CT10 oncogene homolog (CRK); and phosphoinositide-3-kinase, regulatory subunit 1 (PIK3R1). FIG. 28

Discussion

Phenotypic properties of hFL-HCCs, rare liver cancers, derive in part from their richness in CSCs (over 60% in the transplantable tumor line) and their origins from hBTSCs, precursors to liver and pancreas. These findings provide clarifications for hFL-HCCs' hepatic, cholangiocytic, and endocrine markers, as well as intestinal traits, and for why the 5-year survival is only 45%, the overall mortality is 60%, and half the patients have metastases at the point of diagnosis.

The hFL-HCCs have increased in frequency from an unrecognized liver cancer in the 1970s to about 5% of all liver cancers today. As yet, there is no explanation for this increase. Nor is it understood why patients are primarily children to young adults, and more rarely, middle-aged adults, with no prior history of liver disease. The findings of remarkably high levels of AHR receptors in hFL-HCCs and in hBTSCs, in combination with prior report that dioxins preferentially affect stem cells, provides clues about the possible aetiological factors of hFL-HCCs. AHR agonists emerged as environmental factors from the plastic industries since World War II, correlating with increased incidence of hFL-HCCs.

The properties of hFL-HCCs implicate origins from biliary tree stem cells, precursors to liver and pancreas and located in peribiliary glands (PBGs) and in crypts at the base of villi within gallbladders. Lineage tracing studies in mammals and zebra fish indicate that the biliary tree is a major reservoir of stem/progenitors contributing to liver organogenesis and, as determined recently, pancreatic organogenesis.

Early stages of malignant transformation of hBTSCs within PBGs have been described. PBGs replete with EpCAM-negative hBTSCs are found in PBGs near the fibromuscular layers throughout the biliary tree, including in the large intrahepatic bile ducts.

IHCs and histology provided evidence for the relationship of hFL-HCCs to endodermal stem/progenitors. Histology demonstrated the typical bands of stroma surrounding clumps of large tumor cells having prominent nuclei and aberrations in mitochondria. Co-expression was found for stem/progenitor markers (NANOG, OCT4, SALL4, SHH) and endodermal transcription factors (SOX9, SOX17). The hFL-HCCs expressed some hepatic traits (e.g., HNF4, Hep-Par-1), and the remainder expressed pancreatic traits (e.g., PDX1, PCSK1) or both.

More extensive analyses were made possible by establishment of the first-ever model of hFL-HCCs, TU-2010, a transplantable tumor line maintained in NSG mice. Prior efforts to produce hFL-HCC tumor lines (or cell lines) failed, including those with the ascites tumor cells able to generate a tumor line for these studies. Success proved dependent on culture selection in Kubota's Medium, a serum-free medium designed for endodermal stem/progenitors and not permissive for survival of later maturational lineage stages. The speed of passaging was enhanced with supplements, particularly hyaluronans, HGF and VEGF.

Striking features of the transplantable tumor line, TU-2010, were its desmoplastic traits. Although high levels of tumor stroma occur in HCCs and in CCAs, the transplantable hFL-HCC line, TU-2010 generated subcutaneous tumors comprised of 55-70% host stroma and intraperitoneal ones with more than 95% host stroma. Immunoselection to remove host cells resulted in tumor cells readily cultured as spheroids and with phenotypic traits consistently expressed even after years of passaging in NSG mice (FIG. 6a). Tumor stroma produced paracrine signals (matrix and soluble signals), which are important in tumor progression and metastasis.

Phenotypic analyses of hFL-HCCs from TU-2010, after removal of host cells, were consistent with those from primary tumors and indicated a relationship to hBTSCs. The tumor line, TU-2010, is strikingly rich in cancer stem cells (CSCs; >65% CSCs based on proportion of LGR5+ cells), a unique finding given that the average percentage of CSCs in HCCs is about 0.5-3%, and that in CCAs is about 10-20%. The richness of CSCs in hFL-HCCs was demonstrated functionally by their ability to form tumors in 100% of the mice with as few as 100 cells and by the relative ease with which they formed spheroids or organoids in culture.

The TEM studies on the spheroids from TU-2010 revealed many noteworthy features, but perhaps the most striking were the electron-dense granules and the extraordinary numbers of mitochondria with abnormal cristae, a condition typical of certain cancers. This suggests that the mitochondria generated ATP by oxidative phosphorylation and made the cells tolerant of hypoxia. An oncocytic condition with such pleomorphic mitochondria is not known to be associated with HCCs but with pancreatic cancers. The secretory granules could contain factors responsible for the ability of hFL-HCCs to dissolve every type of matrix tested as substratum.

The strongest evidence of hBTSCs as the origins of hFL-HCCs derives from RNA-seq studies, which includes analyses of genes across successive lineage stages from hBTSCs to hHpSCs to hHBs to adult hepatocytes. The global transcriptome-wide analyses indicate that hFL-HCCs from TU-2010 much more closely resemble hBTSCs than the other lineage stages analyzed. Also, the RNA-seq analyses independently confirmed that hFL-HCCs uniquely express the DNAJB1-PRKACA chimera, a fusion gene coupling the catalytic site of protein kinase A (PKA) and a heat shock protein, resulting in stable activation of PKA.

Genetic analyses have identified unique patterns of claudins, tricellin, CD68, and other biomarkers, ones distinct from those in other liver cancers. Earlier studies also indicated that hFL-HCCs have Mosaic G-protein alpha-subunit (GNAS)-activating mutations, characterized by STAT3 activation, EGF receptor levels higher than in other types of hepatic tumors, and no K-RAS mutations.

The resistance of hFL-HCCs to chemotherapies is predictable, given the cells' expression of multidrug resistance genes. Their renowned aggressiveness in patients and in immune-compromised hosts correlates with expression of multiple genes, including adhesion molecules (E-cadherin, VCAM-1), matrix receptors (CD44), and syndecan-1 (HS-PG), known for binding FGFs, VEGFs, and other growth factors and presenting them as potent mitogens.

The findings that HDAC and hedgehog inhibitors are potent suppressors of growth and survival of hFL-HCCs from TU-2010 indicate new therapeutic options. Similar effects were previously observed with hedgehog inhibitors on normal stem cells, a finding complemented by parallels in expression of hedgehog genes in hFL-HCC versus hBTSCs. By contrast, expression patterns of HDAC genes are distinct in hFL-HCCs versus other parenchymal lineage stages. An intriguing finding is the complete loss of HDAC9 in hFL-HCC.

The TU-2010 tumor's richness in CSCs, the probable origins from biliary tree stem cells, the finding that AHR agonists could be etiological factors in the cancer, and the transplantable tumor line described herein offer novel diagnostic and therapeutic options, ones much needed for this devastating liver cancer.

The discovery of unique molecular signatures for hFL-HCCs will aid in early detection and identification of appropriate therapeutic regimens. In addition to conventional treatment options, these findings suggest several novel candidate therapeutic options. In particular, small molecule inhibitors of CA12 may be used to suppress cancer growth and are currently in preclinical development. In addition, because aberrant miR-10b regulatory activity may contribute to hFL-HCCs pathogenesis, miR-10b and its target genes may be candidate therapeutic targets. Locked nucleic acids (LNAs) may also be useful for potent inhibition of miRNAs and other genes. LNAs have been developed for both research and therapeutic use. Finally, immunotherapies may be novel candidate therapeutics for treating hFL-HCCs.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

Para. A. A transplantable tumor line of human fibrolamellar hepatocellular carcinoma (hFL-HCC) cells maintained in a non-human animal.

Para. B. The transplantable tumor line of Para A, wherein the non-human animal is immunocompromised.

Para. C. The transplantable tumor line of Paras. A or B, wherein the non-human animal is a mouse.

Para. D. The transplantable tumor line of any one Paras. A-C, wherein the non-human animal is a NOD scid gamma (NSG) mouse.

Para. E. The transplantable tumor line any one Paras. A-D, wherein the hFL-HCC cells are derived from a tumor removed from the liver, from the biliary tree, from a subcutaneous tumor or from an intraperitoneal (ascites) tumor.

Para. F. The transplantable tumor line of any one of Paras A-E, wherein the tumor line comprises hFL-HCC cells and mesenchymal cells of the non-human animal.

Para. G. The transplantable tumor line of any one Paras. A-F, wherein at least 50% of the hFL-HCC cells in the transplantable tumor are cancer stem cells.

Para. H. The transplantable tumor line of any one of Paras. A-G, where the mesenchymal cells are derived from the non-human animal.

Para. I. The transplantable tumor line of any one of Paras. A-H, wherein the human FL-HCC cells express the fusion transcript DNAJB1-PRKACA.

Para. J. The transplantable tumor of any one of Paras. A-I, wherein the hFL-HCC cells substantially do not express HDAC9 or express a lower level of HDAC9 as compared to a human non-FL-HCC cell control sample.

Para. K. The transplantable tumor line of any one of Paras. A-J, wherein the hFL-HCC cells express one or more markers of endodermal transcription factors selected from the group consisting of SOX9, SOX17, PDX1, FOXA1, and NGN3.

Para. L. The transplantable tumor line of any one of Paras. A-K, wherein the hFL-HCC cells express one or more markers of pluripotency genes selected from the group consisting of OCT4, SOX2, NANOG, SALL4, KLF4, and KLF5.

Para. M. The transplantable tumor of any one of Paras. A-L, wherein the hFL-HCC cells express one or more markers of other stem cell genes selected from the group consisting of CD44, SALL4, TROP-2, BMI-1, sonic hedgehog (SHH), LGR5, NCAM, and KRT20.

Para. N. The transplantable tumor line of any one of Paras. A-M, wherein the hFL-HCC cells express one or more hepatic markers selected from the group consisting of CK8, CK18, CK19, DCLK1, HepPar-1, albumin, alpha-fetoprotein, and CD68.

Para. O. The transplantable tumor line of any one of Paras. A-N, wherein the hFL-HCC cells express one or more pancreatic markers selected from PDX1, PCSK1, NGN3, insulin, glucagon, amylase, and mucin (MUC).

Para. P. The transplantable tumor line of any one of Paras. A-O, wherein the hFL-HCC cells express high levels of aryl hydrocarbon receptors (AHR).

Para. Q. The transplantable tumor line of any one of Paras. A-P, wherein the hFL-HCC cells express biomarkers of malignancy such as AGR2 and/or high levels of extracellular matrix-degrading enzymes and/or aberrations in the regulation of p53.

Para. R. The transplantable tumor line of any one of Paras. A-Q, wherein the hFL-HCC cells have aberrant or lack of expression of one or more histone deacetylase (HDAC) genes.

Para. S. A transplantable tumor line comprising human FL-HCC (hFL-HCC) cells and mesenchymal cells from a non-human host.

Para. T. The tumor line of Para. S, wherein the non-human host is an immunocompromised mouse.

Para. U. The tumor line of Para. S or T, wherein the non-human host is a NOD scid gamma mouse Para. V. The tumor line of Para. S, which is a xenotransplanted, subcutaneous or intraperitoneal tumor.

Para. W. The tumor line of Para. S, wherein at least 30% of the hFL-HCC cells are cancer stem cells Para. X. The tumor line of Para. S, wherein at least 50% of the hFL-HCC cells are cancer stem cells.

Para. Y. The tumor line of Para. S, wherein at least 65% of the hFL-HCC cells are cancer stem cells.

Para. Z. The tumor line of any one of Paras. S-Y, wherein the hFL-HCC cells express the fusion transcript DNAJB1-PRKACA.

Para. AA. The tumor line of any one of Paras. S-Z, wherein the hFL-HCC cells substantially do not express or express low levels of HDAC9 or express a lower level of HDAC9 as compared to a human non-FL-HCC cell control sample.

Para. AB. The tumor line of any one of Paras. S-AA, wherein the hFL-HCC cells express one or more markers of endodermal transcription factors selected from the group consisting of SOX9, SOX17, PDX1, FOXA1, and NGN3.

Para. AC. The tumor line of any one of Paras. S-AB, wherein the hFL-HCC cells express one or more markers of pluripotency genes selected from the group consisting of OCT4, SOX2, NANOG, SALL4, KLF4, and KLF5.

Para. AD. The tumor line of any one of Paras. S-AC, wherein the hFL-HCC cells express one or more markers of other stem cell genes selected from the group consisting of CD44, SALL4, TROP-2, BMI-1, sonic hedgehog (SHH), LGR5, NCAM, and KRT20.

Para. AE. The tumor line of any one of Paras. S-AD, wherein the human FL-HCC cells express one or more hepatic markers selected from the group consisting of CK7, CK8, CK18, CK19, DCLK1, HepPar-1, albumin, alpha-fetoprotein, and CD68.

Para. AF. The tumor line of any one of Paras. S-AE, wherein the hFL-HCC cells express one or more pancreatic markers selected from the group consisting of PDX1, PCSK1, NGN3, insulin, glucagon, amylase, and mucin (MUC).

Para. AG. The tumor line of any one of Paras. S-AF, wherein the hFL-HCC cells express high levels of aryl hydrocarbon receptors (AHR).

Para. AH. The tumor line of any one of Paras. S-AG, wherein the hFL-HCC cells express biomarkers of malignancy such as AGR2 and/or high levels of extracellular matrix-degrading enzymes.

Para. AI. The tumor line of any one of Paras. S-AH, wherein the human FL-HCC cells have aberrant or lack of expression of one or more histone deacetylase (HDAC) genes.

Para. AJ. A tissue sample obtained from the tumor line of any one of Paras. R-AI.

Para. AK. A cell culture comprising hFL-HCC cells in a serum-free medium.

Para. AL. The cell culture of Para. AK, wherein the serum-free medium is Kubota's Medium.

Para. AM. The cell culture of Para. AK or AL, wherein the serum-free medium contains hyaluronans, HGF and/or VEGF.

Para. AN. The cell culture of any one of Paras. AK-AM, wherein at least 51% of the cells in the cell culture are hFL-HCC cells.

Para. AO. The cell culture of any one of Paras. AK-AN, wherein at least 50% of the hFL-HCC cells in the cell culture are cancer stem cells.

Para. AP. The cell culture of any one of Paras. AK-AO, wherein at least a portion of the hFL-HCC cells are in aggregates of hFL-HCC cells.

Para. AQ. The cell culture of any one of Paras. AK-AP, wherein the hFL-HCC cells express fusion transcript DNAJB1-PRKACA.

Para. AR. The cell culture of any one of Paras. AK-AQ, wherein the hFL-HCC cells substantially do not express HDAC9 or express a lower level of HDAC9 as compared to a human non-FL-HCC cell control sample.

Para. AS. The cell culture of any one of Paras. AK-AR, wherein the hFL-HCC cells express one or more endodermal transcription factors selected from the group consisting of SOX9, SOX17, PDX1, and NGN3.

Para. AT. The cell culture of any one of Paras. AK-AS, wherein the hFL-HCC cells express one or more pluripotency genes selected from the group consisting of SOX2, NANOG, SALL4, OCT4, KLF4, and KLF5.

Para. AU. The cell culture of any one of Paras. AK-AT, wherein the hFL-HCC cells express one or more stem cell genes selected from TROP-2, SALL4, BMI-1, LGR5, sonic hedgehog (SHH), NCAM.

Para. AV. The cell culture of any one of Paras. AK-AU, wherein the hFL-HCC cells express one or more hepatic markers selected from the group consisting of CK7, CK8, CK18 CK19, HepPar-1, albumin, alpha-fetoprotein, LGR5, and CD68.

Para. AW. The cell culture of any one of Paras. AK-AV, wherein the hFL-HCC cells express one or more pancreatic markers selected from the group consisting of PDX1, NGN3, PCSK1, insulin, glucagon, amylase, and mucin (MUC).

Para. AX. A method for establishing a hFL-HCC tumor line comprising: (a) obtaining a human FL-HCC tumor from a patient with hFL-HCC; (b) preparing a tumor cell suspension from the hFL-HCC tumor; (c) culturing the tumor cell suspension under restrictive conditions that select for cancer stem cells to obtain a population of culture-selected cancer stem cells; and (d) transplanting culture-selected cells into an immunocompromised, non-human animal Para. AY. The method of Para. AX, in which the hFL-HCC tumor is obtained as an ascites fluid or as a solid tumor from the subject.

Para. AZ. The method of Para. AX or AY, wherein the tumor cell suspension from the hFL-HCC tumor are cultured on tissue culture plastic or on or in hyaluronans.

Para. BA. The method of any one of Paras. AX-AZ, wherein the tumor cell suspension from the hFL-HCC tumor are cultured in serum-free Kubota's Medium.

Para. BB. The method of any one of Paras. AX-BA, comprising at step (d) transplanting subcutaneously or intraperitoneally the culture-selected cancer stem cells from the hFL-HCC cells into the immunocompromised non-human animal.

Para. BC. The method of any one of Paras. AX-BB, comprising at step (d) transplanting about $10^2$ to about $10^7$ culture-selected cancer stem cells from the hFL-HCC tumor into the immunocompromised, non-human animal.

Para. BD. The method of any one of Paras. AX-BC, further comprising after step (d) monitoring the immunocompromised, non-human animal for tumor formation for about 2 to about 9 months.

Para. BE. A method for maintaining a hFL-HCC transplantable tumor line comprising: (a) obtaining hFL-HCC cells from a xenografted tumor of a maintained in an immunocompromised non-human animal, (b) dispersing the hFL-HCC cells into a cell suspension by enzymatic and/or mechanical methods, and (c) transplanting dispersed hFL-HCC cells into a second immunocompromised, non-human animal.

Para. BF. The method of Para. BE, comprising culturing the hFL-HCC cells in serum-free medium.

Para. BG. The method of Para. BF, wherein the serum-free medium is Kubota's Medium.

Para. BH. The method of Para. BE, wherein the serum-free medium further contains hyaluronans, HGF and/or VEGF.

Para. BI. The method of any one of Paras. BE-BH comprising, at step (c) transplanting subcutaneously or intraperitoneally the hFL-HCC tumor into the second immunocompromised, non-human animal.

Para. BJ. A method for culturing hFL-HCC cells comprising: (a) separating hFL-HCC cells of a xenografted tumor from non-human cells; (b) suspending the separated hFL-HCC cells in a serum-free medium, and (c) plating the hFL-HCC cells as monolayers onto or into a culture substratum to obtain plated hFL-HCC cells or allowing the cells to form floating aggregates.

Para. BK. The method of Para. BJ, comprising at step (c) separating hFL-HCC cells from non-human cells by magnetic immunoselection.

Para. BL. The method of Para. BJ, wherein the culture substratum is a tissue culture plastic, a surface coated with a purified extracellular matrix component or with an extract enriched in extracellular matrix, a 3D hydrogel of a purified extracellular matrix component, or a suspension.

Para. BM. The method of Para. BL, wherein the purified extracellular matrix component is selected from the group consisting of hyaluronan, a collagen, an adhesion molecule, and an extract enriched in extracellular matrix.

Para. BN. The method of Para. BM, wherein the adhesion molecule is laminin.

Para. BO. The method of Para. BM, wherein the extract enriched in extracellular matrix is a matrix scaffold, a biomatrix scaffold, or Matrigel.

Para. BP. The method of Para. BJ, wherein the plated hFL-HCC cells are kept in suspension and allowed to form aggregates.

Para. BQ. A method for drug screening, comprising (a) introducing a candidate drug to cultured hFL-HCC cells that are in the form of monolayers, hydrogels, spheroids or organoids, and (b) monitoring the effect of the candidate drug on the cultured hFL-HCC cells.

Para. BR. A method for drug testing, comprising (a) administering a candidate drug to a non-human animal carrying a transplanted hFL-HCC tumor and (b) monitoring the effect of the candidate drug on the xenotransplanted hFL-HCC tumor.

Para. BS. A method for suppressing the growth of hFL-HCC cells, comprising treating the hFL-HCC cells with a hedgehog signaling inhibitor, a histone deacetylase inhibitor, a protein kinase inhibitor, and/or an inhibitor of a gene overexpressed in hFL-HCC cells.

Para. BT. The method of Para. BS, wherein the hedgehog signaling pathway inhibitor comprises GDC-0449.

Para. BU. The method of Para. BS, wherein the histone deacetylase inhibitor comprises suberoylanilide hydroxamic acid (SAHA) and/or suberic bis-hydroxamic acid (SBHA)

Para. BV. A method for treating hFL-HCC in a patient in need thereof, comprising administering to the patient an effective amount of a hedgehog signaling pathway inhibitor, a histone deacetylase inhibitor, a protein kinase inhibitor, and/or an inhibitor of a gene overexpressed in hFL-HCC cells.

Para. BW. The method of Para. BV, wherein the hedgehog signaling pathway inhibitor comprises GDC-0449

Para. BX. The method of Para. BX, wherein the histone deacetylase inhibitor comprises SAHA and/or SBHA.

Para. BY. A method of determining whether a patient has fibrolamellar hepatocellular carcinoma (FL-HCC), comprising: (a) measuring gene expression levels of at least one of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, and TNRC6C; and (b) comparing the gene expression profile to one or more control samples.

Para. BZ. The method of Para. BY, wherein overexpression of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163 or TNRC6C relative to the control sample is associated with presence of FL-HCC.

Para. CA. The method of Para. BZ, wherein overexpression of PCSK1, CA12, NOVA1, SLC16A14, TNRC6C, TMEM163, and RPS6KA2 relative to the control sample is associated with presence of FL-HCC.

Para. CB. The method of Para. BZ, wherein overexpression of C10orf128, OAT, PAK3, PCSK1, PHACTR2, SLC16A14, TMEM163, and TNRC6C relative to the control sample is associated with presence of FL-HCC.

Para. CC. The method of any one of Paras. BZ-CB, wherein the control sample is selected from the tumor cells from hepatocellular carcinomas (HCCs), hepatoblastomas, cholangiocarcinomas (CCAs) and/or pancreatic cancers or selected from normal cells consisting of biliary tree stem cells, hepatic stem cells, hepatoblasts, pancreatic stem cells, hepatic or pancreatic committed progenitors, and normal mature hepatic or pancreatic cells.

Para. CD. A method of treating a patient determined to have hFL-HCC by administering to the patient an effective amount of at least one therapeutic that decreases expression of at least one of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, or TNRC6C.

Para. CE. The method of Para. CD, wherein the at least one therapeutic is selected from the group consisting of a small molecule, RNA interference, and a locked nucleic acid (LNA).

Para. CF. A method of treating a patient determined to have hFL-HCC by administering to the patient an effective amount of an immunotherapy.

Para. CG. A method of treating a patient determined to have hFL-HCC by administering to the patient an effective amount of at least one therapeutic that regulates PRKACA or SRC network hubs.

Para. CH. A method of treating a patient determined to have hFL-HCC by administering to the patient an effective amount of at least one therapeutic that regulates substrate targets of the kinase PRKACA (Protein kinase A catalytic subunit alpha).

Para. CI. An isolated hFL-HCC cell wherein the hFL-HCC cell expresses a marker selected from the group consisting of C10orf128, CA12, CREB3L1, GALNTL6, IRF4, ITPRIP, KCNE4, NOVA1, OAT, PAK3, PCSK1, PHACTR2, RPS6KA2, SLC16A14, TMEM163, and TNRC6C.

Para. CJ. A population of isolated hFL-HCC cells of Para. CI.

Para. CK. A composition comprising an isolated hFL-HCC cell of Para. CI or CJ and a carrier.

Para. CL. The composition of any one of Paras. CI-CK, wherein the hFL-HCC cells are obtained from ascites fluid or a solid tumor.

Para. CM. The composition of any one of Paras. CI-CL, wherein the hFL-HCC cells are cultured on tissue culture plastic or on or in hyaluronans.

Para. CN. The composition of any one of Paras. CI-CM, wherein the hFL-HCC cells are cultured in cells in serum-free medium.

Para. CO. The composition of any one of Paras. CI-CN, wherein the serum-free medium is Kubota's Medium.

Para. CP. The composition of Paras. CI-CO, wherein the serum-free medium further contains hyaluronans, HGF and/or VEGF.

Para. CQ. The composition of any one of Paras. CI-CP, further comprising purified extracellular matrix component.

Para. CR. The composition of Para. CQ, wherein the purified extracellular matrix component is selected from the group consisting of hyaluronan, a collagen, an adhesion molecule, and an extract enriched in extracellular matrix.

Para. CS. The composition of Para. CR, wherein the adhesion molecule is laminin.

Para. CT. The composition of Para. CR, wherein the extract enriched in extracellular matrix is a matrix scaffold, a biomatrix scaffold, or Matrigel.

Para. CU. A transplantable tumor cell line comprising human fibrolamellar hepatocellular carcinoma (hFL-HCC) cells, which can be maintained in a non-human animal.

What is claimed is:

1. A method for drug screening for treating a patient suffering from human fibrolamellar hepatocellular carcinoma (hFL-HCC), comprising culturing hFL-HCC cells in a serum-free medium to form organoids, introducing a candidate drug to the hFL-HCC in the form of organoids measuring expression of at least one of C1Oorf128, CA12, CREB3L1, GALNTL6, IRF4, ITPRIP, KCNE4, NOVA1, OAT, PAK3, PCSK1, PHACTR2, RPS6KA2, SLC16A14, TMEM163, or TNRC6C in the organoids treated with the candidate drug, and selecting the candidate drug that causes reduced expression of at least one of C1Oorf128, CA12, CREB3L1, GALNTL6, IRF4, ITPRIP, KCNE4, NOVA1, OAT, PAK3, PCSK1, PHACTR2, RPS6KA2, SLC16A14, or TMEM163.

2. The method of claim 1, in which the hFL-HCC cells are derived from a tumor removed from a liver, from a biliary tree, from a subcutaneous tumor or from an intraperitoneal tumor.

3. The method of claim 1, in which the organoids comprise mesenchymal cells.

4. The method of claim 1, in which the hFL-HCC cells express a fusion transcript DNAJB1-PRKACA.

5. The method of claim 1, in which the selected candidate drug reduced expression of at least two of C1Oorf128, CA12, CREB3L1, GALNTL6, IRF4, ITPRIP, KCNE4, NOVA1, OAT, PAK3, PCSK1, PHACTR2, RPS6KA2, SLC16A14, TMEM163, or TNRC6C.

6. The method of claim 1, in which the serum-free medium comprises Kubota's Medium.

7. The method of claim 6, in which the serum-free medium further contains hyaluronan, HGF, and/or VEGF.

8. The method of claim 3, wherein the mesenchymal cells comprise precursors to stellate cells, endothelial cells, stromal cells or pericytes.

9. The method of claim 1, wherein the selected candidate drug has reduced expression of at least PCSK1, CA12, NOVA1, SLC16A14, TNRC6C, TMEM163, and RPS6KA2.

10. The method of claim 1, wherein the selected candidate drug regulates substrate targets of the kinase PRKACA (Protein kinase A catalytic subunit alpha) or carbonic anhydrases.

* * * * *